US012595252B2

(12) United States Patent
Hughes et al.

(10) Patent No.: US 12,595,252 B2
(45) Date of Patent: Apr. 7, 2026

(54) INHIBITORS OF SARM1

(71) Applicant: DISARM THERAPEUTICS, INC., Indianapolis, IN (US)

(72) Inventors: Robert Owen Hughes, Newtown, CT (US); Rajesh Devraj, Chesterfield, MO (US); Todd Bosanac, New Milford, CT (US); Richard Andrew Jarjes-Pike, Newbury (GB); Andrew Simon Brearley, Chilton (GB); Jonathan Bentley, Abindgon (GB); Shelley Anne Parrott, Abindgon (GB); Sophie Catherine Cooper, Abindgon (GB)

(73) Assignee: DISARM THERAPEUTICS, INC., Indianapolis, IN (US)

( * ) Notice: Subject to any disclaimer, the term of this patent is extended or adjusted under 35 U.S.C. 154(b) by 975 days.

(21) Appl. No.: 17/615,907

(22) PCT Filed: Jun. 12, 2020

(86) PCT No.: PCT/US2020/037378

§ 371 (c)(1),
(2) Date: Dec. 2, 2021

(87) PCT Pub. No.: WO2020/252229

PCT Pub. Date: Dec. 17, 2020

(65) Prior Publication Data

US 2022/0340546 A1 Oct. 27, 2022

Related U.S. Application Data

(60) Provisional application No. 62/861,501, filed on Jun. 14, 2019.

(51) Int. Cl.

| | |
|---|---|
| ***C07D 403/12*** | (2006.01) |
| ***C07D 241/18*** | (2006.01) |
| ***C07D 401/12*** | (2006.01) |
| ***C07D 401/14*** | (2006.01) |
| ***C07D 405/12*** | (2006.01) |
| ***C07D 405/14*** | (2006.01) |
| ***C07D 413/12*** | (2006.01) |
| ***C07D 471/04*** | (2006.01) |
| ***C07D 487/04*** | (2006.01) |

(52) U.S. Cl.

CPC ......... *C07D 403/12* (2013.01); *C07D 241/18* (2013.01); *C07D 401/12* (2013.01); *C07D 401/14* (2013.01); *C07D 405/12* (2013.01); *C07D 405/14* (2013.01); *C07D 413/12* (2013.01); *C07D 471/04* (2013.01); *C07D 487/04* (2013.01)

(58) Field of Classification Search

CPC ... C07D 403/12; C07D 401/12; C07D 405/12
See application file for complete search history.

(56) References Cited

U.S. PATENT DOCUMENTS

| | | | | |
|---|---|---|---|---|
| 9,486,521 | B2 | 11/2016 | Freeman et al. | |
| 11,903,935 | B2 * | 2/2024 | Milbrandt | A61P 25/28 |
| 12,083,114 | B2 * | 9/2024 | Bosanac | A61K 31/4375 |
| 2012/0328629 | A1 | 12/2012 | Freeman et al. | |
| 2015/0011575 | A1 | 1/2015 | Walter et al. | |

FOREIGN PATENT DOCUMENTS

| | | | | |
|---|---|---|---|---|
| EP | 1050531 | A1 | 11/2004 | |
| WO | WO-0160806 | A2 * | 8/2001 | A61P 9/10 |
| WO | 2012/178022 | A2 | 12/2012 | |
| WO | 2018/035204 | A1 | 2/2018 | |
| WO | 2018/057989 | A1 | 3/2018 | |
| WO | 2019/236879 | A1 | 12/2019 | |
| WO | 2019/236884 | A1 | 12/2019 | |
| WO | 2019/236890 | A1 | 12/2019 | |
| WO | 2020/081923 | A1 | 4/2020 | |
| WO | 2020/132045 | A1 | 6/2020 | |
| WO | 2020/247701 | A2 | 12/2020 | |

OTHER PUBLICATIONS

Roe et al., The Preparation of Heterocyclic Fluorine Compounds by the Schiemann Reaction.I. The Monofluoropyridines, 1947, Journal of the American Chemical Society, 69, pp. 2443-2444 (Year: 1947).*
Ukrorgsyntez Ltd., RN 1866712-36-8, 2016, CAPLUS (Year: 2016).*
Ukrorgsyntez Ltd., RN 1878025-49-0, 2016, CAPLUS (Year: 2016).*
Ukrorgsyntez Ltd., RN 1878025-71-8, 2016, CAPLUS (Year: 2016).*
Ukrorgsyntez Ltd., RN 1879279-46-5, 2016, CAPLUS (Year: 2016).*
Ukrorgsyntez Ltd., RN 1880323-60-3, 2016, CAPLUS (Year: 2016).*
Ukrorgsyntez Ltd., RN 1881619-70-0, 2016, CAPLUS (Year: 2016).*
Ukrorgsyntez Ltd., RN 2025746-70-5, 2016, CAPLUS (Year: 2016).*
Ukrorgsyntez Ltd., RN 1874857-24-5, 2016, CAPLUS (Year: 2016).*
Enamine, RN 1424456-86-9, 2013, CAPLUS (Year: 2013).*
Ukrorgsyntez Ltd., RN 1694743-67-3, 2015, CAPLUS (Year: 2015).*
RN 6905-47-1, 1984, CAPLUS (Year: 1984).*
Aurora Fine Chemicals, RN 1516709-09-3, 2014, CAPLUS (Year: 2014).*
Enamine, RN 1428041-01-3, 2013, CAPLUS (Year: 2013).*
Aurora Fine Chemicals, RN 1493229-84-7, 2013, CAPLUS (Year: 2013).*
Aurora Fine Chemicals, RN 1502513-50-9, 2013, CAPLUS (Year: 2013).*
Aurora Fine Chemicals, RN 1517681-35-4, 2014, CAPLUS (Year: 2014).*
Ukrorgsyntez Ltd., RN 1851689-39-8, 2016, CAPLUS (Year: 2016).*
Ukrorgsyntez Ltd., RN 1874934-02-7, 2016, CAPLUS (Year: 2016).*
Ukrorgsyntez Ltd., RN 1875035-51-0, 2016, CAPLUS (Year: 2016).*
Ukrorgsyntez Ltd., RN 1875592-76-9, 2016, CAPLUS (Year: 2016).*
Ukrorgsyntez Ltd., RN 1876454-45-3, 2016, CAPLUS (Year: 2016).*

(Continued)

*Primary Examiner* — Brenda L Coleman
*Assistant Examiner* — Madeline E Braun
(74) *Attorney, Agent, or Firm* — Quarles & Brady, LLP

(57) ABSTRACT

The present disclosure provides compounds and methods useful for inhibiting SARM1 and/or treating and/or preventing axonal degeneration.

4 Claims, 1 Drawing Sheet

Specification includes a Sequence Listing.

(56) References Cited

OTHER PUBLICATIONS

Gerdts et al., "Axon self destruction: new links among SARM1, MAPKs, and NAD+ metabolism," Neuron, 2016, vol. 39(3), pp. 449-460.
Lawrence et al., "Development of ortho-Chlorophenyl Substituted Pyrimidines as Exceptionally Potent Aurora Kinase Inhibitors," J Med Chem., 2012, vol. 55(17), pp. 7392-7416.

* cited by examiner

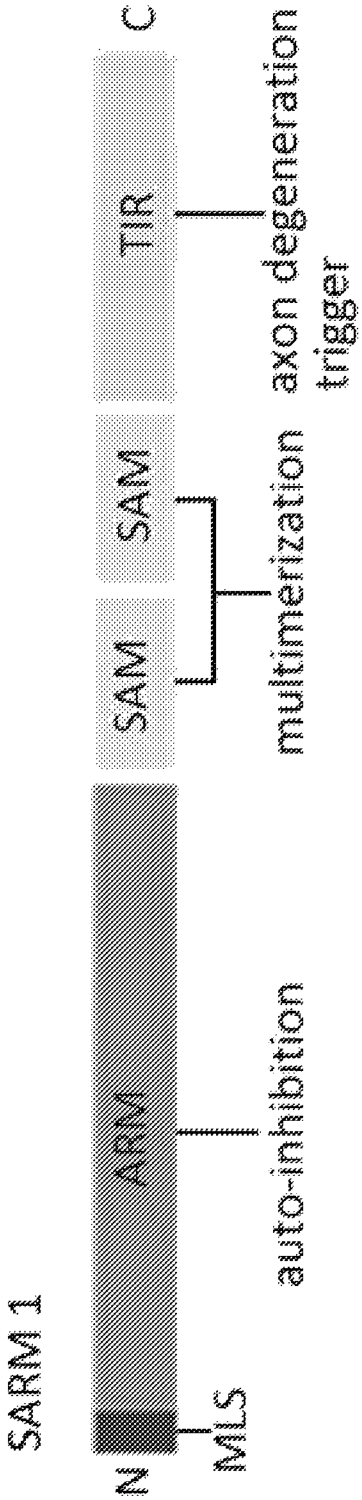
SARM 1
N
MLS
ARM
auto-inhibition
SAM
SAM
multimerization
TIR
axon degeneration trigger
C

INHIBITORS OF SARM1

CROSS REFERENCE TO RELATED APPLICATIONS

This application claims the benefit of U.S. Provisional Application No. 62/861,501, filed Jun. 14, 2019, which is herein incorporated by reference in its entirety.

SEQUENCE LISTING

The instant application contains a Sequence Listing, which has been submitted electronically in ASCII format and is hereby incorporated by reference in its entirety. The ASCII copy, created Jun. 10, 2020 is named 2012800-0037_SL.txt, and is 8,858 bytes in size.

BACKGROUND

Axonal degeneration is a hallmark of several neurological disorders including peripheral neuropathy, traumatic brain injury, and neurodegenerative diseases (Gerdts et al., SARM1 activation triggers axon degeneration locally via NAD(+) destruction. Science 348 2016, pp. 453-457, hereby incorporated by reference in its entirety). Neurodegenerative diseases and injuries are devastating to both patients and caregivers. Costs associated with these diseases currently exceed several hundred billion dollars annually in the Unites States alone. Since the incidence of many of these diseases and disorders increases with age, their incidence is rapidly increasing as demographics change.

SUMMARY

The present disclosure provides technologies useful, among other things, for treating and/or preventing neurodegeneration (e.g., for reducing axonal degeneration). In some embodiments, provided technologies inhibit SARM1.

In some embodiments, the present disclosure provides certain compounds and/or compositions that are useful in medicine, and particularly for treating neurodegeneration (e.g., for reducing axonal degeneration).

In some embodiments, the present disclosure provides compounds having a structure as set forth in Formula I.

I

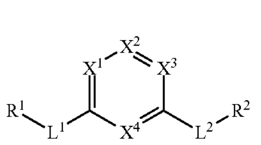

or a pharmaceutically acceptable salt thereof, wherein:

$X^1$ is N or C—$R^{x1}$;

$X^2$ is N or C—$R^{x2}$ $X^3$ is N or C—$R^{x3}$;

$X^4$ is N or C—$R^{x4}$;

provided that one or two of $X^1$, $X^2$, $X^3$ and $X^4$ is N;

each of RX, $R^{x2}$, $R^{x3}$, and $R^{x4}$ is independently selected from —R or —OR;

$L^1$ is selected from a covalent bond, —O—, —N(R)—, —C(O)N(R)—, —$S(O)_2$—, and —$S(O)_2N(R)$—;

$L^2$ is selected from a covalent bond, —O—, —N(R)—, —N(R)C(O)—, and —$N(R)S(O)_2$-;

$R^1$ is selected from halogen, CN, and —R;

$R^2$ is —R; and

R is selected from hydrogen or an optionally substituted group selected from $C_{1-6}$ aliphatic, phenyl, a 4- to 6-membered heterocyclic ring having 1-2 heteroatoms independently selected from nitrogen, oxygen, or sulfur, a 5- to 6-membered heteroaryl ring having 1-3 heteroatoms independently selected from nitrogen, oxygen, or sulfur, and an 8- to 10-membered heteroaryl ring having 1-3 heteroatoms independently selected from nitrogen, oxygen, or sulfur.

In some embodiments, provided compounds have structures of Formulae I-a, I-a-i, I-a-ii, I-a-iii, I-a-iv, I-a-v, I-b, I-b-i, I-b-ii, I-b-iii, I-b-iv, I-b-v, I-c, I-c-i, I-c-ii, I-c-iii, I-c-iv, and I-c-v, as set forth below.

In some embodiments, one or more compounds of Formula I is provided and/or utilized in a solid form (e.g., a crystal form or an amorphous form).

In some embodiments, the present disclosure provides compositions that comprise and/or deliver a compound of Formula I (e.g., in a form as described herein), a prodrug or active metabolite thereof.

In some embodiments, the present disclosure provides compositions that comprise and/or deliver a compound of Formula I. In some embodiments, such compositions are pharmaceutical compositions that include at least one pharmaceutically acceptable carrier, diluent or excipient.

In some embodiments, provided SARM1 inhibitors reduce or inhibit binding of NAD+ by SARM1. In some embodiments, provided SARM1 inhibitors bind to SARM1 within a pocket comprising one or more catalytic residues (e.g., a catalytic cleft of SARM1).

In some embodiments, provided compounds and/or compositions inhibit activity of SARM1. Alternatively or additionally, in some embodiments, provided compounds alleviate one or more attributes of neurodegeneration. In some embodiments, the present disclosure provides methods of treating a neurodegenerative disease or disorder associated with axonal degeneration.

In some embodiments, one or more compounds and/or compositions as described herein are useful, for example, in the practice of medicine. In some embodiments, one or more compounds and/or compositions as described herein are useful, for example, to treat, prevent, or ameliorate axonal degeneration (e.g., one or more features or characteristics thereof). In some embodiments, one or more compounds and/or compositions as described herein are useful, for example, to inhibit axonal degeneration, including axonal degeneration that results from reduction or depletion of NAD+. In some embodiments, one or more compounds and/or compositions as described herein are useful, for example, to prevent the axon distal to an axonal injury from degenerating.

In some embodiments, one or more compounds and/or compositions as described herein are useful, for example, to treat one or more neurodegenerative diseases, disorders or conditions selected from the group consisting of neuropathies or axonopathies. In some embodiments, one or more compounds and/or compositions as described herein are useful, for example, to treat a neuropathy or axonopathy associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration is selected from a list contained herein. In some embodiments, a neuropathy or axonopathy is associated with axonal degeneration, including, but not limited to, Parkinson's disease, non-Parkinson's disease, Alzheimer's disease, Herpes infection, diabetes, amyotrophic lateral sclerosis (ALS), a demyelinating disease, ischemia or stroke, chemical injury, thermal injury, and AIDS.

In some embodiments, subjects to which a compound or composition as described herein is administered may be or comprise subjects suffering from or susceptible to a neurodegenerative disease, disorder or condition. In some embodiments, a neurodegenerative disease, disorder or condition may be or comprise a traumatic neuronal injury. In some embodiments, a traumatic neuronal injury is blunt force trauma, a closed-head injury, an open head injury, exposure to a concussive and/or explosive force, a penetrating injury in or to the brain cavity or innervated region of the body. In some embodiments, a traumatic neuronal injury is a force which causes axons to deform, stretch, crush or sheer.

In some embodiments, provided methods comprise administering a compound described herein to a patient in need thereof. In some such embodiments, the patient is at risk of developing a condition characterized by axonal degeneration. In some embodiments, the patient has a condition characterized by axonal degeneration. In some embodiments, the patient has been diagnosed with a condition characterized by axonal degeneration.

In some embodiments, provided methods comprise administering a composition as described herein to a patient population in need thereof. In some embodiments, the population is drawn from individuals who engage in activities where the potential for traumatic neuronal injury is high. In some embodiments, the population is drawn from athletes who engage in contact sports or other high-risk activities In some embodiments, the patient is at risk of developing a neurodegenerative disorder. In some embodiments the patient is elderly. In some embodiments, the patient is known to have a genetic risk factor for neurodegeneration.

In certain embodiments, the present disclosure provides compounds that are useful, for example, as analytical tools, as probes in biological assays, or as therapeutic agents in accordance with the present disclosure. Compounds provided by this disclosure are also useful for the study of SARM1 function in biological and pathological phenomena and the comparative evaluation of new SARM1 activity inhibitors in vitro or in vivo.

In some embodiments, one or more compounds and/or compositions as described herein are useful, for example, as a method for inhibiting the degradation of neurons derived from a subject. In some embodiments, one or more compounds and/or compositions as described herein are useful for inhibiting the degeneration of a neuron, or a portion thereof, cultured in vitro. In some embodiments, one or more compounds and/or compositions as described herein are useful as stabilizing agents to promote in vitro neuronal survival.

BRIEF DESCRIPTION OF THE DRAWING

FIG. 1 illustrates the structure of the SARM1 protein.

DEFINITIONS

Aliphatic: The term "aliphatic" refers to a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle") refers to a monocyclic $C_3$-$C_8$ hydrocarbon or a bicyclic $C_7$-$C_{10}$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof.

Alkyl: The term "alkyl", used alone or as part of a larger moiety, refers to a saturated, optionally substituted straight or branched chain or cyclic hydrocarbon group having 1-12, 1-10, 1-8, 1-6, 1-4, 1-3, or 1-2 carbon atoms. The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

Alkylene: The term "alkylene" refers to a bivalent alkyl group. In some embodiments, "alkylene" is a bivalent straight or branched alkyl group. In some embodiments, an "alkylene chain" is a polymethylene group, i.e., $-(CH_2)_n-$, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3- to 7-membered ring. The substituents can be on the same or different atoms.

Alkenyl: The term "alkenyl", used alone or as part of a larger moiety, refers to an optionally substituted straight or branched chain or cyclic hydrocarbon group having at least one double bond and having 2-12, 2-10, 2-8, 2-6, 2-4, or 2-3 carbon atoms. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

Alkynyl: The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

Aryl: The term "aryl" refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic carbocyclic or heterocyclic rings, such as indanyl, phthalimidyl, naphthimidyl, phenanthridinyl, tetrahydronaphthyl, imidazolidinyl, imidazolidin-2-one, and the like.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchioalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or proteins extracted from a sample or obtained by subjecting a primary sample to techniques such as amplification or reverse transcription of mRNA, isolation and/or purification of certain components, etc.

Biomarker: The term "biomarker" is used herein to refer to a to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be or comprise an entity of any chemical class, and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is detected outside of cells (e.g., is secreted or is otherwise generated or present outside of cells, e.g., in a body fluid such as blood, urine, tears, saliva, cerebrospinal fluid, etc. In some embodiments, a biomarker may be or comprise a genetic or epigenetic signature. In some embodiments, a biomarker may be or comprise a gene expression signature.

In some embodiments, a biomarker may be or comprise a marker for neurodegeneration, or for likelihood that a neurodegenerative disease, disorder or condition may develop, occur, or reoccur. In some embodiments, a biomarker may be or comprise a marker of neurodegeneration a therapeutic outcome, or likelihood thereof. Thus, in some embodiments, a biomarker is predictive, in some embodiments, a biomarker is prognostic, in some embodiments, a biomarker is diagnostic, of a neurodegenerative disease, disorder or condition. In some embodiments changes in biomarker levels can be detected via cerebral spinal fluid (CSF), plasma and/or serum.

In some embodiments, neurodegeneration may be assessed, for example, by detecting an increase and/or decrease in the concentration of neurofilament protein light (NF-L) and/or neurofilament protein heavy (NF—H) contained the cerebral spinal fluid of a subject. In some embodiments, the incidence and/or progression of neurodegeneration can be assessed via positron emission tomography (PET) with a synaptic vesicle glycoprotein 2a (SV2A) ligand. In some embodiments, a detectable change in constitutive NAD and/or cADPR levels in neurons can be used to assess neurodegeneration.

In some embodiments, a detectable change in one or more neurodegeneration associated proteins in a subject, relative to a healthy reference population can be used as a biomarker of neurodegeneration. Such proteins include, but are not limited to, albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, an increase in cytokines and/or chemokines, including, but not limited to, Ccl2, Ccl7, Ccl12, Csf1, and/or Il6, can be used as a biomarker of neurodegeneration.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Heteroaryl: The terms "heteroaryl" and "heteroar-", used alone or as part of a larger moiety, e.g., "heteroaralkyl", or "heteroaralkoxy", refer to groups having 5 to 10 ring atoms, preferably 5, 6, 9, or 10 ring atoms; having 6, 10, or 14 π□electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

Heterocycle: As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen"

includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $NR^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings (e.g., 2,3-dihydrobenzofuran, 2,3-dihydrobenzo[b][1,4]dioxine, etc.).

Inhibitory agent: As used herein, the term "inhibitory agent" refers to an entity, condition, or event whose presence, level, or degree correlates with decreased level or activity of a target. In some embodiments, an inhibitory agent may act directly (in which case it exerts its influence directly upon its target, for example, by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc.).

Neurodegeneration: As used herein, the term "neurodegeneration" refers to a reduction in one or more features, structures, or characteristics of a neuron or neuronal tissue. In some embodiments, neurodegeneration is observed as a pathological reduction in an organism. Those skilled in the art will appreciate that neurodegeneration is associated with certain diseases, disorders and conditions, including those that affect humans. In some embodiments, neurodegeneration may be transient (e.g., as sometimes occurs in association with certain infections and/or chemical or mechanical disruptions); in some embodiments, neurodegeneration may be chronic and/or progressive (e.g., as is often associated with certain diseases, disorders or conditions such as, but not limited to, Parkinson's disease, amyotrophic lateral sclerosis, multiple sclerosis, Huntington disease, or Alzheimer's disease). In some embodiments, neurodegeneration may be assessed, for example, by detecting in a subject an increase in a biomarker associated with neurodegeneration. In some embodiments, neurodegeneration may be assessed, for example, by detecting in a subject a decrease in a biomarker associated with neurodegeneration. Alternatively or additionally, in some embodiments, neurodegeneration may be assessed by magnetic resonance imaging (MRI), biomarkers containing cerebral spinal fluid, or other biomarkers observed in patients. In some embodiments, neurodegeneration is defined as a score of below 24 on the mini-mental state examination. In some embodiments, neurodegeneration refers to loss of synapses. In some embodiments, neurodegeneration refers to a reduction in neural tissue relating to a traumatic injury (e.g. exposure to an external force which disrupts the integrity of the neural tissue). In some embodiments, neurodegeneration refers to a reduction in peripheral neural tissue. In some embodiments, neurodegeneration refers to a reduction in central nervous tissue.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Partially Unsaturated: As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prevent or prevention: As used herein, the terms "prevent" or "prevention", when used in connection with the occurrence of a disease, disorder, and/or condition, refer to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments, specificity is evaluated relative to that of a reference non-specific binding agent. In some embodiments, the agent or entity does not detectably bind to the competing alternative target under conditions of binding to its target entity. In some embodiments, a binding agent binds with higher on-rate, lower off-rate, increased affinity, decreased dissociation, and/or increased stability to its target entity as compared with the competing alternative target(s).

Subject: As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substituted or optionally substituted: As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.

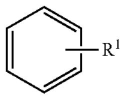

refers to at least

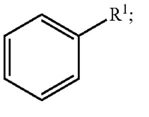 and 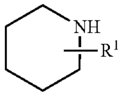

refers to at least

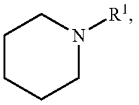 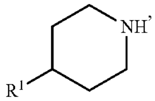 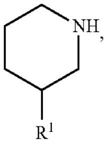 or 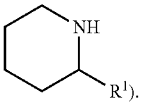

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; $—CN$; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)(NH)R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5- to 6-membered heteroaryl ring), a 5- to 6-membered saturated, partially unsaturated, or aryl ring having 0-4 heteroatoms independently selected from nitrogen, oxygen, or sulfur, or an 8- to 10-membered bicyclic aryl ring having 0-4 heteroatoms independently selected from nitrogen, oxygen, or sulfur, or, notwithstanding the definition above, two independent occurrences of $R^\circ$, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; $—O$(halo$R^\bullet$), $—CN$, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 3- to 6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$ ("oxo"), $=S$, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, -(halo$R^\bullet$), $—OH$, $—OR^\bullet$, $—O$(halo$R^\bullet$), $—CN$, $—C(O)OH$, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(RT)S(O)_2R^\dagger$; wherein each $R^\dagger$ is independently hydrogen, $C_{1-6}$ aliphatic which may be substituted as defined below, unsubstituted $—OPh$, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5- to 6-membered saturated, partially unsaturated, or aryl ring having 0-4 heteroatoms independently selected from nitrogen, oxygen, or sulfur.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition.

DETAILED DESCRIPTION OF CERTAIN EMBODIMENTS

Programmed Axonal Degeneration and SARM1

Axonal degeneration is a major pathological feature of neurological diseases such as, but not limited to, Alzheimer's disease, Parkinson's disease, ALS, multiple sclerosis, diabetic peripheral neuropathy, chemotherapy-induced peripheral neuropathy, inherited neuropathy, traumatic brain injury, and/or glaucoma. Damaged or unhealthy axons are eliminated via an intrinsic self-destruction program that is distinct from traditional cellular death pathways like apoptosis known as Wallerian degeneration. (Gerdts, J., et al., *Neuron,* 2016, 89, 449-460; Whitmore, A. V. et al., *Cell Death Differ.,* 2003, 10, 260-261). In Wallerian degeneration, a peripheral nerve undergoes selective breakdown of the axon segment distal to an injury, whereas the proximal axon segment and cell body remain intact. This degeneration is characterized, first, by a depletion of nicotinamide mononucleotide adenyltransferase (NMNAT), followed by nicotinamide adenine dinucleotide (NAD+) loss, adenosine triphosphate (ATP) loss, neurofilament proteolysis, and finally axonal degradation approximately 8 to 24 hours following injury. (Gerdts, J., et al., *Neuron,* 2016, 89, 449-460).

NAD+ is a ubiquitous metabolite with critical roles in energy metabolism and cell signaling (Belenkey et al., *Trends Biochem.,* 2007, 32, 12-19; Chiarugi et al., *Nat. Rev. Cancer,* 2012, 12, 741-752). The homeostatic regulation of NAD+ levels is also responsible for maintaining axonal stability and integrity. Accordingly, manipulations that increase axonal localization of NMNAT1 confer axonal protection (Babetto et al., *Cell Rep.,* 2010, 3, 1422-1429; Sasaki et al., *J. Neurosci.,* 2009).

In a genome-wide RNAi screen in primary mouse neurons, Sterile Alpha and TIR motif-containing 1 (SARM1) was identified, in which knockdown of SARM1 led to long-lasting protection of sensory neurons against injury-induced axon degeneration (Gerdts et al., J Neurosci, 2013, 33, 13569-13580). SARM1 belongs to the family of cytosolic adaptor proteins, but is unique among its members because it is the most evolutionary ancient adaptor, paradoxically inhibits TLR signaling, and has been identified as the central executioner of the injury-induced axon death pathway (O'Neill, L. A. & Bowie, A. G., *Nat. Rev. Immunol.,* 2007, 7, 353-364; Osterloh, J. M., et al., *Science,* 2012, 337, 481-484; Gerdts, J., et al., *J. Neurosci.* 33, 2013, 13569-13580). Activation of SARM1 via axonal injury or forced dimerization of SARM1-TIR domains promotes rapid and catastrophic depletion of Nicotinamide Adenine Dinucleotide (NAD+), followed soon after by axonal degradation, thus highlighting the central role of NAD+ homeostasis in axonal integrity. (Gerdts, J., et al., *Science,* 2015, 348, 453-457). SARM1 is required for this injury-induced NAD+ depletion both in vitro and in vivo and SARM1 activation triggers axon degeneration locally via NAD(+) destruction (Gerdts et al., et al., *Science,* 2015 348, 452-457; Sasaki et al., J. Biol. Chem. 2015, 290, 17228-17238; both of which are hereby incorporated by reference in their entireties).

From genetic loss-of-function studies it is clear that SARM1 serves as the central executioner of the axonal degeneration pathway following an injury. Genetic knockout of SARM1 allows for preservation of axons for up to 14 days after nerve transection (Osterloh, J. M., et al., *Science,* 2012, 337, 481-484; Gerdts, J., et al., *J. Neurosci.,* 2013, 33, 13569-13580) and also improves functional outcomes in mice after traumatic brain injury (Henninger, N. et al., *Brain* 139, 2016, 1094-1105). In addition to the role of SARM1 in direct axonal injury, SARM1 is also required for axonal degeneration observed in chemotherapy-induced peripheral neuropathy. Loss of SARM1 blocks chemotherapy-induced peripheral neuropathy, both inhibiting axonal degeneration and heightened pain sensitivity that develops after chemotherapeutic vincristine treatment (Geisler et al, *Brain,* 2016, 139, 3092-3108).

SARM1 contains multiple conserved motifs including SAM domains, ARM/HEAT motifs and a TIR domain (FIG. 1) that mediate oligomerization and protein-protein interactions (O'Neill, L. A. & Bowie, A. G., *Nat. Rev. Immunol.,* 2007, 7, 353-364; Tewari, R., et al., *Trends Cell Biol.,* 2010, 20, 470-481; Qiao, F. & Bowie, J. U., *Sci. STKE* 2005, re7, 2005). TIR domains are commonly found in signaling proteins functioning in innate immunity pathways where they serve as scaffolds for protein complexes (O'Neill, L. A. & Bowie, A. G., *Nat. Rev. Immunol.,* 2007, 7, 353-364). Interestingly, dimerization of SARM1-TIR domains is sufficient to induce axonal degeneration and to rapidly trigger degradation of NAD+ by acting as the NAD+ cleaving enzyme (Milbrandt et al., WO 2018/057989; Gerdts, J., et al., *Science,* 2015, 348, 453-457). Given the central role of SARM1 in the axonal-degeneration pathway and its identified NADase activity, efforts have been undertaken to identify agents that can regulate SARM1, and potentially act as useful therapeutic agents, for example, to protect against neurodegenerative diseases including peripheral neuropathy, traumatic brain injury, and/or neurodegenerative diseases.

Among other things, the present disclosure provides certain compounds and/or compositions that act as SARM1 inhibitory agents (e.g., as SARM1 inhibitory agents), and technologies relating thereto.

Compounds

In some embodiments, the present disclosure provides a compound of Formula I:

I

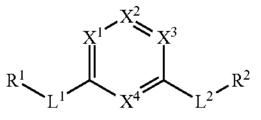

or a pharmaceutically acceptable salt thereof, wherein:

$X^1$ is N or C—$R^{x1}$;

$X^2$ is N or C—$R^{x2}$;

$X^3$ is N or C—$R^{x3}$;

$X^4$ is N or C—$R^{x4}$;

provided that one or two of $X^1$, $X^2$, $X^3$ and $X^4$ is N;

each of $R^{x1}$, $R^{x2}$, $R^{x3}$, and $R^{x4}$ is independently selected from —R or —OR;

$L^1$ is selected from a covalent bond, —O—, —N(R)—, —C(O)N(R)—, —$S(O)_2$—, and —$S(O)_2N(R)$—;

$L^2$ is selected from a covalent bond, —O—, —N(R)—, —N(R)C(O)—, and —$N(R)S(O)_2$-;

$R^1$ is selected from halogen, CN, and —R;

$R^2$ is —R; and

R is selected from hydrogen or an optionally substituted group selected from $C_{1-6}$ aliphatic, phenyl, a 4- to 6-membered heterocyclic ring having 1-2 heteroatoms independently selected from nitrogen, oxygen, or sulfur, a 5- to 6-membered heteroaryl ring having 1-3 heteroatoms independently selected from nitrogen, oxygen, or sulfur, and an 8- to 10-membered heteroaryl ring having 1-3 heteroatoms independently selected from nitrogen, oxygen, or sulfur.

As defined generally above, $X^1$ is N or C—$R^{x1}$. In some embodiments, $X^1$ is N. In some embodiments, $X^1$ is C—$R^{x1}$. In some embodiments, $X^1$ is C—$R^{x1}$ and one of $X^2$, $X^3$ and $X^4$ is N. In some embodiments, $X^1$ is C—$R^{x1}$ and two of $X^2$, $X^3$ and $X^4$ is N.

As defined generally above, $X^2$ is N or C—$R^{x2}$. In some embodiments, $X^2$ is N. In some embodiments, $X^2$ is C—$R^{x2}$. In some embodiments, $X^2$ is C—$R^{x2}$ and one of $X^1$, $X^3$ and $X^4$ is N. In some embodiments, $X^2$ is C—$R^{x2}$ and two of $X^1$, $X^3$ and $X^4$ is N.

As defined generally above, $X^3$ is N or C—$R^{x3}$. In some embodiments, $X^3$ is N. In some embodiments, $X^3$ is C—$R^{x3}$. In some embodiments, $X^3$ is C—$R^{x3}$ and one of $X^1$, $X^2$ and $X^4$ is N. In some embodiments, $X^3$ is C—$R^{x3}$ and two of $X^1$, $X^2$ and $X^4$ is N.

As defined generally above, $X^4$ is N or C—$R^{x4}$. In some embodiments, $X^4$ is N. In some embodiments, $X^4$ is C—$R^{x4}$. In some embodiments, $X^4$ is C—$R^{x4}$ and one of $X^1$, $X^2$ and $X^3$ is N. In some embodiments, $X^4$ is C—$R^{x4}$ and two of $X^1$, $X^2$ and $X^3$ is N.

As defined generally above, one or two of $X^1$, $X^2$, $X^3$ and $X^4$ is N. Accordingly, it will be appreciated that, in compounds of Formula I, at least one, but no more than two, of $X^1$, $X^2$, $X^3$ and $X^4$ is N.

As defined generally above, each of $R^{x1}$, $R^{x2}$, $R^{x3}$, and $R^{x4}$ is independently selected from —R or —OR.

As defined generally above, $R^{x1}$ is independently selected from —R or —OR. In some embodiments, $R^{x1}$ is hydrogen. In some embodiments, $R^{x1}$ is optionally substituted $C_{1-6}$ aliphatic. In some embodiments, $R^{x1}$ is optionally substituted $C_{1-3}$ aliphatic. In some embodiments, $R^{x1}$ is —$CH_3$, —$CH_2CH_3$ or —$CH(CH_3)_2$. In some embodiments, $R^{x1}$ is —OR. In some embodiments, $R^{x1}$ is —OH. In some embodiments, $R^{x1}$ is —$OCH_3$. In some embodiments, $R^{x1}$ is

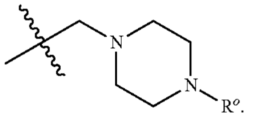

As defined generally above, $R^{x2}$ is independently selected from —R or —OR. In some embodiments, $R^{x2}$ is hydrogen. In some embodiments, $R^{x2}$ is optionally substituted $C_{1-6}$ aliphatic. In some embodiments, $R^{x2}$ is optionally substituted $C_{1-3}$ aliphatic. In some embodiments, $R^{x2}$ is —$CH_3$, —$CH_2CH_3$ or —$CH(CH_3)_2$. In some embodiments, $R^{x2}$ is —OR. In some embodiments, $R^{x2}$ is —OH. In some embodiments, $R^{x2}$ is —$OCH_3$.

As defined generally above, $R^{x3}$ is independently selected from —R or —OR. In some embodiments, $R^{x3}$ is hydrogen. In some embodiments, $R^{x3}$ is optionally substituted $C_{1-6}$ aliphatic. In some embodiments, $R^{x3}$ is optionally substituted $C_{1-3}$ aliphatic. In some embodiments, $R^{x3}$ is —$CH_3$, —$CH_2CH_3$ or —$CH(CH_3)_2$. In some embodiments, $R^{x3}$ is —OR. In some embodiments, $R^{x3}$ is —OH. In some embodiments, $R^{x3}$ is —$OCH_3$.

As defined generally above, $R^{x4}$ is independently selected from —R or —OR. In some embodiments, $R^{x4}$ is hydrogen. In some embodiments, $R^{x4}$ is optionally substituted $C_{1-6}$ aliphatic. In some embodiments, $R^{x4}$ is optionally substituted $C_{1-3}$ aliphatic. In some embodiments, $R^{x4}$ is —$CH_3$, —$CH_2CH_3$ or —$CH(CH_3)_2$. In some embodiments, $R^{x4}$ is —OR. In some embodiments, $R^{x4}$ is —OH. In some embodiments, $R^{x4}$ is —$OCH_3$.

It will be appreciated that compounds wherein: $R^{x1}$ is —OH and $X^2$ is N; or $R^{x2}$ is —OH and $X^1$ or $X^3$ is N; or $R^{x3}$ is —OH and $X^2$ is N; or $X^1$ is N and -$L^1$-$R^1$ is —OH; or $X^3$ is N and -$L^2$-$R^2$ is —OH can exist in two tautomeric forms, for example:

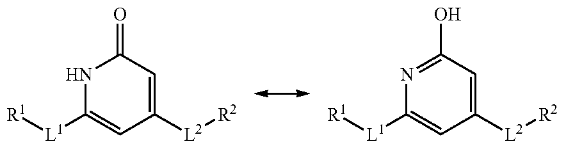

Similarly, compounds wherein: $X^1$ and $X^2$ is N and $R^{x3}$ is OH; or $X^1$ and $X^2$ is N and -$L^1$-$R^1$ is OH; or $X^2$ and $X^3$ is N and -$L^2$-$R^2$ is OH; or $X^2$ and $X^3$ is N and $R^{x1}$ is OH can exist in two tautomeric forms, for example:

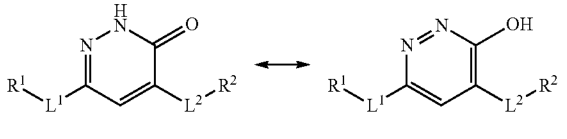

The present disclosure contemplates and encompasses all tautomeric forms of the compounds described herein. In some embodiments, a compound of Formula I is depicted in pyridin-2(1H)-one or pyridazin-3(2H)-one tautomeric form. In some embodiments, a compound of Formula I is depicted in pyridin-2-ol or pyridazin-3-ol tautomeric form.

As defined generally above, $L^1$ is selected from a covalent bond, —O—, —N(R)—, —C(O)N(R)—, $—S(O)_2—$, and $—S(O)_2N(R)—$. In some embodiments, $L^1$ is a covalent bond. In some embodiments, $L^1$ is —C(O)N(R)—. In some such embodiments, $L^1$ is —C(O)NH—. In some embodiments, $L^1$ is $—C(O)N(CH_3)—$. In some embodiments, $L^1$ is $—S(O)_2$-. In some embodiments, $L^1$ is $—S(O)_2N(R)—$. In some such embodiments, $L^1$ is $—S(O)_2NH—$. In some embodiments, $L^1$ is $—S(O)_2N(CH_3)—$.

As defined generally above, $L^2$ is selected from a covalent bond, —O—, —N(R)—, —N(R)C(O)—, and $—N(R)S(O)_2$-. In some embodiments, $L^2$ is a covalent bond. In some embodiments, $L^2$ is —O—. In some embodiments, $L^2$ is —N(R)—. In some embodiments, $L^2$ is —NH—. In some embodiments, $L^2$ is $—N(CH_3)—$. In some embodiments, $L^2$ is —N(R)C(O)—. In some such embodiments, $L^2$ is —NHC(O)—. In some embodiments, $L^2$ is $—N(CH_3)C(O)—$. In some embodiments, $L^2$ is $—N(R)S(O)_2$-. In some such embodiments, $L^2$ is $—NHS(O)_2$-. In some embodiments, $L^2$ is $—N(CH_3)S(O)_2$-.

As defined generally above, $R^1$ is selected from halogen, CN, and —R. In some embodiments, $R^1$ is halogen. In some such embodiments, $R^1$ is bromo. In some embodiments, $R^1$ is chloro. In some embodiments, $R^1$ is CN.

In some embodiments, $R^1$ is —R. In some embodiments, $R^1$ is H. In some embodiments, $R^1$ is an optionally substituted group selected from $C_{1-6}$ aliphatic, phenyl, a 4- to 6-membered heterocyclic ring having 1-2 heteroatoms independently selected from nitrogen, oxygen, or sulfur, a 5- to 6-membered heteroaryl ring having 1-3 heteroatoms independently selected from nitrogen, oxygen, or sulfur, and an 8- to 10-membered heteroaryl ring having 1-3 heteroatoms independently selected from nitrogen, oxygen, or sulfur.

In some embodiments, $R^1$ is optionally substituted $C_{1-6}$ aliphatic. In some embodiments, $R^1$ is optionally substituted $C_{1-2}$ aliphatic. In some embodiments, $R^1$ is optionally substituted $C_{3-4}$ aliphatic. In some embodiments, $R^1$ is optionally substituted $C_{5-6}$ aliphatic. In some embodiments, $R^1$ is $—CH_3$. In some embodiments, $R^1$ is $—CH_2CH_3$. In some embodiments, $R^1$ is $—CH_2CH_2CH_3$ or $—CH(CH_3)_2$. In some embodiments, $R^1$ is $—CH_2CH(CH_3)_2$. In some embodiments, $R^1$ is $—(CH_2)_4CH_3$. In some embodiments, $R^1$ is $C_{1-6}$ aliphatic optionally substituted with a group selected from halogen, $—(CH_2)_{0-4}R^\circ$, $—(CH_2)_{0-4}OR^\circ$, $—(CH_2)_{0-4}N(R^\circ)_2$, or $—(CH_2)_{0-4}N(R^\circ)CO_2R^\circ$. In some embodiments, $R^1$ is $—CH_2—R^\circ$, $—CH_2—OR^\circ$, $—CH_2—N(R^\circ)_2$, or $—CH_2—N(R^\circ)CO_2R^\circ$. In some embodiments, $R^1$ is $—CH_2CH_2—R^\circ$, $—CH_2CH_2—OR^\circ$, $—CH_2CH_2—N(R^\circ)_2$, or $—CH_2CH_2—N(R^\circ)CO_2R^\circ$. In some embodiments, $R^1$ is $—(CH_2)_3—R^\circ$, $—(CH_2)_3—OR^\circ$, $—(CH_2)_3—N(R^\circ)_2$, or $—(CH_2)_3—N(R^\circ)CO_2R^\circ$. In some embodiments, $R^1$ is $—(CH_2)_4—R^\circ$, $—(CH_2)_4—OR^\circ$, $—(CH_2)_4—N(R^\circ)_2$, or $—(CH_2)_4—N(R^\circ)CO_2R^\circ$.

In some embodiments, $R^1$ is $C_{1-6}$ aliphatic optionally substituted with halogen. In some embodiments, $R^1$ is $C_{1-2}$ aliphatic optionally substituted with halogen. In some embodiments, $R^1$ is $C_{1-6}$ aliphatic optionally substituted with $—R^\circ$, wherein $R^\circ$ is selected from:

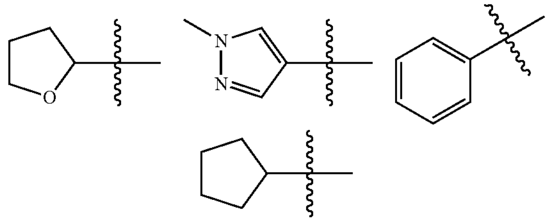

In some embodiments, $R^1$ is an optionally substituted phenyl. In some embodiments, $R^1$ is an optionally substituted 5- to 6-membered heteroaryl ring having 1-3 heteroatoms independently selected from nitrogen, oxygen, or sulfur. In some embodiments, $R^1$ is an optionally substituted 5-membered heteroaryl ring having 1-3 heteroatoms independently selected from nitrogen, oxygen, or sulfur. In some embodiments, $R^1$ is an optionally substituted

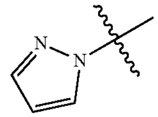

.

In some embodiments, $R^1$ is selected from hydrogen, chloro, bromo, —CN, $—CH_3$, $—CH_2F$, $—CH_2CH_3$, $—CH_2CF_3$, $—CH_2CHF_2$, $—CH_2CH_2CH_3$, $—CH(CH_3)_2$, $—(CH_2)_4CH_3$, $—CH_2CH(CH_3)_2$, phenyl, or a group selected from

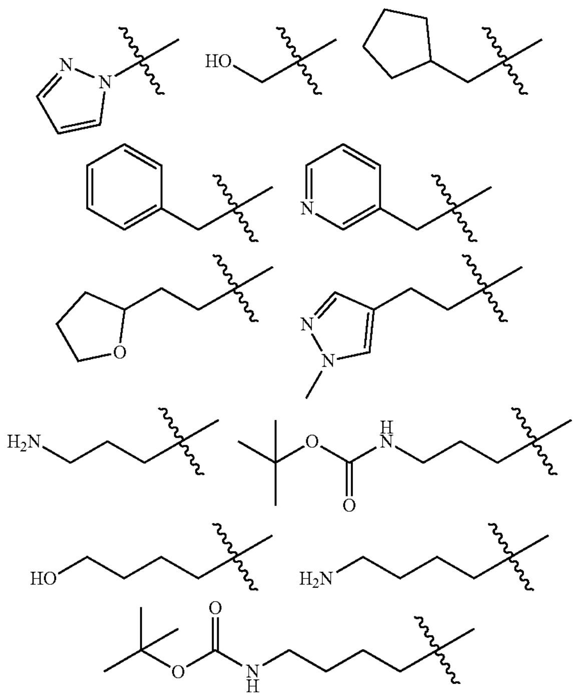

As defined generally above, $R^2$ is —R. In some embodiments, $R^2$ is H. In some embodiments, $R^2$ is an optionally substituted group selected from $C_{1-6}$ aliphatic, phenyl, a 4- to 6-membered heterocyclic ring having 1-2 heteroatoms independently selected from nitrogen, oxygen, or sulfur, a 5- to 6-membered heteroaryl ring having 1-3 heteroatoms independently selected from nitrogen, oxygen, or sulfur, and an 8- to 10-membered heteroaryl ring having 1-3 heteroatoms independently selected from nitrogen, oxygen, or sulfur.

In some embodiments, $R^2$ is optionally substituted $C_{1-6}$ aliphatic. In some embodiments, $R^2$ is optionally substituted $C_{1-2}$ aliphatic. In some embodiments, $R^2$ is $-CH_3$. In some embodiments, $R^2$ is $-CH_2CH_3$.

In some embodiments, $R^2$ is $C_{1-6}$ aliphatic optionally substituted with halogen. In some embodiments, $R^2$ is $C_{1-2}$ aliphatic optionally substituted with halogen. In some embodiments, $R^2$ is $C_{1-6}$ aliphatic optionally substituted with $-R^{\circ}$, wherein $R^{\circ}$ is selected from:

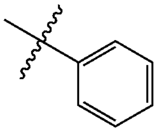 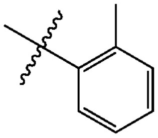 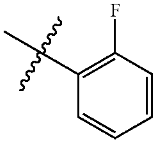

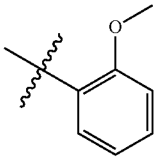 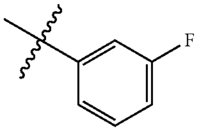

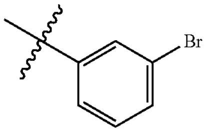 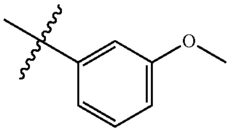

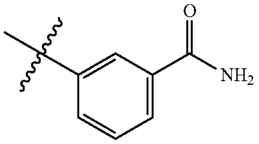 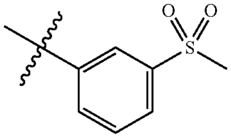

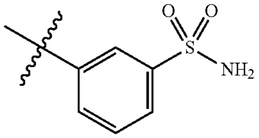 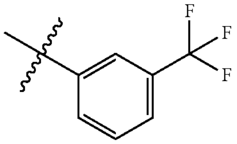

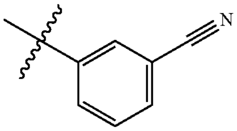 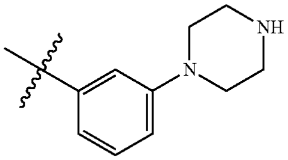

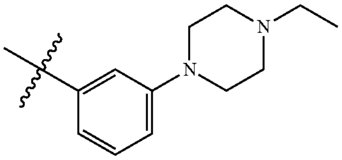

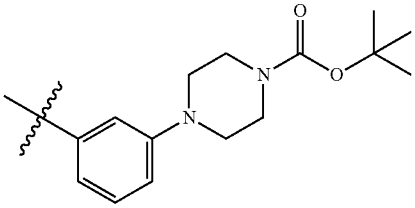

-continued

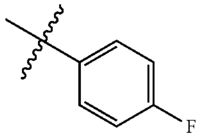 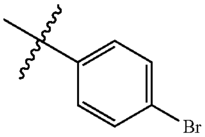

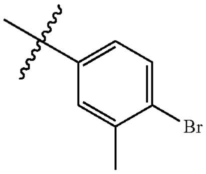 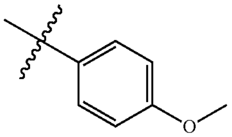

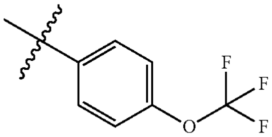 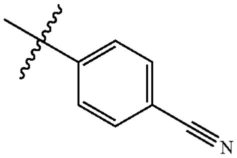

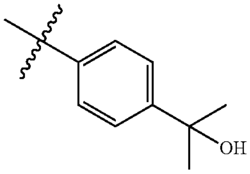 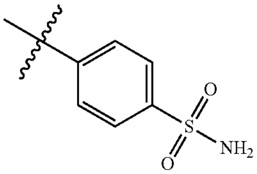

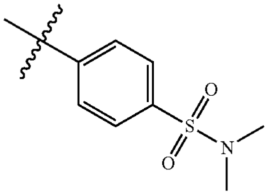 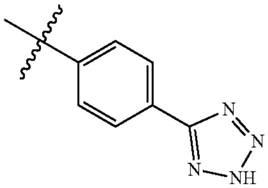

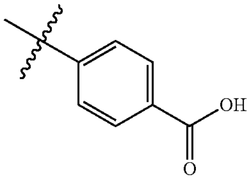 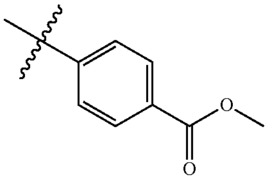

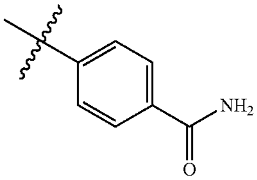 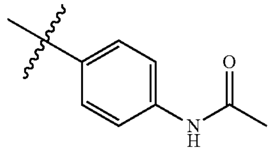

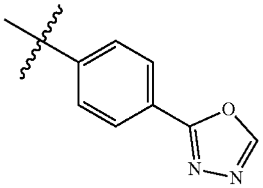

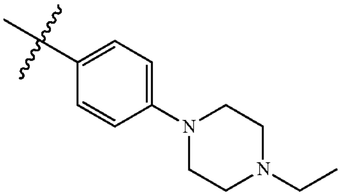 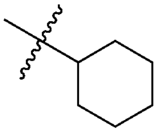

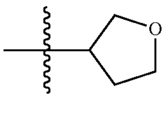 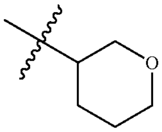 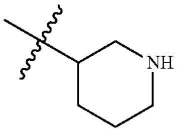

-continued
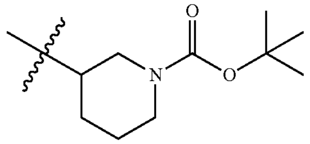
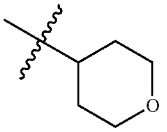
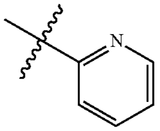
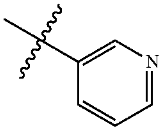
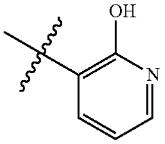
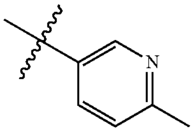
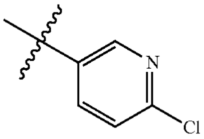
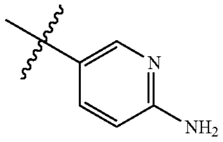
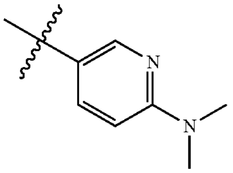
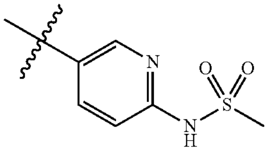
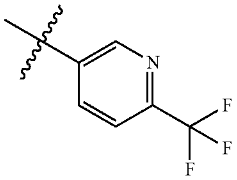
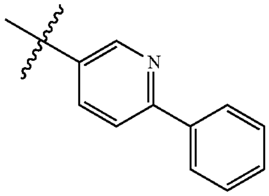
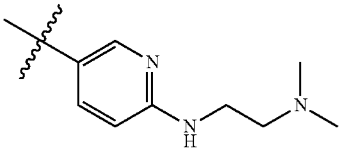
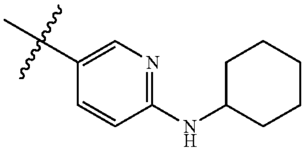
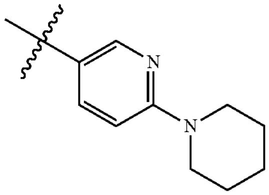
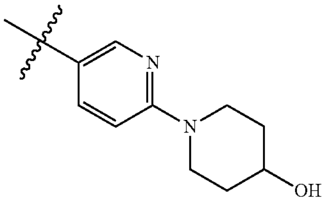
-continued
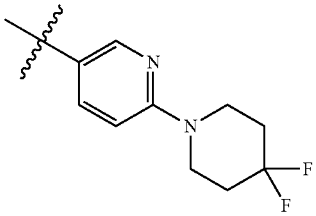
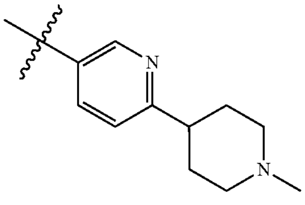
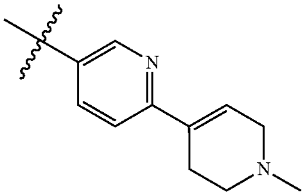
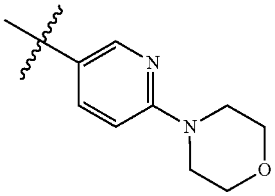
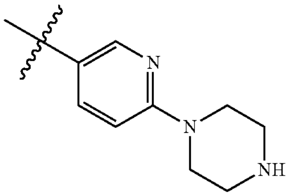
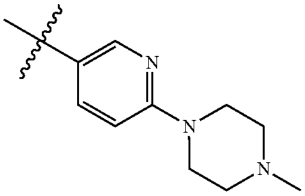
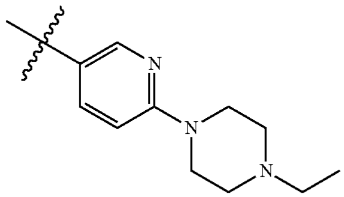
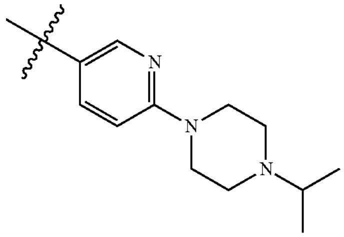
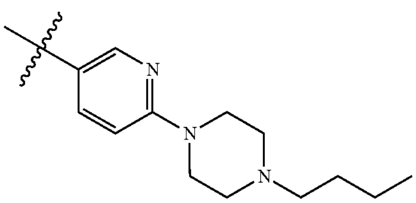

-continued
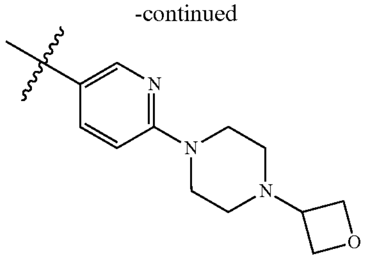
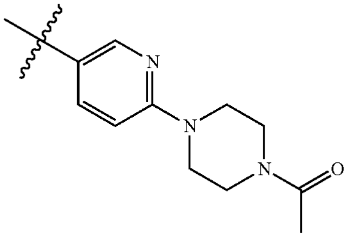
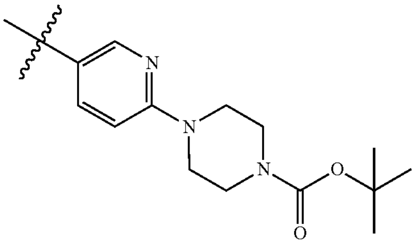
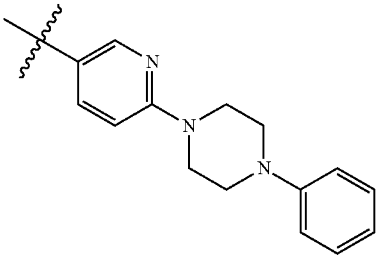
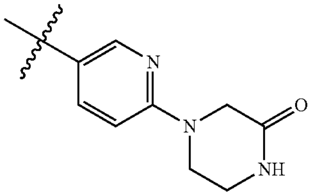
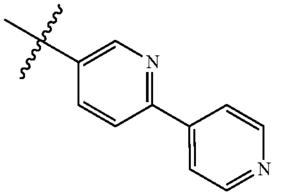
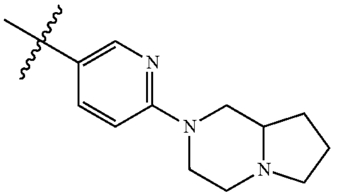
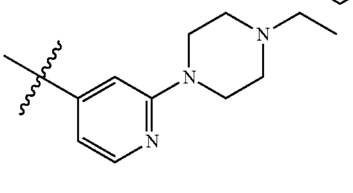
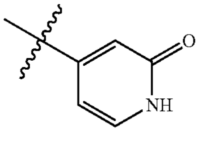
-continued
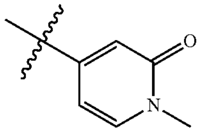
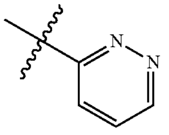
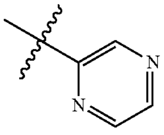
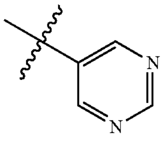
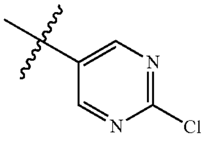
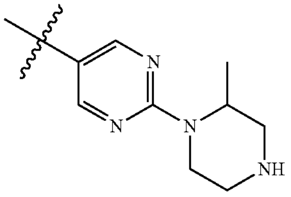
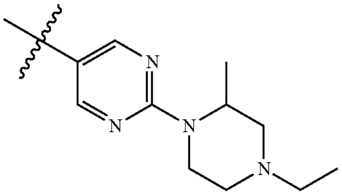
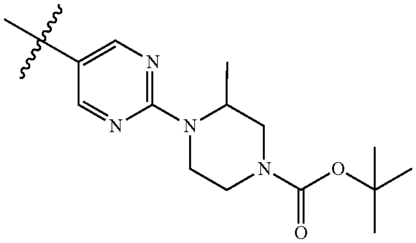
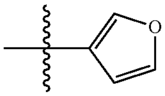
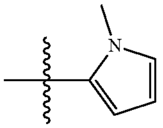
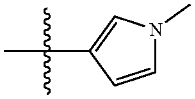
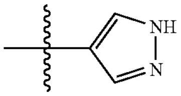
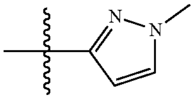
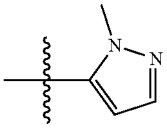
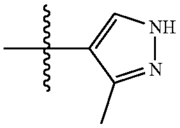
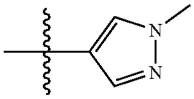
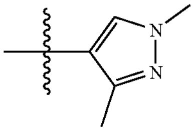
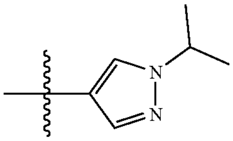
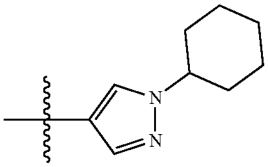
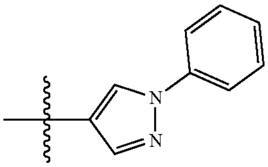
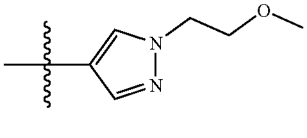

-continued
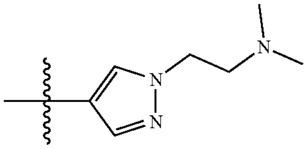
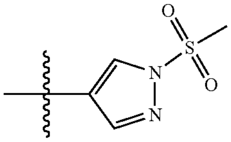
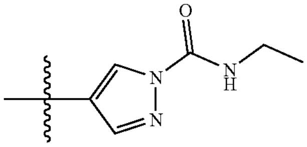
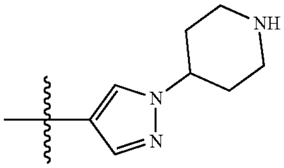
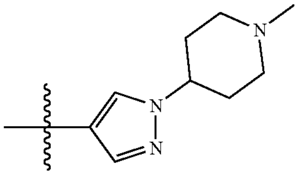
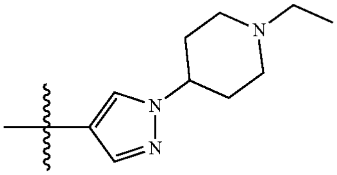
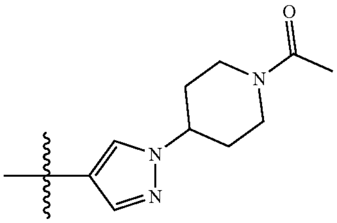
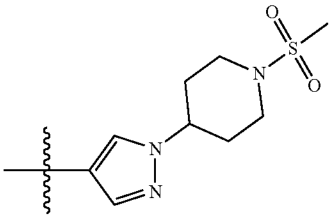
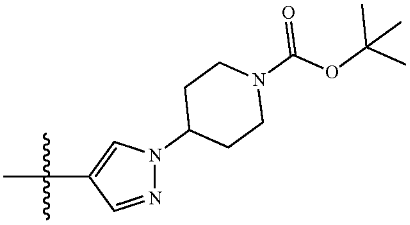
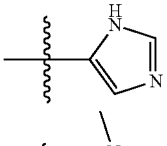
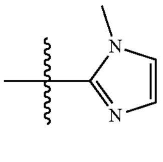
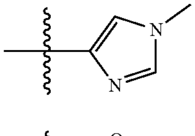
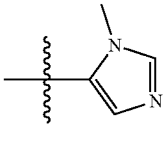
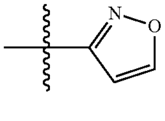
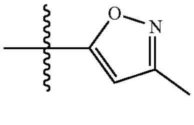
-continued
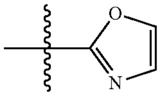
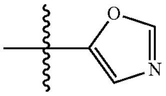
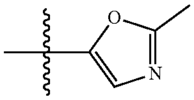
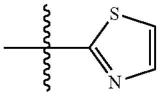
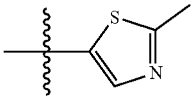
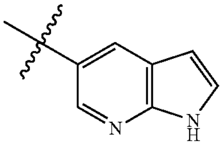
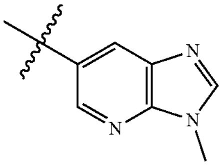
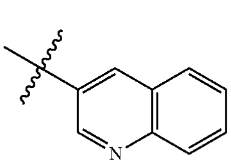
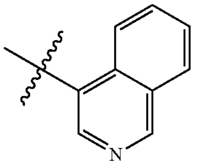
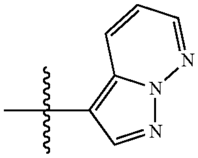
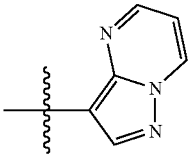
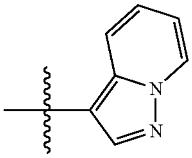
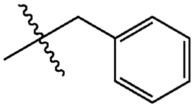
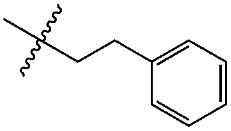
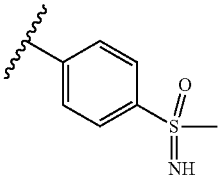
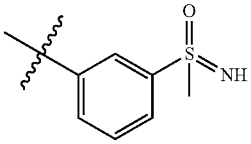
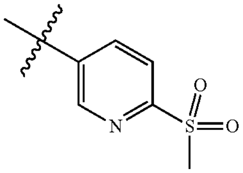
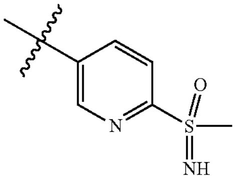
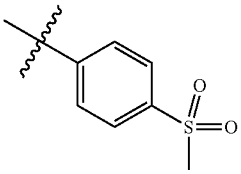
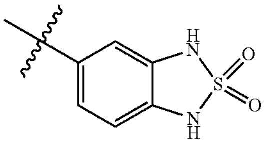
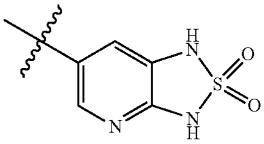
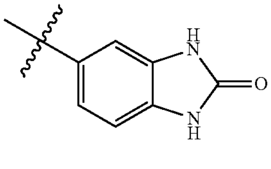
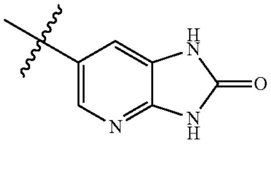

-continued

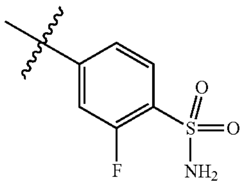 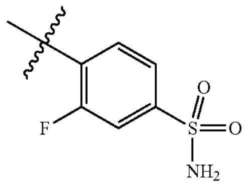

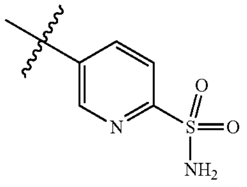

In some such embodiments, R is not

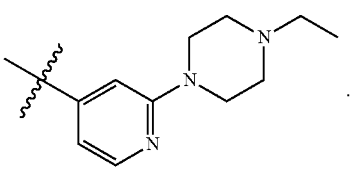 [SMILES: *c1ccnc(N2CCN(CC)CC2)c1]

In some embodiments, $R^2$ is an optionally substituted phenyl.

In some embodiments, $R^2$ is an optionally substituted 5- to 6-membered heteroaryl ring having 1-3 heteroatoms independently selected from nitrogen, oxygen, or sulfur. In some embodiments, $R^2$ is an optionally substituted 6-membered heteroaryl ring having 1-3 nitrogen atoms. In some embodiments, $R^2$ is an optionally substituted 6-membered heteroaryl ring having 1-2 nitrogen atoms. In some embodiments, $R^2$ is an optionally substituted group selected from

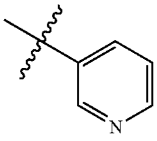 and 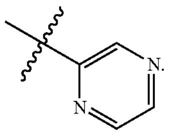

In some embodiments, $R^2$ is an optionally substituted 8- to 10-membered heteroaryl ring having 1-3 heteroatoms independently selected from nitrogen, oxygen, or sulfur. In some embodiments, $R^2$ is an optionally substituted 10-membered heteroaryl ring having 1-3 nitrogen atoms. In some embodiments, $R^2$ is optionally substituted

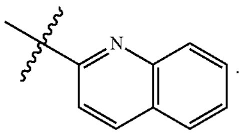 [SMILES: *c1ccc2ccccc2n1]

In some such embodiments, $R^2$ is

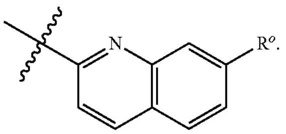

In some embodiments, $R^2$ is an optionally substituted 4- to 6-membered heterocyclic ring having 1-2 heteroatoms independently selected from nitrogen, oxygen, or sulfur. In some embodiments, $R^2$ is an optionally substituted 6-membered heterocyclic ring having 1-2 heteroatoms independently selected from nitrogen, oxygen, or sulfur. In some embodiments, $R^2$ is an optionally substituted 6-membered heterocyclic ring having 1-2 heteroatoms independently selected from nitrogen, oxygen, or sulfur. In some embodiments, $R^2$ is

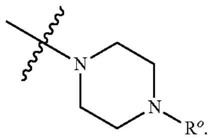

In some embodiments, $R^2$ is not

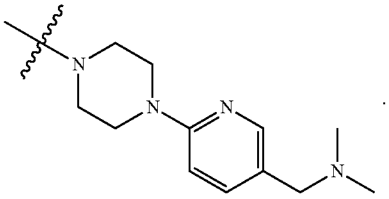 [SMILES: *N1CCN(c2ccc(CN(C)C)cn2)CC1]

In some embodiments, $R^2$ is selected from the group consisting of hydrogen, —$CH_3$, phenyl,

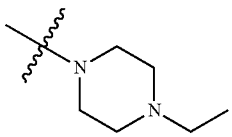

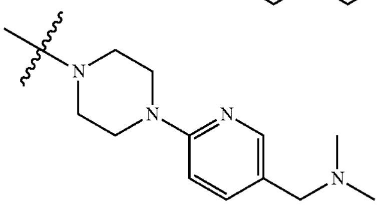 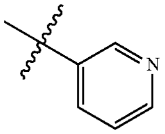

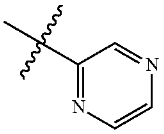 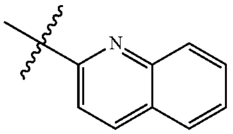

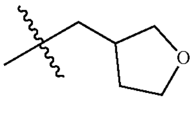 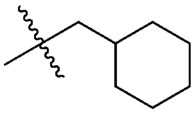

-continued
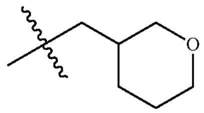
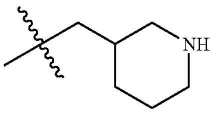
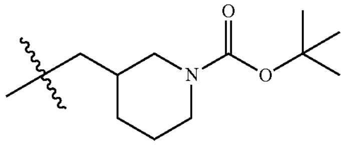
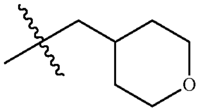
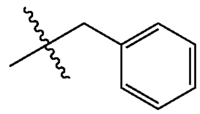
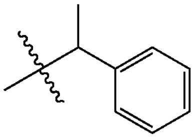
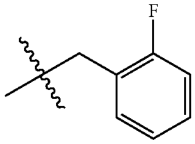
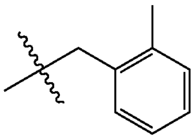
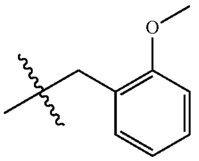
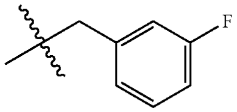
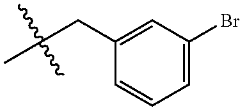
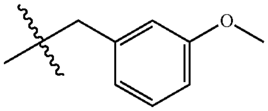
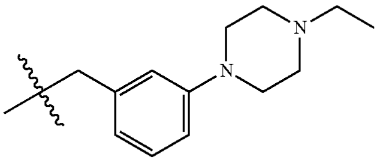
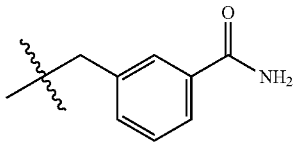
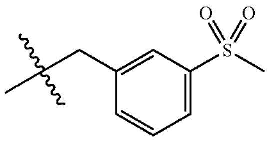
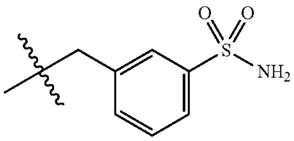
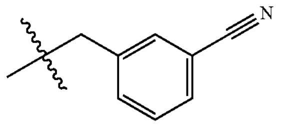
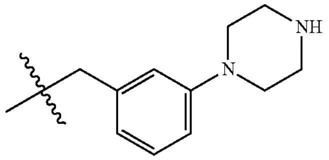
-continued
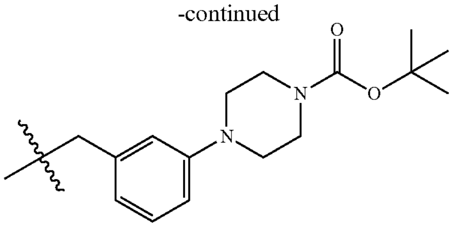
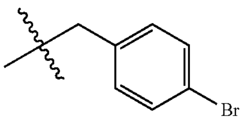
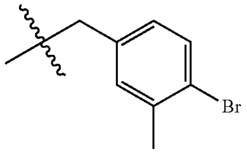
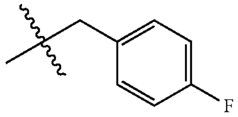
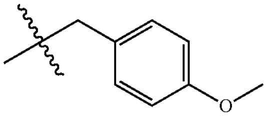
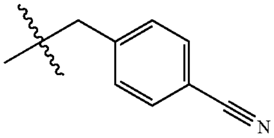
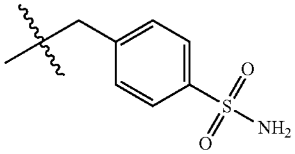
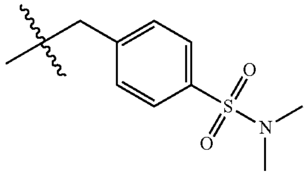
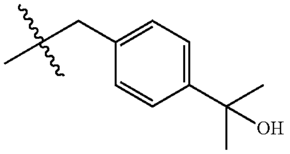
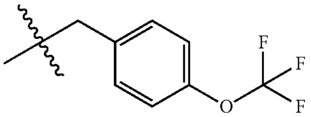
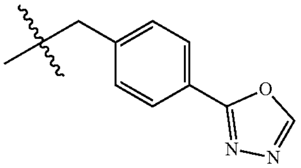
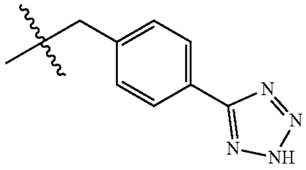
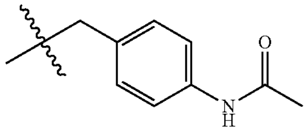
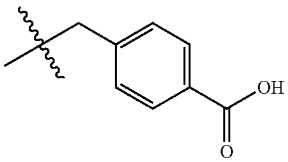

-continued
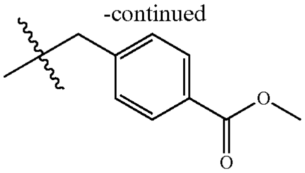
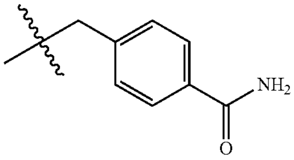
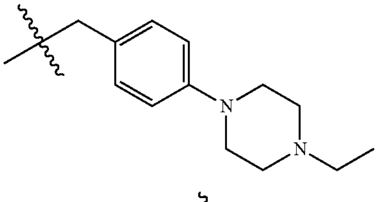
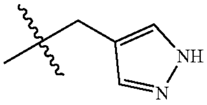
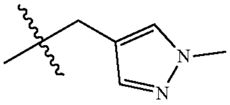
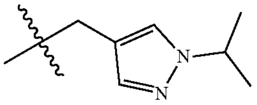
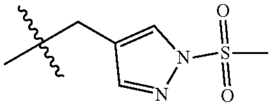
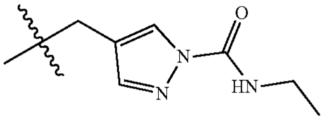
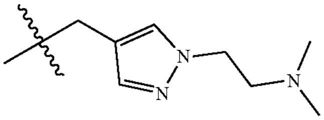
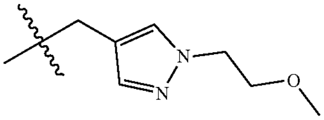
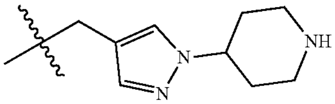
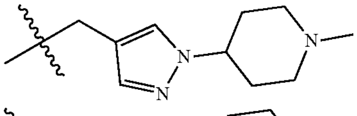
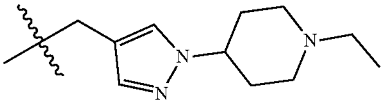
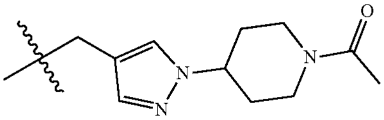
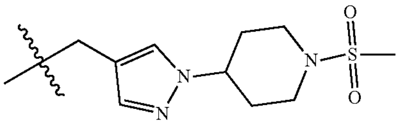
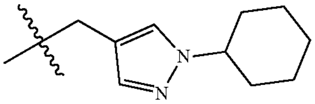
-continued
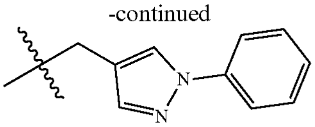
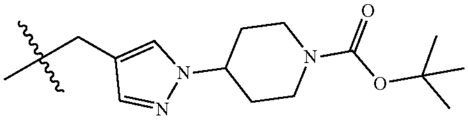
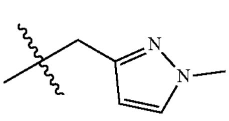
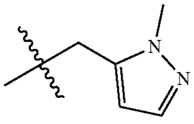
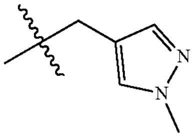
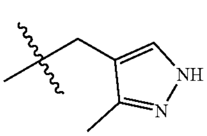
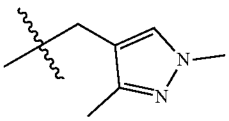
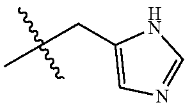
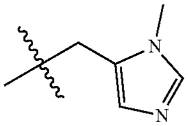
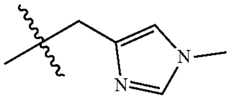
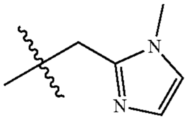
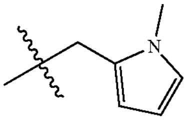
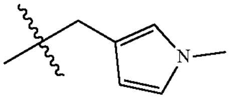
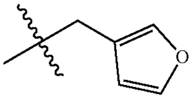
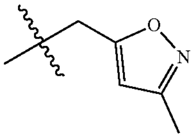
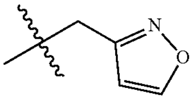
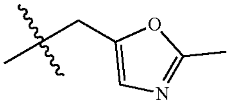
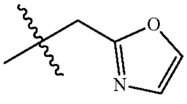
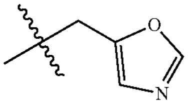
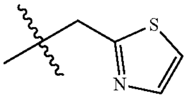
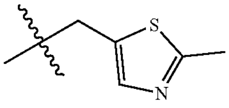
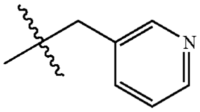
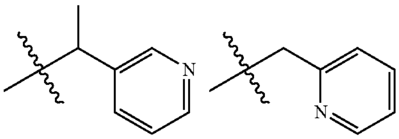
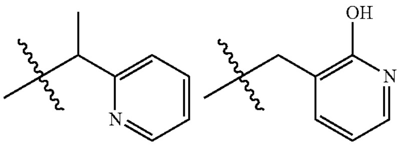

-continued
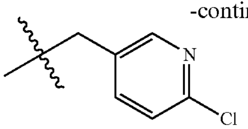
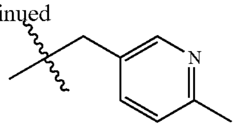
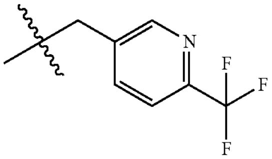
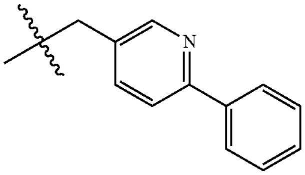
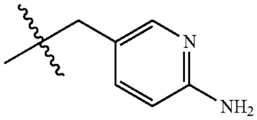
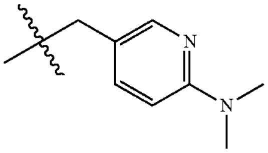
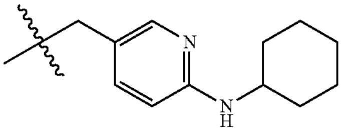
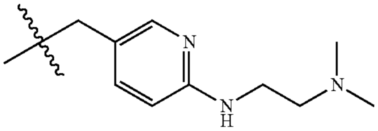
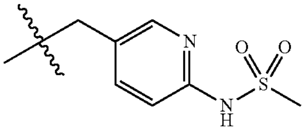
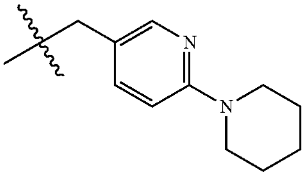
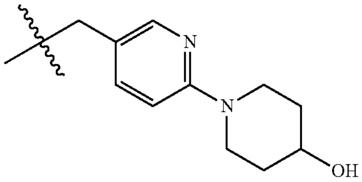
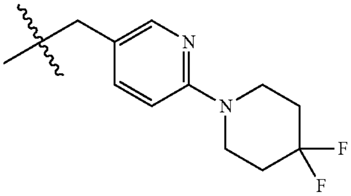
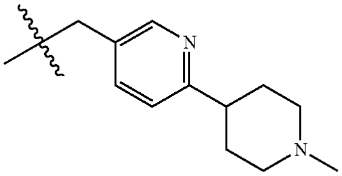
-continued
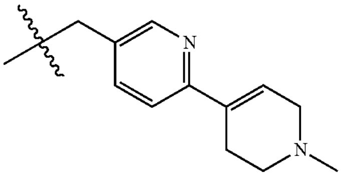
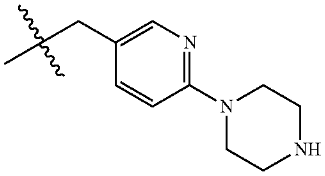
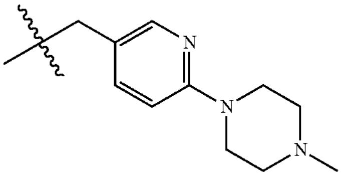
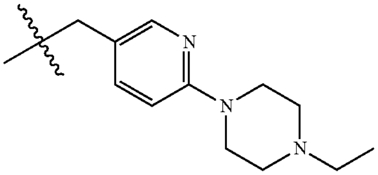
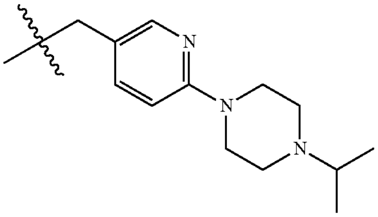
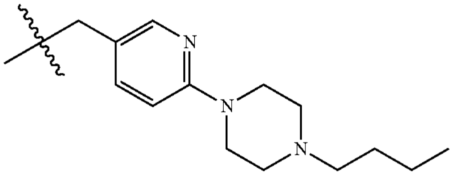
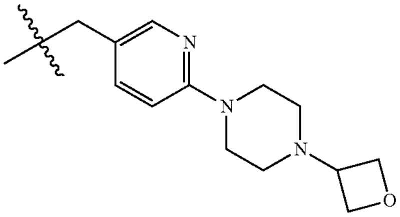
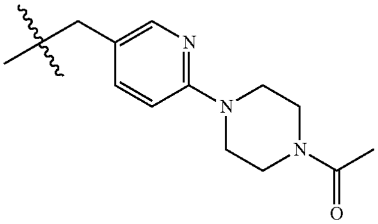

-continued
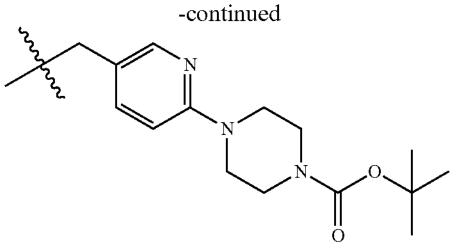
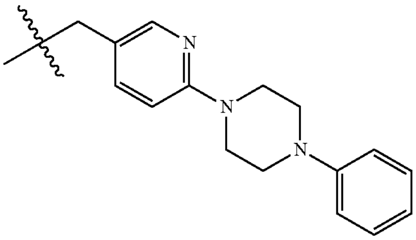
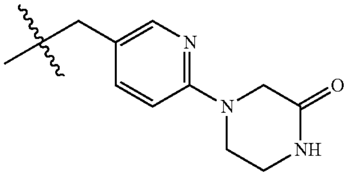
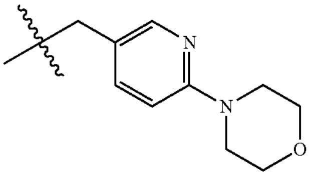
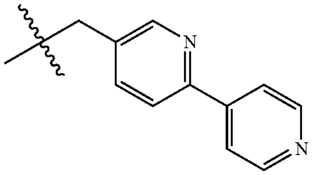
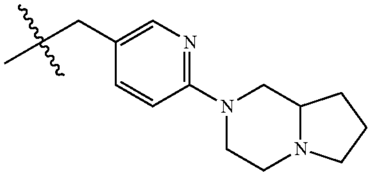
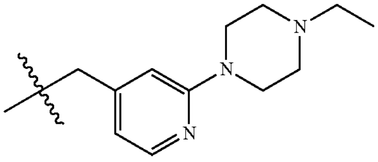
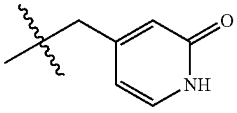
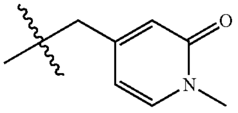
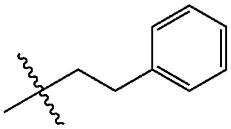
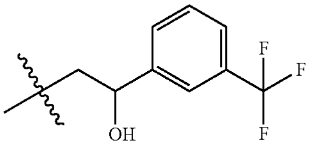
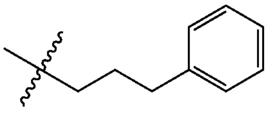
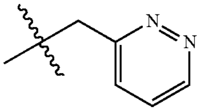
-continued
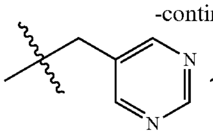
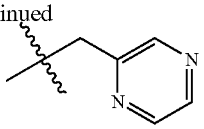
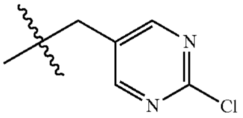
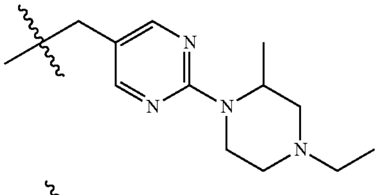
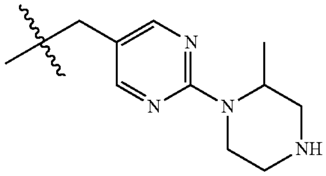
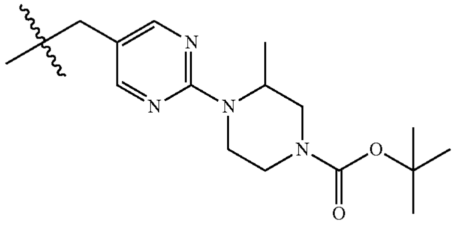
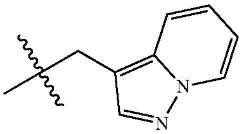
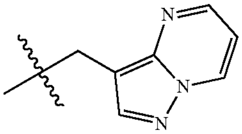
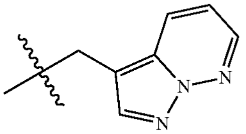
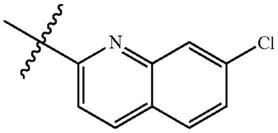
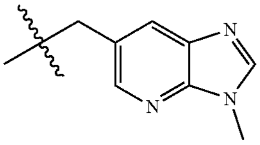
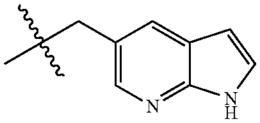
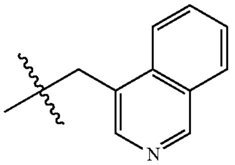
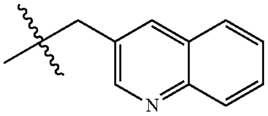
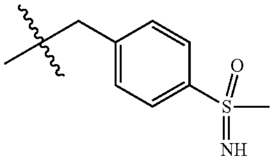
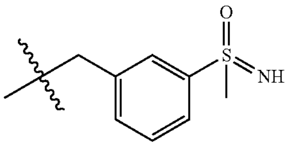
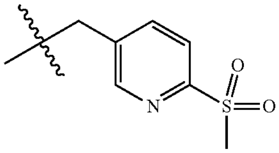
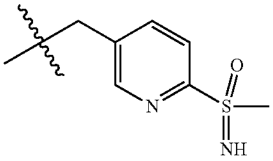

-continued

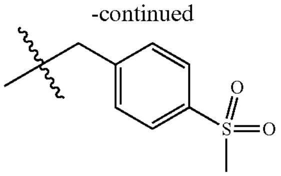

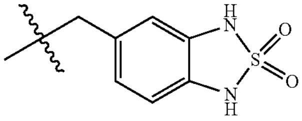

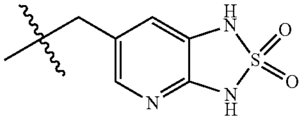

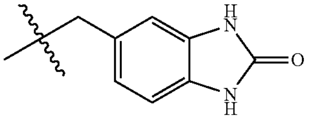

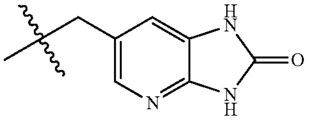

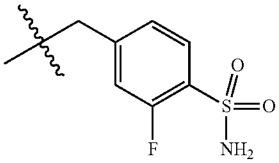

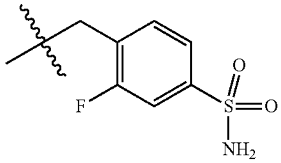

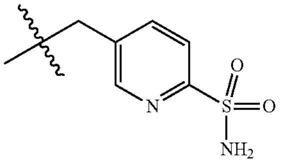

In some embodiments, $R^2$ is not

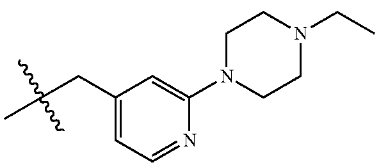

.

In some embodiments, $R^2$ is not

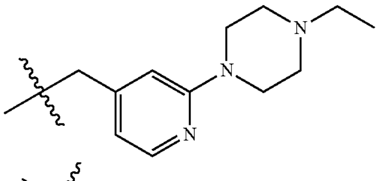

or

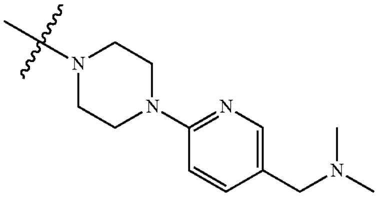

.

As defined generally above, R is selected from hydrogen or an optionally substituted group selected from $C_{1-6}$ aliphatic, phenyl, a 4- to 6-membered heterocyclic ring having 1-2 heteroatoms independently selected from nitrogen, oxygen, or sulfur, a 5- to 6-membered heteroaryl ring having 1-3 heteroatoms independently selected from nitrogen, oxygen, or sulfur, and an 8- to 10-membered heteroaryl ring having 1-3 heteroatoms independently selected from nitrogen, oxygen, or sulfur. In some embodiments, R is hydrogen. In some embodiments, R is an optionally substituted group selected from $C_{1-6}$ aliphatic, phenyl, a 4- to 6-membered heterocyclic ring having 1-2 heteroatoms independently selected from nitrogen, oxygen, or sulfur, a 5- to 6-membered heteroaryl ring having 1-3 heteroatoms independently selected from nitrogen, oxygen, or sulfur, and an 8- to 10-membered heteroaryl ring having 1-3 heteroatoms independently selected from nitrogen, oxygen, or sulfur.

In some embodiments, R is optionally substituted $C_{1-6}$ aliphatic. In some embodiments, R is optionally substituted $C_{1-2}$ aliphatic. In some embodiments, R is optionally substituted $C_{3-4}$ aliphatic. In some embodiments, R is optionally substituted $C_{5-6}$ aliphatic. In some embodiments, R is $-CH_3$. In some embodiments, R is $-CH_2CH_3$. In some embodiments, R is $-CH_2CH_2CH_3$ or $-CH(CH_3)_2$. In some embodiments, R is $-CH_2CH(CH_3)_2$. In some embodiments, R is $-(CH_2)_4CH_3$. In some embodiments, R is $C_{1-6}$ aliphatic optionally substituted with a group selected from halogen, $-(CH_2)_{0-4}R^\circ$, $-(CH_2)_{0-4}OR^\circ$, $-(CH_2)_{0-4}N(R^\circ)_2$, or $-(CH_2)_{0-4}N(R^\circ)CO_2R^\circ$. In some embodiments, R is $-CH_2-R^\circ$, $-CH_2-OR^\circ$, $-CH_2-N(R^\circ)_2$, or $-CH_2-N(R^\circ)CO_2R^\circ$. In some embodiments, R is $-CH_2CH_2-R^\circ$, $-CH_2CH_2-OR^\circ$, $-CH_2CH_2-N(R^\circ)_2$, or $-CH_2CH_2-N(R^\circ)CO_2R^\circ$. In some embodiments, R is $-(CH_2)_3-R^\circ$, $-(CH_2)_3-OR^\circ$, $-(CH_2)_3-N(R^\circ)_2$, or $-(CH_2)_3-N(R^\circ)CO_2R^\circ$. In some embodiments, R is $-(CH_2)_4-R^\circ$, $-(CH_2)_4-OR^\circ$, $-(CH_2)_4-N(R^\circ)_2$, or $-(CH_2)_4-N(R^\circ)CO_2R^\circ$.

In some embodiments, R is $C_{1-6}$ aliphatic optionally substituted with halogen. In some embodiments, R is $C_{1-2}$ aliphatic optionally substituted with halogen. In some embodiments, R is $C_{1-6}$ aliphatic optionally substituted with $-OH$, $-R^\circ$, wherein $R^\circ$ is selected from.

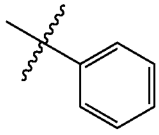

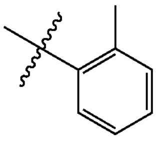

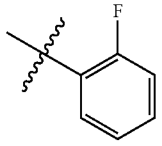

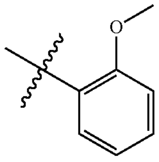

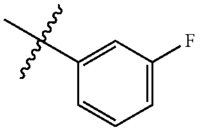

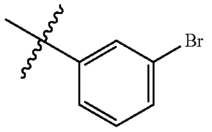

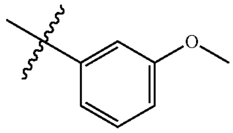

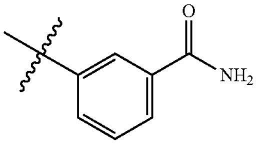

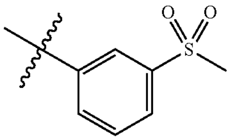

-continued
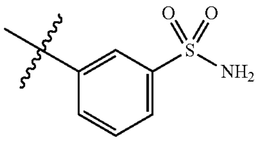
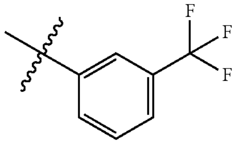
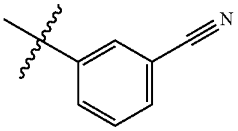
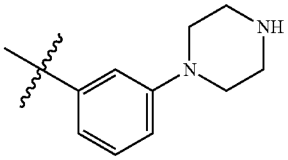
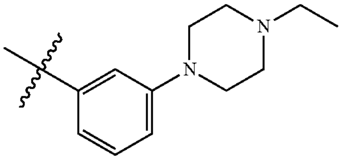
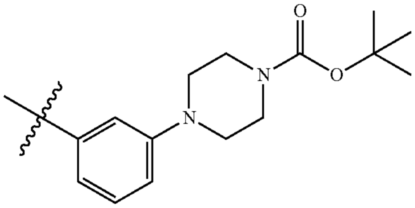
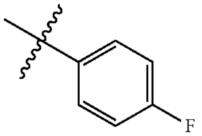
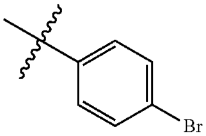
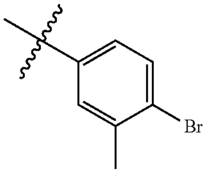
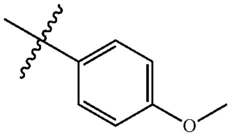
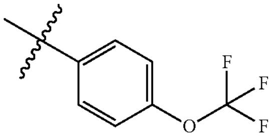
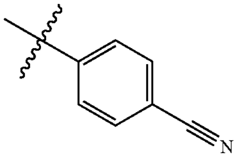
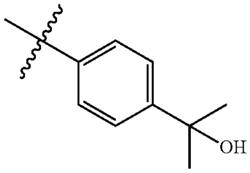
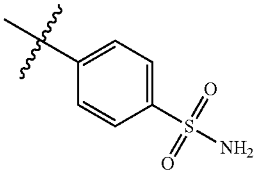
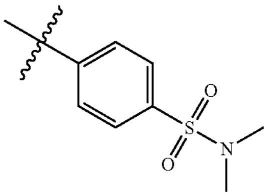
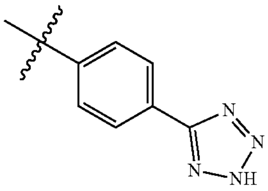
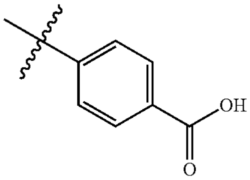
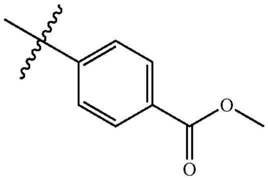
-continued
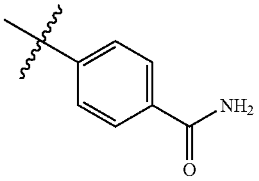
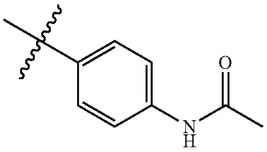
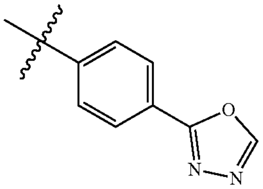
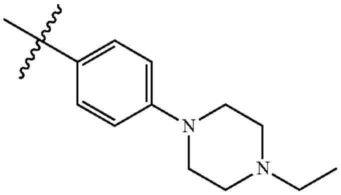
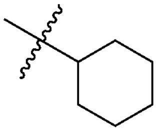
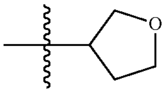
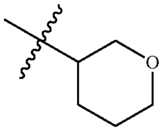
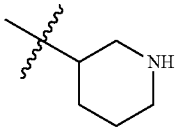
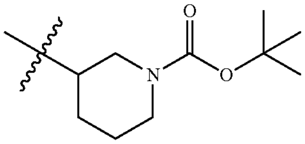
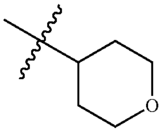
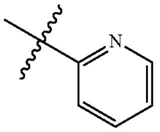
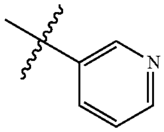
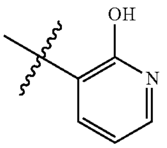
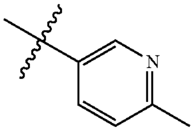
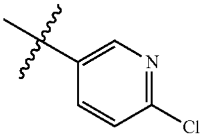
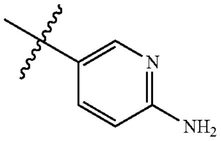
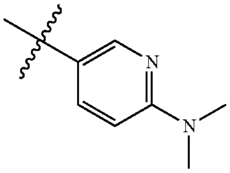
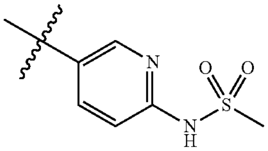
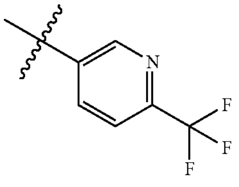
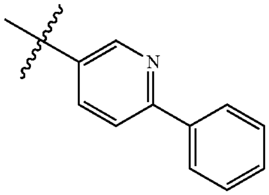

-continued
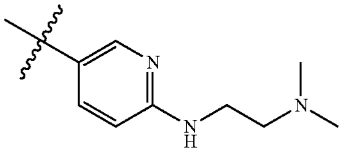
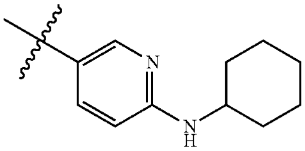
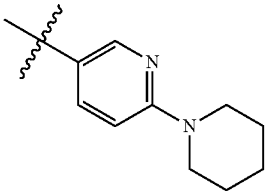
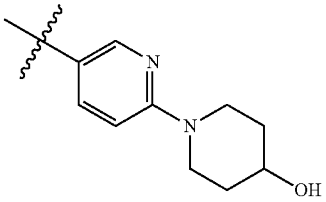
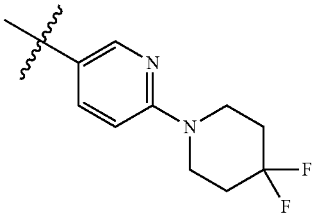
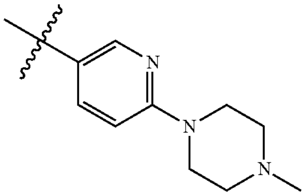
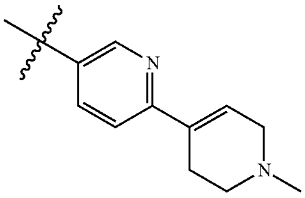
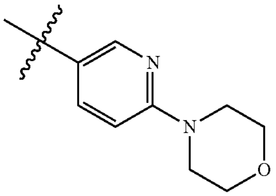
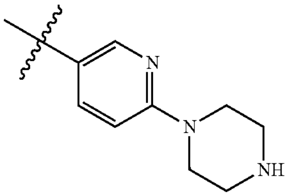
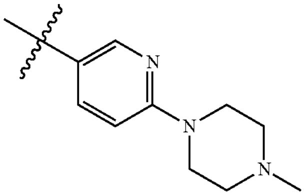
-continued
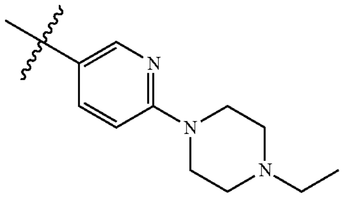
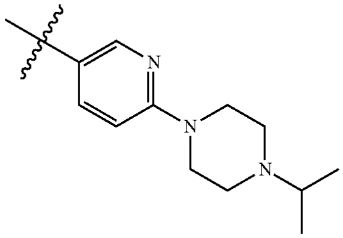
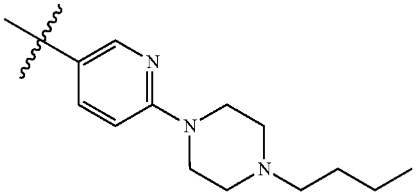
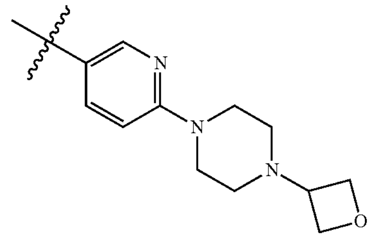
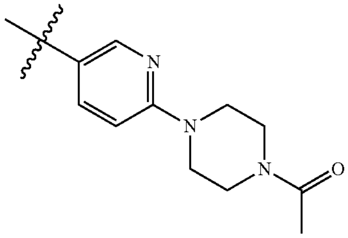
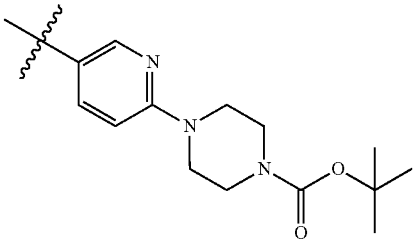
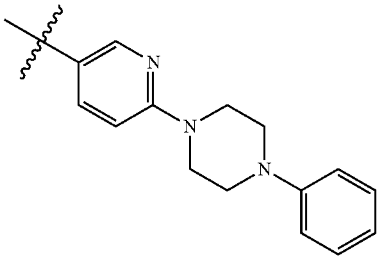

-continued
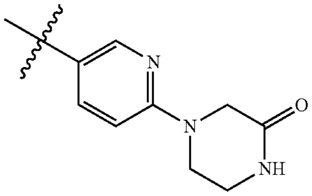
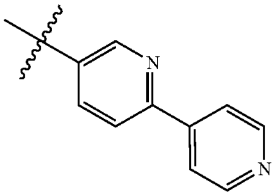
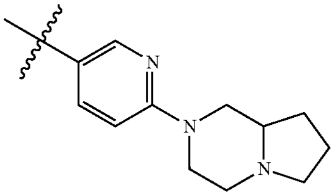
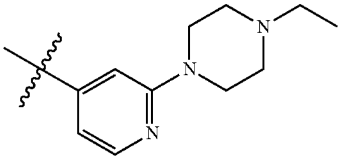
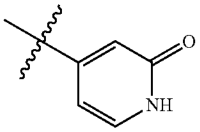
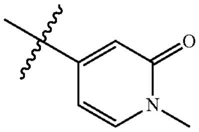
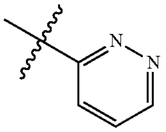
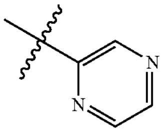
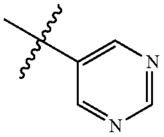
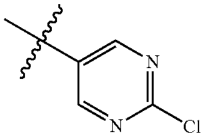
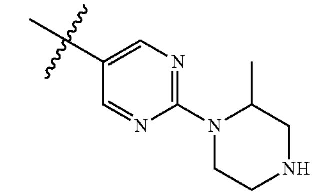
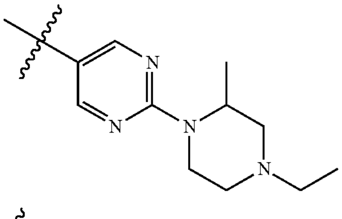
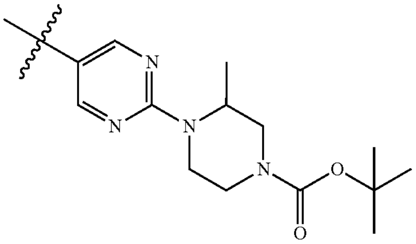
-continued
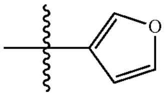
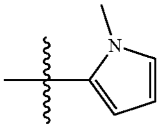
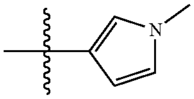
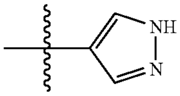
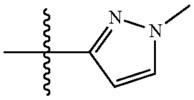
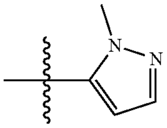
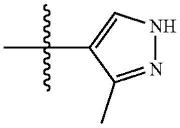
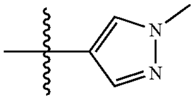
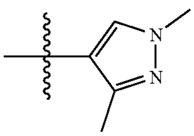
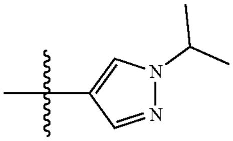
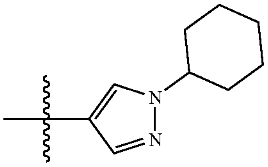
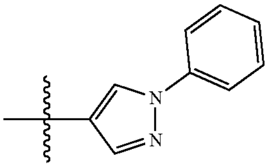
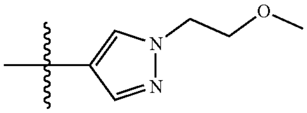
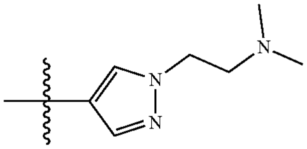
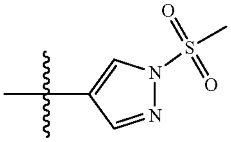
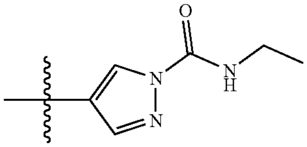
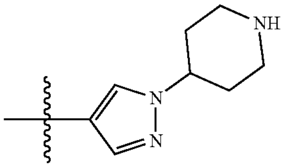
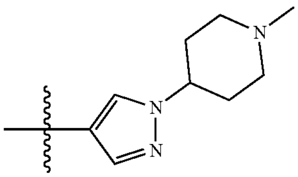
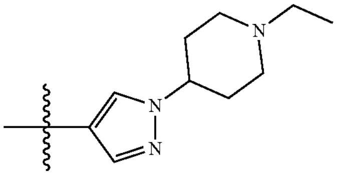

-continued
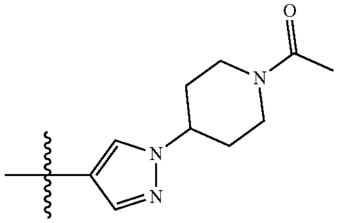
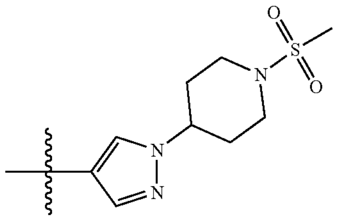
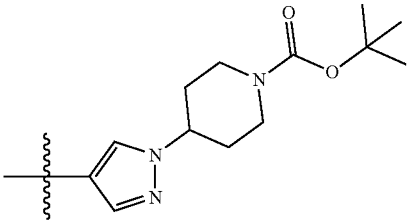
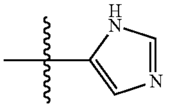
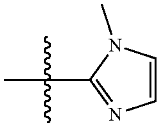
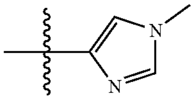
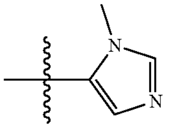
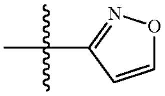
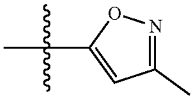
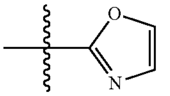
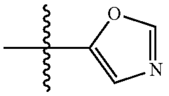
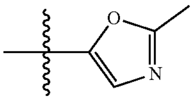
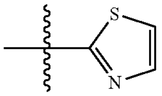
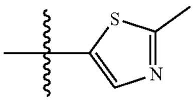
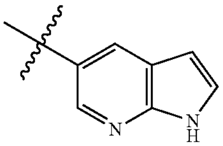
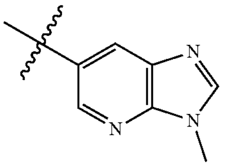
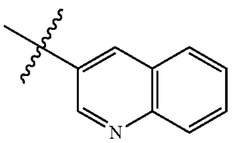
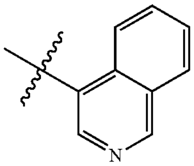
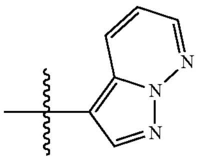
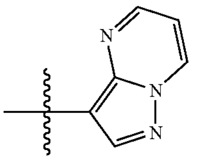
-continued
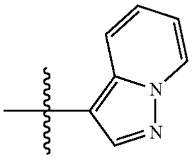
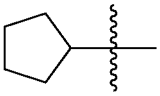
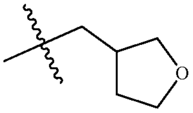
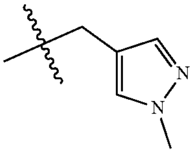
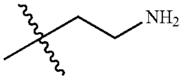
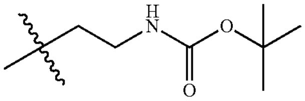
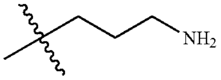
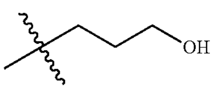
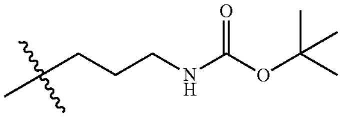
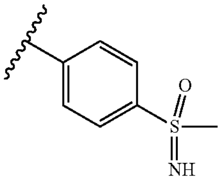
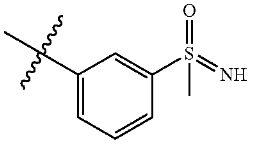
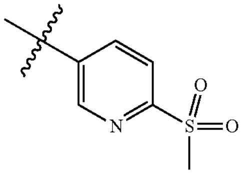
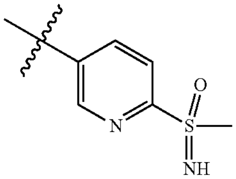
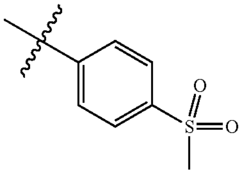
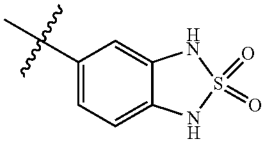
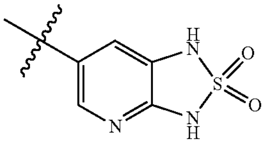
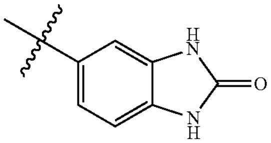
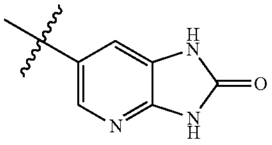
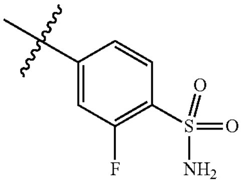
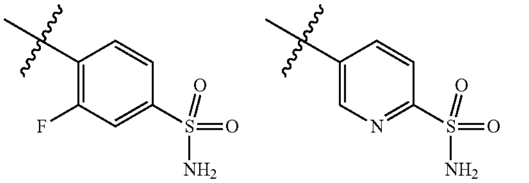

In some such embodiments, R° is not
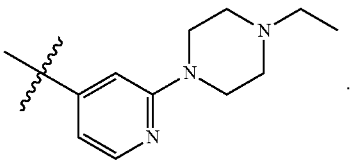 [SMILES: *c1ccnc(N2CCN(CC)CC2)c1].
In some embodiments, R is selected from hydrogen, $—CH_3$, $—CH_2F$, $—CH_2CH_3$, $—CH_2CF_3$, $—CH_2CHF_2$, $—CH_2CH_2CH_3$, $—CH(CH_3)_2$, $—(CH_2)_4CH_3$, $—CH_2CH(CH_3)_2$, phenyl, or a group selected from
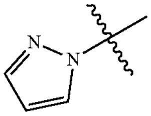
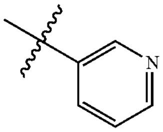
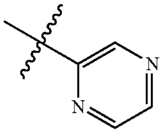
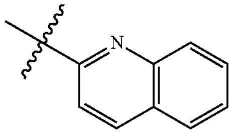
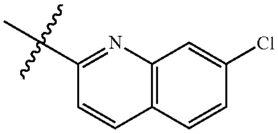
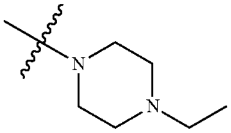
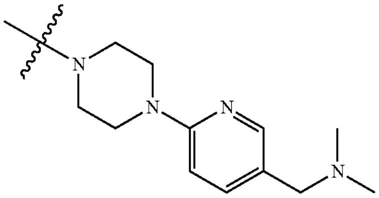
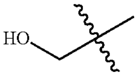
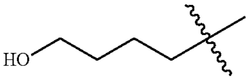
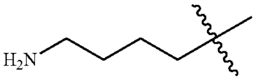
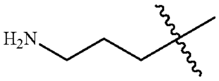
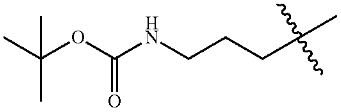
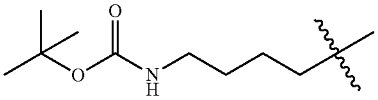
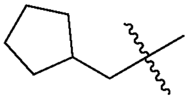
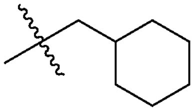
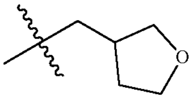
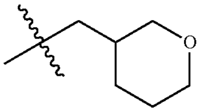
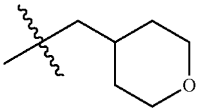
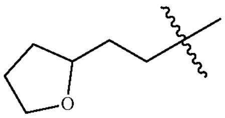
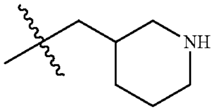
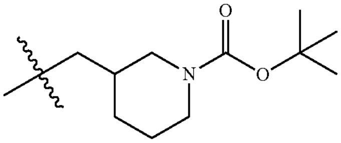
-continued
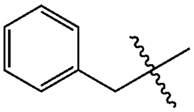
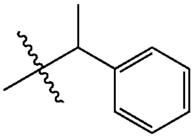
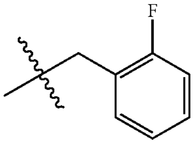
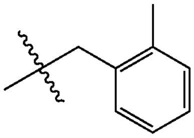
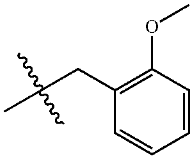
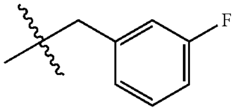
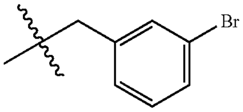
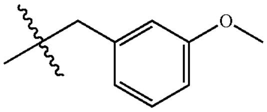
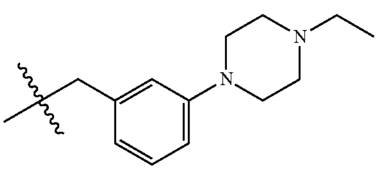
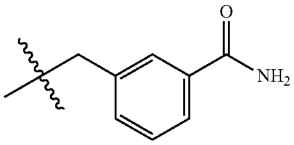
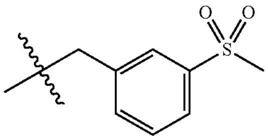
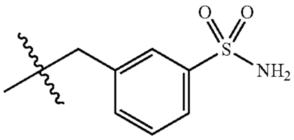
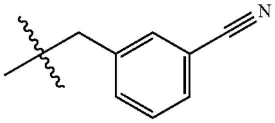
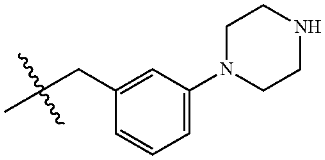
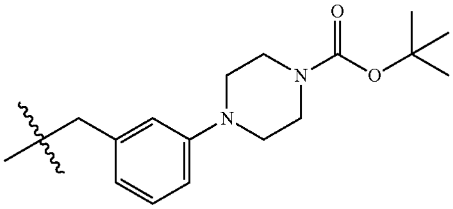
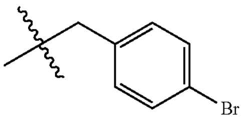
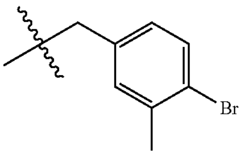

-continued
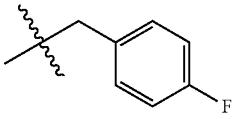
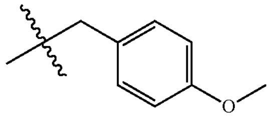
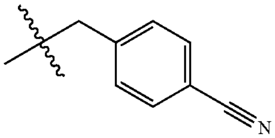
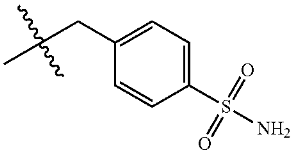
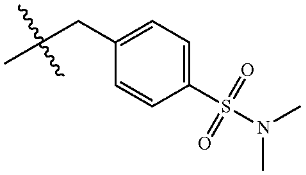
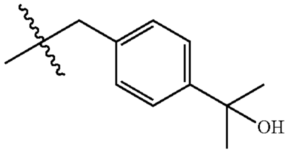
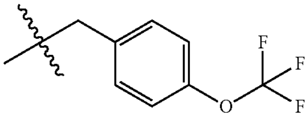
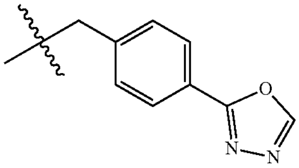
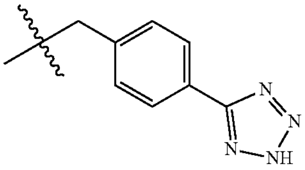
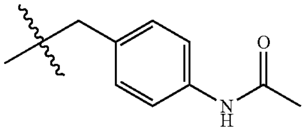
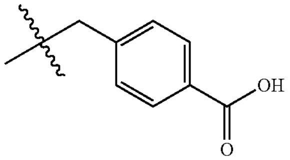
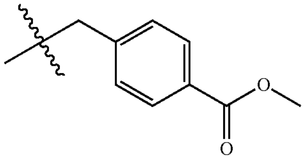
-continued
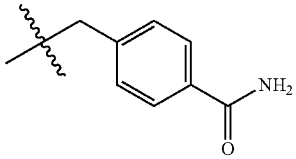
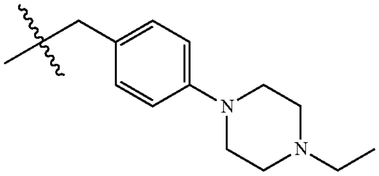
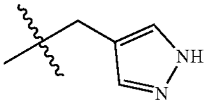
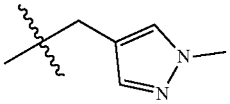
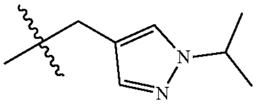
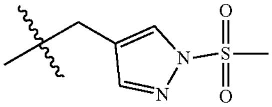
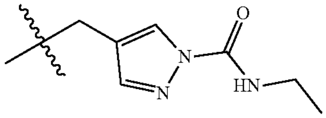
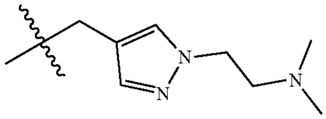
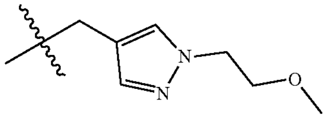
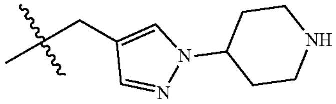
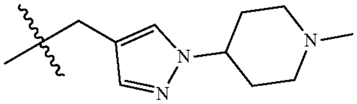
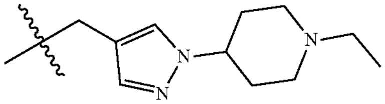
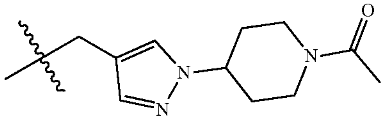
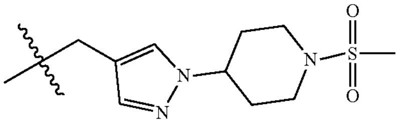
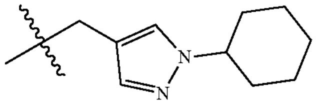
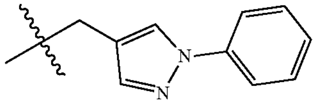

-continued
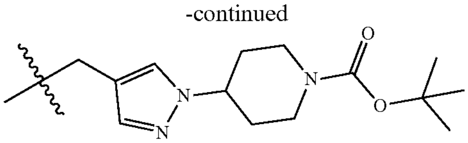
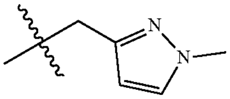
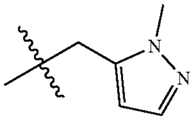
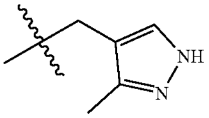
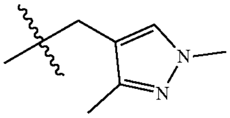
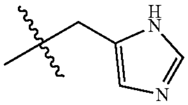
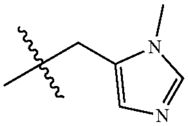
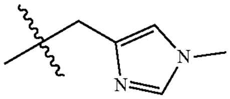
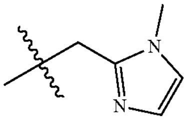
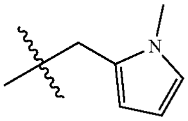
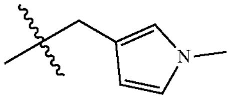
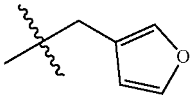
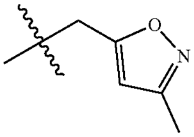
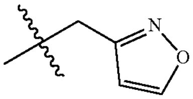
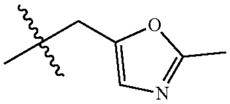
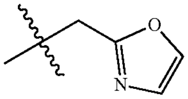
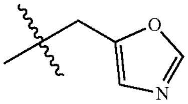
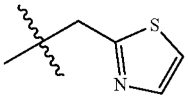
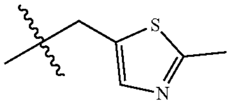
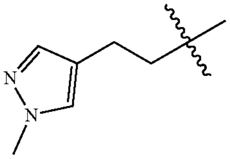
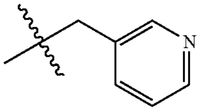
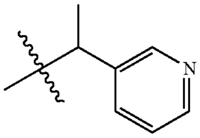
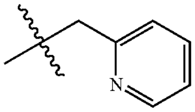
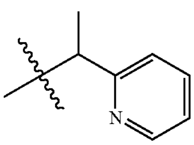
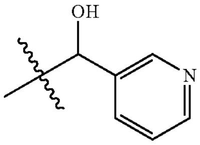
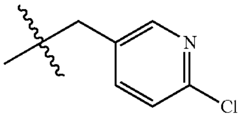
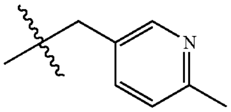
-continued
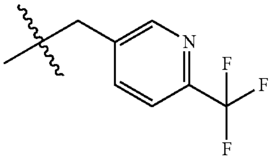
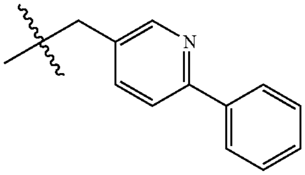
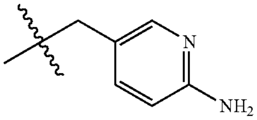
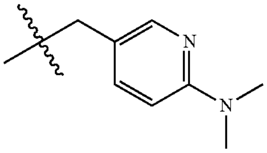
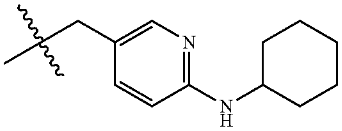
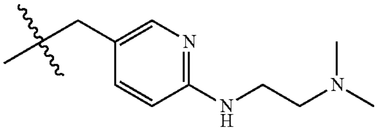
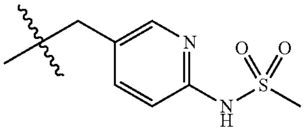
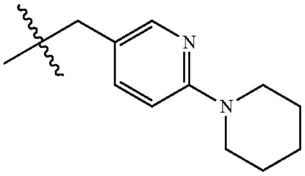
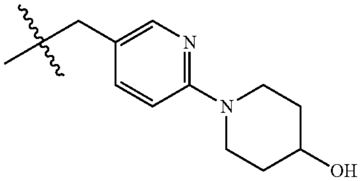
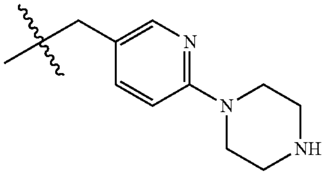
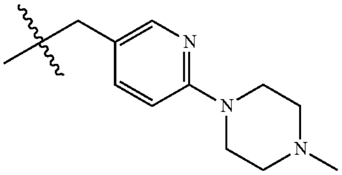

-continued
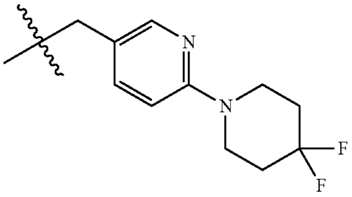
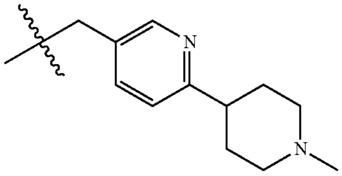
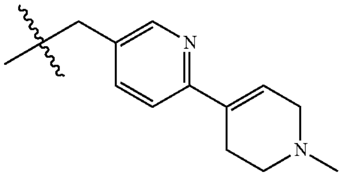
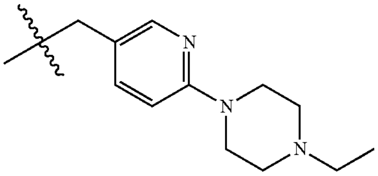
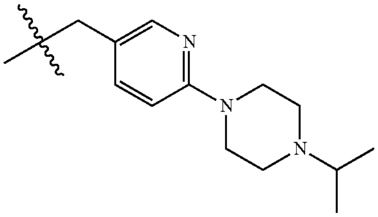
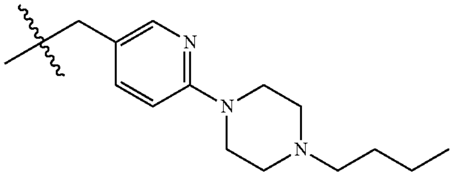
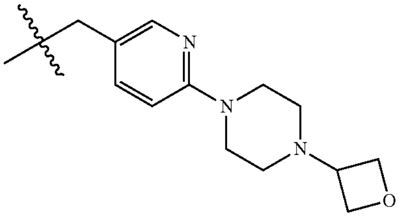
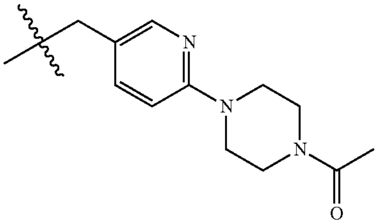
-continued
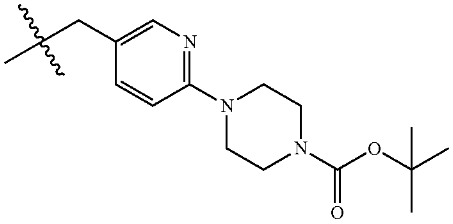
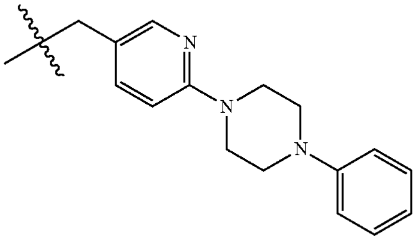
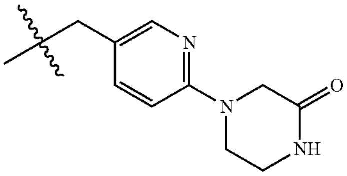
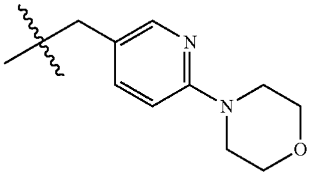
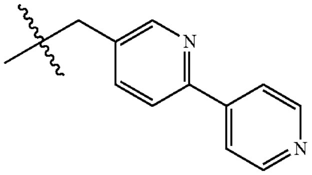
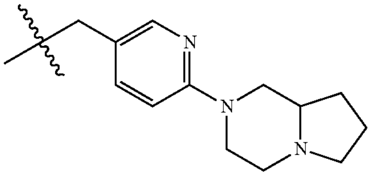
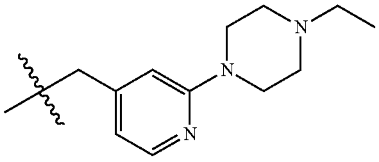
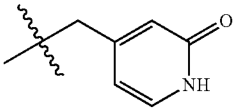
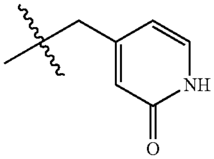
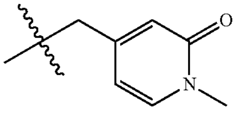
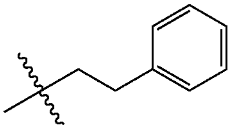

-continued
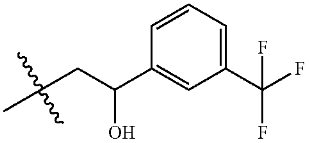
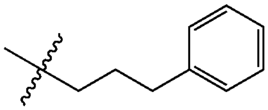
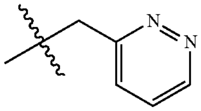
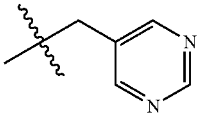
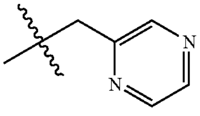
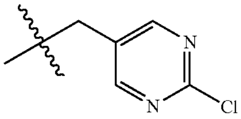
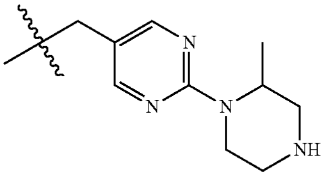
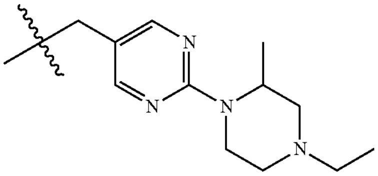
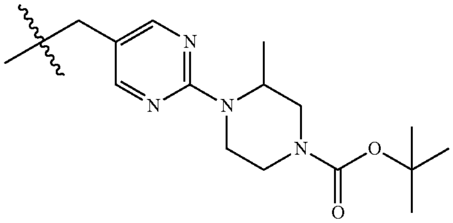
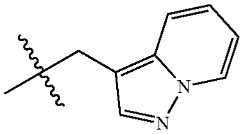
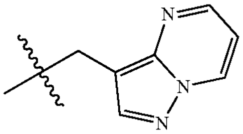
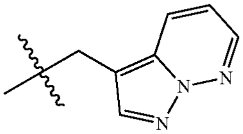
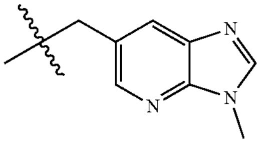
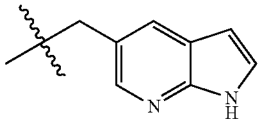
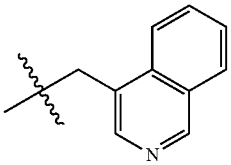
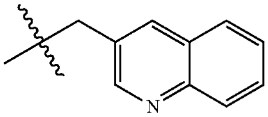
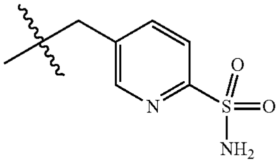
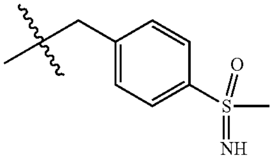
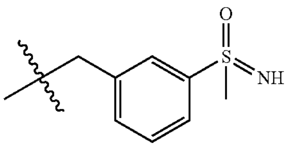
-continued
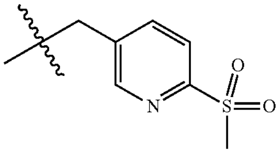
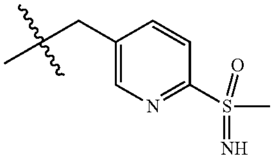
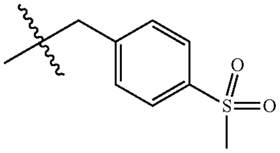
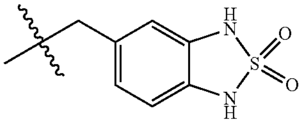
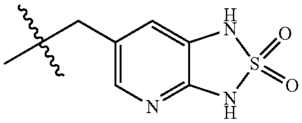
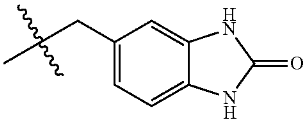
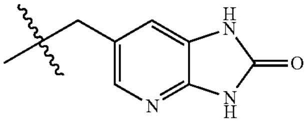
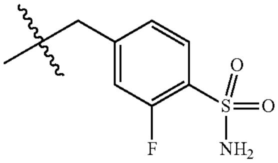
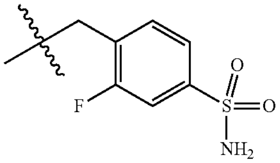
In some embodiments R is not
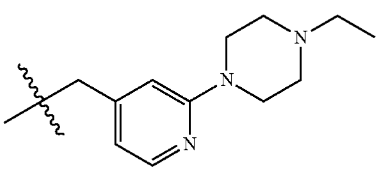
.
In some embodiments of Formula I, $L^2$ is —N(R)—. Accordingly, in some embodiments, the present disclosure provides a compound of Formula I-a:
I-a
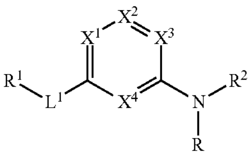
or a pharmaceutically acceptable salt there of, wherein of $X^1$, $X^2$, $X^3$, $X^4$, $L^1$, $R^1$, $R^2$, and R is as defined above and described herein.

In some embodiments of Formula I, $L^1$ is —O—. Accordingly, in some embodiments, the present disclosure provides a compound of Formula I-b:

I-b

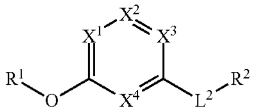

or a pharmaceutically acceptable salt thereof, wherein each of $X^1$, $X^2$, $X^3$, $X^4$, $L^2$, $R^1$, and $R^2$ is as defined above and described herein.

In some embodiments of Formula I, $L^1$ is —O— and $L^2$ is —N(R)—. Accordingly, in some embodiments, the present disclosure provides a compound of Formula I-c:

I-c

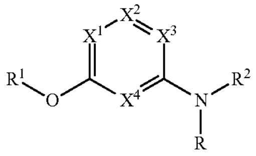

or a pharmaceutically acceptable salt thereof, wherein each of $X^1$, $X^2$, $X^3$, $X^4$, $R^1$, $R^2$, and R is as defined above and described herein.

In some embodiments of Formula I, $X^2$ is N. Accordingly, in some embodiments, the present disclosure provides a compound of Formula I-d:

I-d

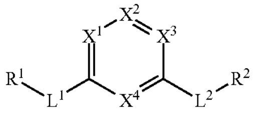

or a pharmaceutically acceptable salt thereof, wherein each of $X^1$, $X^3$, $X^4$, $L^1$, $L^2$, $R^1$, and $R^2$ is as defined above and described herein.

In some embodiments of Formula I-a, I-b, and I-c, $X^2$ is N. Accordingly, in some embodiments, the present disclosure provides a compound of Formula I-a-i, I-b-i, and I-c-i:

I-a-i

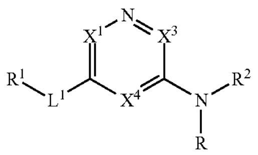

I-b-i

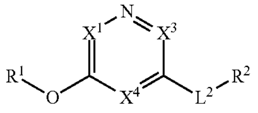

-continued

I-c-i

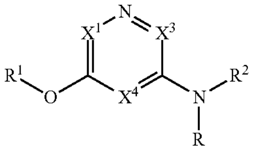

or a pharmaceutically acceptable salt thereof, wherein each of $X^1$, $X^3$, $X^4$, $L^1$, $L^2$, $R^1$, $R^2$, and R is as defined above and described herein.

In some embodiments of Formula I-a-i, I-b-i, and I-c-i, $X^4$ is N and each of $X^1$ and $X^3$ is CH. Accordingly, in some embodiments, the present disclosure provides a compound of Formula I-a-ii, I-b-ii, and I-c-ii:

I-a-ii

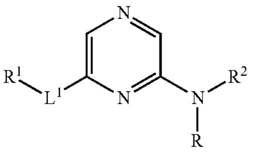

I-b-ii

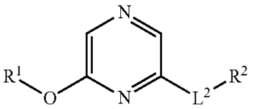

I-c-ii

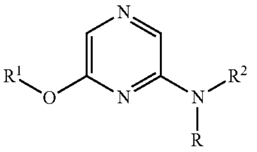

or a pharmaceutically acceptable salt thereof, wherein each of $R^1$, $R^2$, and R, is as defined above and described herein.

In some embodiments of Formula I-a, I-a-i, I-a-ii, I-b, I-b-i, I-b-ii, I-c, I-c-i, and I-c-ii, $R^2$ is optionally substituted $C_{1-6}$ aliphatic. In some such embodiments, the present disclosure provides a compound of Formula I-a-iii, I-a-iv, I-a-v, I-b-iii, I-b-iv, I-b-v, I-c-iii, I-c-iv, and I-c-v:

I-a-iii

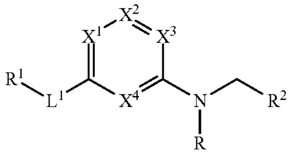

I-a-iv

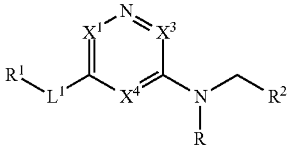

I-a-v

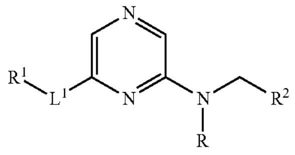

-continued
I-b-iii
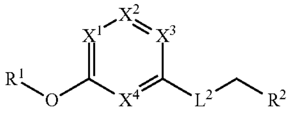
I-b-iv
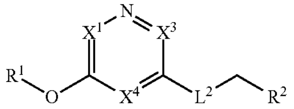
I-b-v
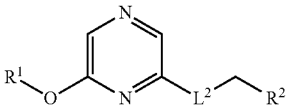
I-c-iii
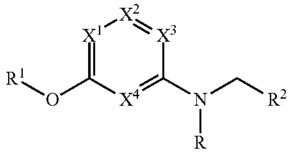
-continued
I-c-iv
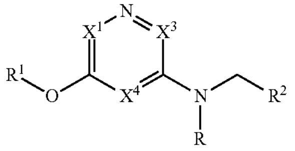
I-c-v
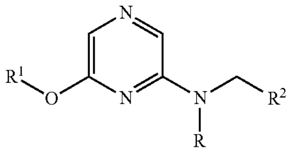
or a pharmaceutically acceptable salt thereof, wherein each of $X^1$, $X^2$, $X^3$, $X^4$, $L^1$, $L^2$, $R^1$, $R^2$, and R is as defined above and described herein.
In some embodiments, the present disclosure provides a compound selected from:
| Example | Structure |
|---|---|
| 1 | 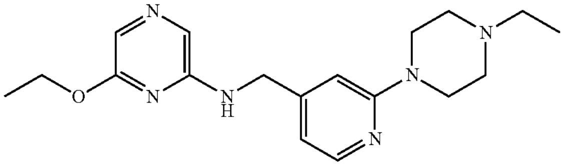 [SMILES: CCOc1cncc(NCc2ccnc(N3CCN(CC)CC3)c2)n1] |
| 2 | 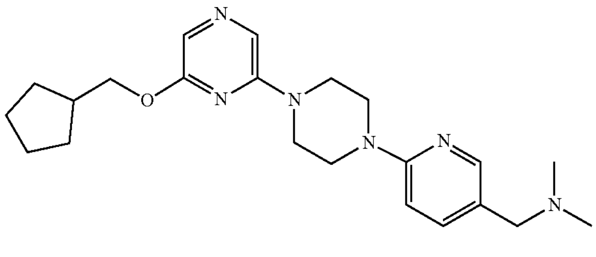 [SMILES: CN(C)Cc1ccc(N2CCN(c3cncc(OCC4CCCC4)n3)CC2)nc1] |
| 3 | 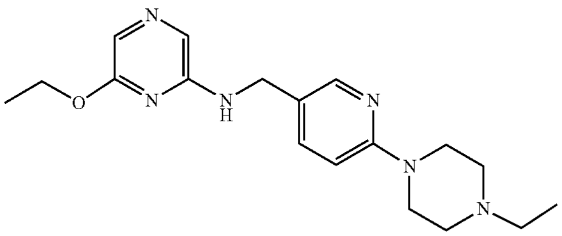 [SMILES: CCOc1cncc(NCc2ccc(N3CCN(CC)CC3)nc2)n1] |
| 4 | 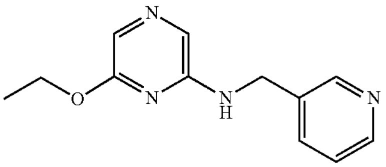 [SMILES: CCOc1cncc(NCc2cccnc2)n1] |

-continued
| Example | Structure |
|---|---|
| 5 | 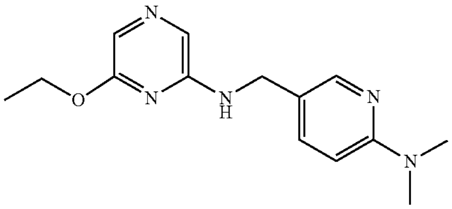 [SMILES: CCOc1cncc(NCc2ccc(N(C)C)nc2)n1] |
| 6 | 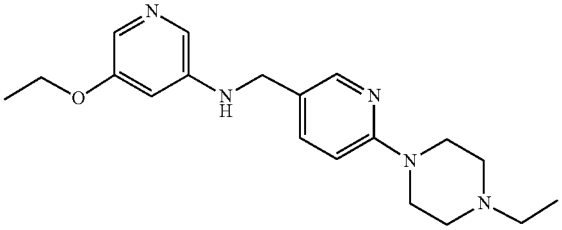 [SMILES: CCOc1cncc(NCc2ccc(N3CCN(CC)CC3)nc2)c1] |
| 7 | 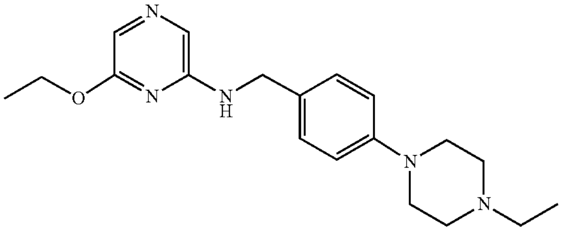 [SMILES: CCOc1cncc(NCc2ccc(N3CCN(CC)CC3)cc2)n1] |
| 8 | 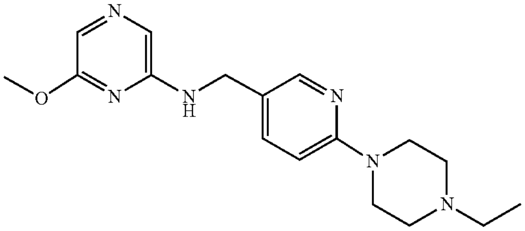 [SMILES: CCN1CCN(c2ccc(CNc3cncc(OC)n3)cn2)CC1] |
| 9 | 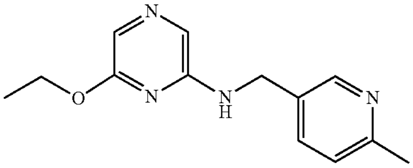 [SMILES: CCOc1cncc(NCc2ccc(C)nc2)n1] |
| 10 | 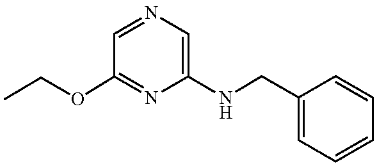 [SMILES: CCOc1cncc(NCc2ccccc2)n1] |
| 11 | 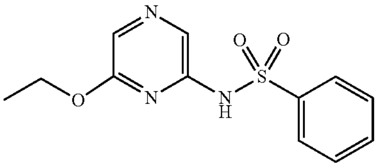 [SMILES: CCOc1cncc(NS(=O)(=O)c2ccccc2)n1] |

-continued
| Example | Structure |
|---|---|
| 12 | 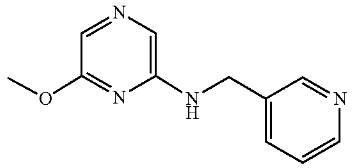 [SMILES: COc1cncc(NCc2cccnc2)n1] |
| 13 | 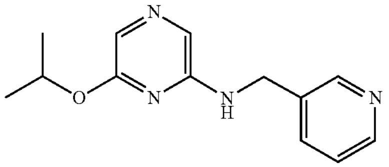 [SMILES: CC(C)Oc1cncc(NCc2cccnc2)n1] |
| 14 | 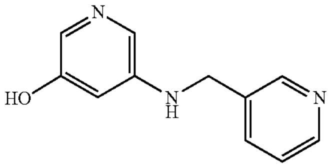 [SMILES: Oc1cncc(NCc2cccnc2)c1] |
| 15 | 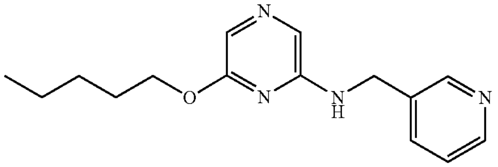 [SMILES: CCCCCOc1cncc(NCc2cccnc2)n1] |
| 16 | 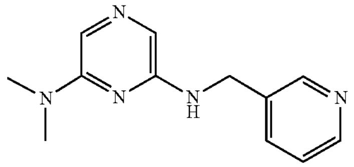 [SMILES: CN(C)c1cncc(NCc2cccnc2)n1] |
| 17 | 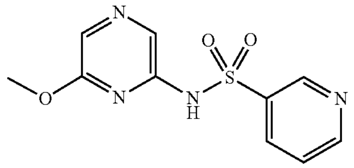 [SMILES: COc1cncc(NS(=O)(=O)c2cccnc2)n1] |
| 18 | 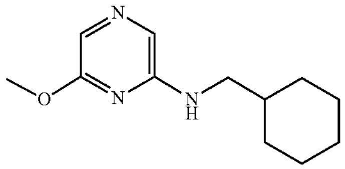 [SMILES: COc1cncc(NCC2CCCCC2)n1] |
| 19 | 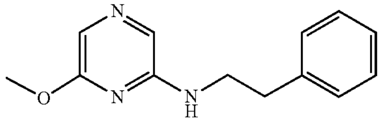 [SMILES: COc1cncc(NCCc2ccccc2)n1] |
| 20 | 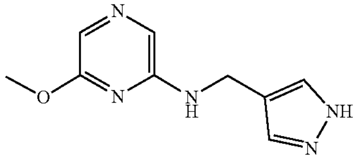 |

-continued
| Example | Structure |
| --- | --- |
| 21 | 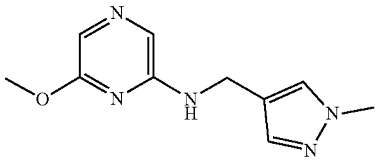 |
| 22 | 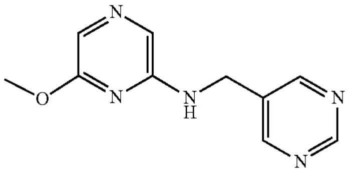 [SMILES: COc1cncc(NCc2cncnc2)n1] |
| 23 | 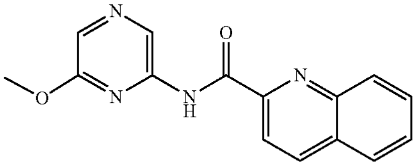 [SMILES: COc1cncc(NC(=O)c2ccc3ccccc3n2)n1] |
| 24 | 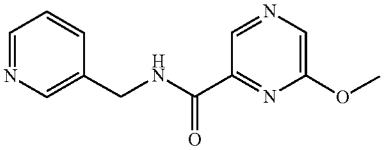 [SMILES: COc1cncc(C(=O)NCc2cccnc2)n1] |
| 25 | 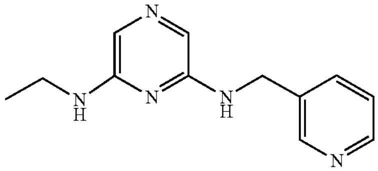 [SMILES: CCNc1cncc(NCc2cccnc2)n1] |
| 26 | 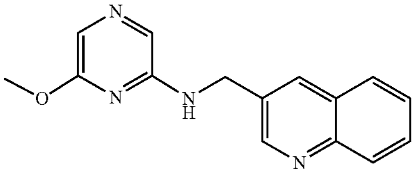 [SMILES: COc1cncc(NCc2cnc3ccccc3c2)n1] |
| 27 | 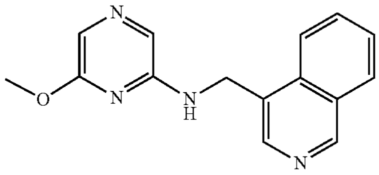 [SMILES: COc1cncc(NCc2cncc3ccccc23)n1] |
| 28 | 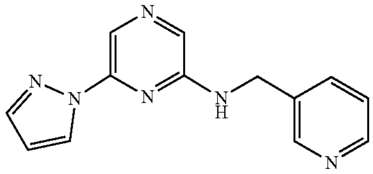 [SMILES: c1cncc(CNc2cncc(-n3cccn3)n2)c1] |

-continued
| Example | Structure |
| --- | --- |
| 29 | 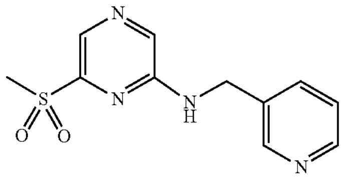 [SMILES: CS(=O)(=O)c1cncc(NCc2cccnc2)n1] |
| 30 | 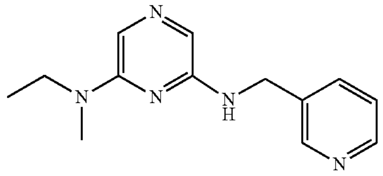 [SMILES: CCN(C)c1cncc(NCc2cccnc2)n1] |
| 31 | 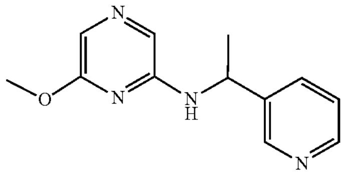 [SMILES: COc1cncc(NC(C)c2cccnc2)n1] |
| 32 | 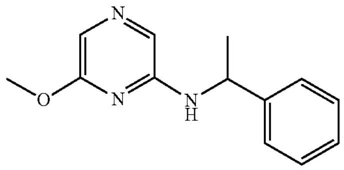 [SMILES: COc1cncc(NC(C)c2ccccc2)n1] |
| 33 | 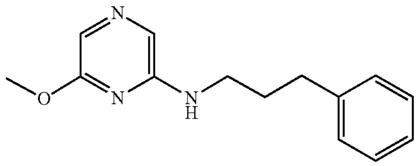 [SMILES: COc1cncc(NCCCc2ccccc2)n1] |
| 34 | 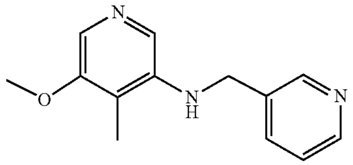 [SMILES: COc1cncc(NCc2cccnc2)c1C] |
| 35 | 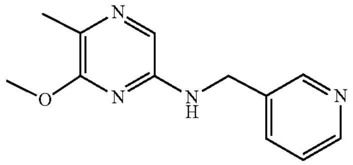 [SMILES: COc1nc(NCc2cccnc2)cnc1C] |
| 36 | 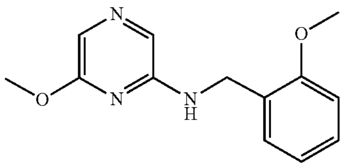 [SMILES: COc1cncc(NCc2ccccc2OC)n1] |

-continued
| Example | Structure |
|---|---|
| 37 | 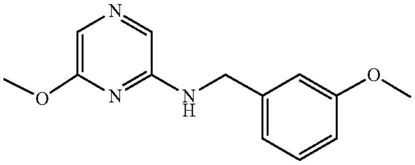 |
| 38 | 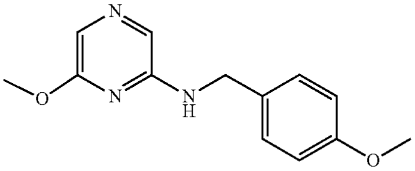 |
| 39 | 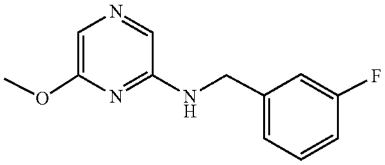 [SMILES: COc1cncc(NCc2cccc(F)c2)n1] |
| 40 | 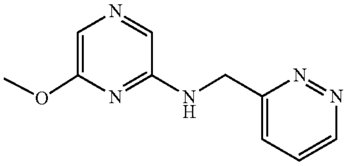 [SMILES: COc1cncc(NCc2cccnn2)n1] |
| 41 | 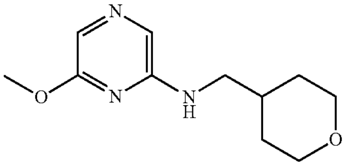 [SMILES: COc1cncc(NCC2CCOCC2)n1] |
| 42 | 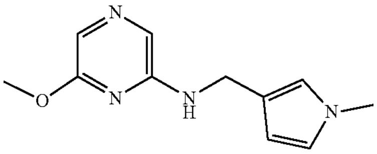 |
| 43 | 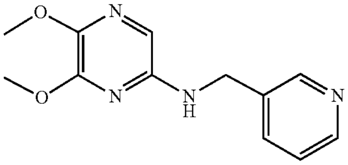 [SMILES: COc1ncc(NCc2cccnc2)nc1OC] |
| 44 | 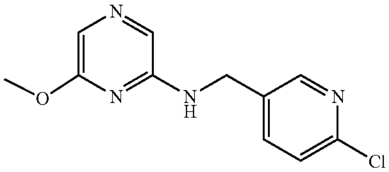 [SMILES: COc1cncc(NCc2ccc(Cl)nc2)n1] |
| 45 | 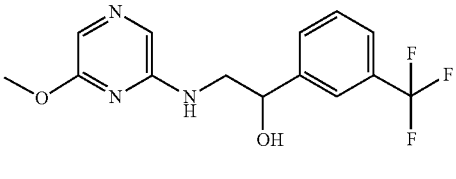 [SMILES: COc1cncc(NCC(O)c2cccc(C(F)(F)F)c2)n1] |

-continued
| Example | Structure |
| --- | --- |
| 46 | 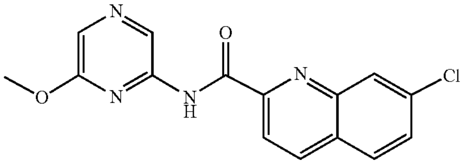 [SMILES: COc1cncc(NC(=O)c2ccc3ccc(Cl)cc3n2)n1] |
| 47 | 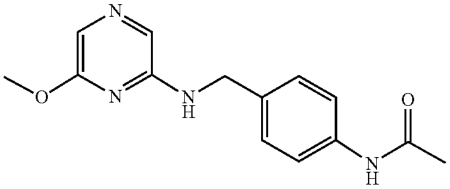 [SMILES: COc1cncc(NCc2ccc(NC(C)=O)cc2)n1] |
| 48 | 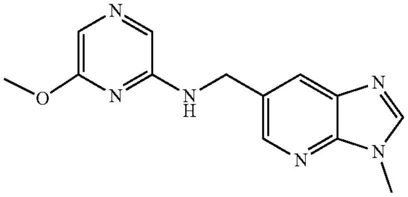 [SMILES: COc1cncc(NCc2cnc3c(c2)ncn3C)n1] |
| 49 | 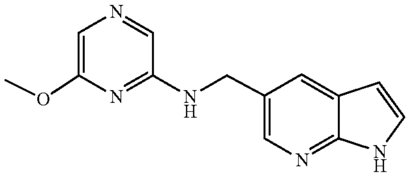 [SMILES: COc1cncc(NCc2cnc3[nH]ccc3c2)n1] |
| 50 | 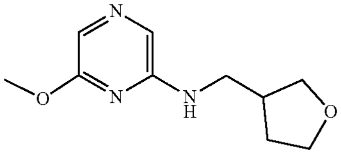 |
| 51 | 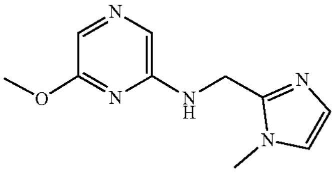 [SMILES: COc1cncc(NCc2nccn2C)n1] |
| 52 | 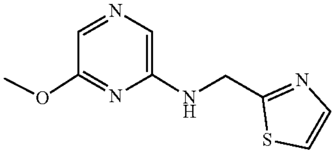 |
| 53 | 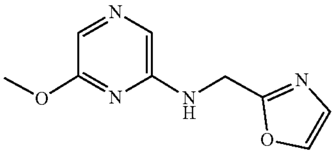 |

-continued
| Example | Structure |
| --- | --- |
| 54 | 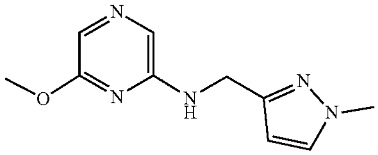 |
| 55 | 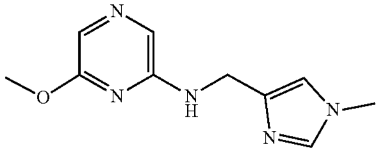 |
| 56 | 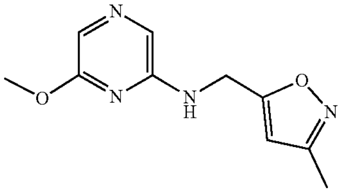 [SMILES: COc1cncc(NCc2cc(C)no2)n1] |
| 57 | 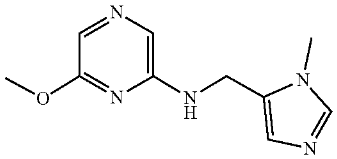 [SMILES: COc1cncc(NCc2cncn2C)n1] |
| 58 | 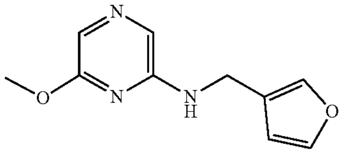 |
| 59 | 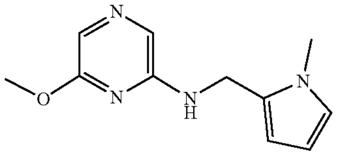 [SMILES: COc1cncc(NCc2cccn2C)n1] |
| 60 | 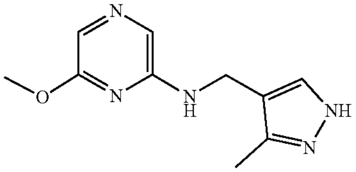 [SMILES: COc1cncc(NCc2c[nH]nc2C)n1] |
| 61 | 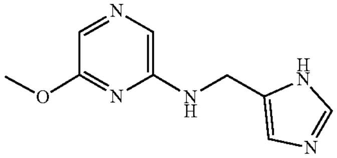 |
| 62 | 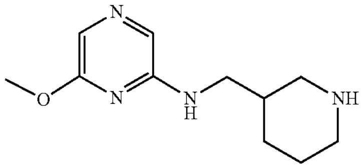 [SMILES: COc1cncc(NCC2CCCNC2)n1] |

-continued
| Example | Structure |
|---|---|
| 63 | 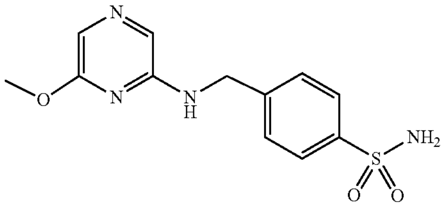 [SMILES: COc1cncc(NCc2ccc(S(N)(=O)=O)cc2)n1] |
| 64 | 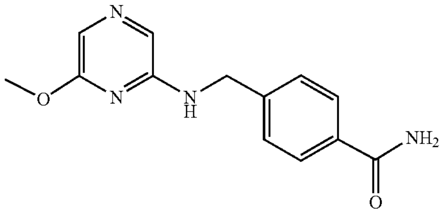 [SMILES: COc1cncc(NCc2ccc(C(N)=O)cc2)n1] |
| 65 | 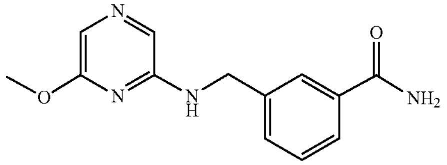 [SMILES: COc1cncc(NCc2cccc(C(N)=O)c2)n1] |
| 66 | 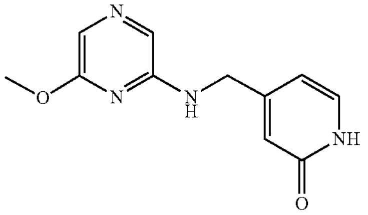 [SMILES: COc1cncc(NCc2cc[nH]c(=O)c2)n1] |
| 67 | 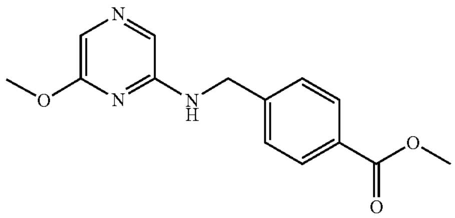 |
| 68 | 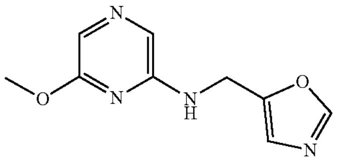 |
| 69 | 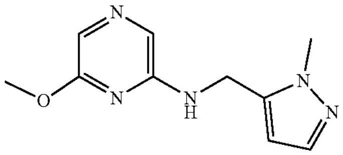 [SMILES: COc1cncc(NCc2ccnn2C)n1] |
| 70 | 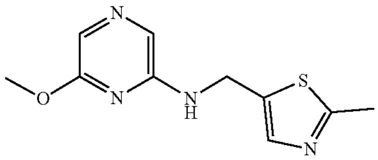 |

-continued
| Example | Structure |
|---|---|
| 71 | 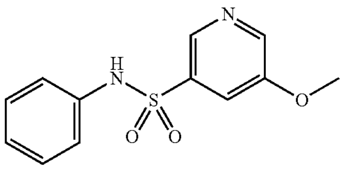 [SMILES: COc1cncc(S(=O)(=O)Nc2ccccc2)c1] |
| 72 | 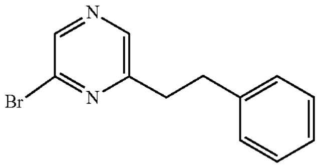 [SMILES: Brc1cncc(CCc2ccccc2)n1] |
| 73 | 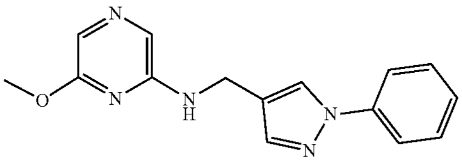 [SMILES: COc1cncc(NCc2cnn(-c3ccccc3)c2)n1] |
| 74 | 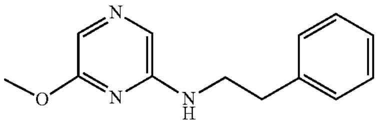 [SMILES: COc1cncc(NCCc2ccccc2)n1] |
| 75 | 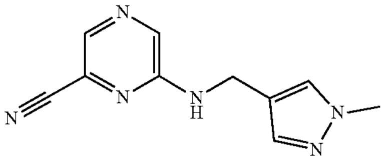 [SMILES: Cn1cc(CNc2cncc(C#N)n2)cn1] |
| 76 | 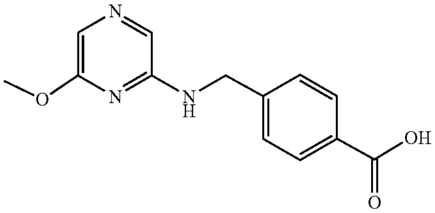 [SMILES: COc1cncc(NCc2ccc(C(=O)O)cc2)n1] |
| 77 | 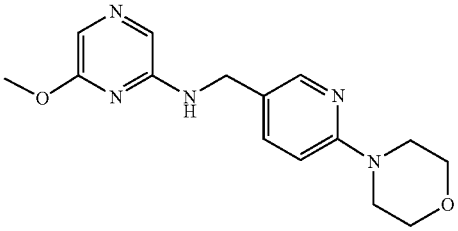 [SMILES: COc1cncc(NCc2ccc(N3CCOCC3)nc2)n1] |
| 78 | 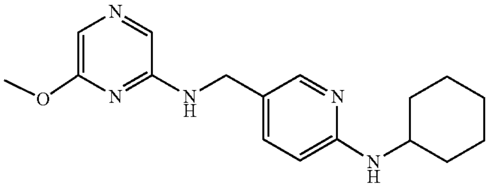 [SMILES: COc1cncc(NCc2ccc(NC3CCCCC3)nc2)n1] |

-continued
| Example | Structure |
|---|---|
| 79 | 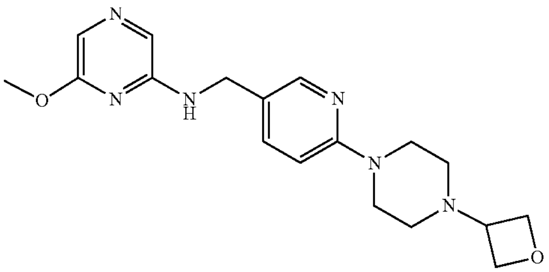 [SMILES: COc1cncc(NCc2ccc(N3CCN(C4COC4)CC3)nc2)n1] |
| 80 | 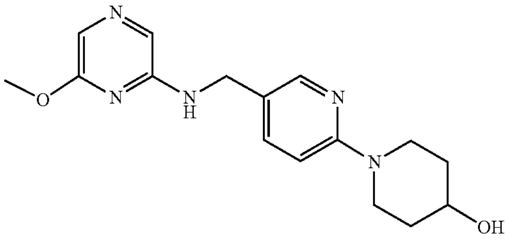 [SMILES: COc1cncc(NCc2ccc(N3CCC(O)CC3)nc2)n1] |
| 81 | 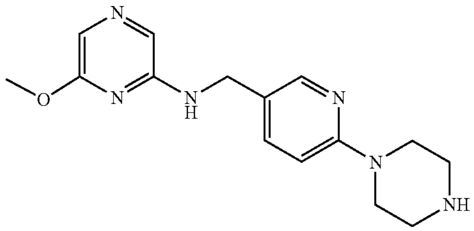 [SMILES: COc1cncc(NCc2ccc(N3CCNCC3)nc2)n1] |
| 82 | 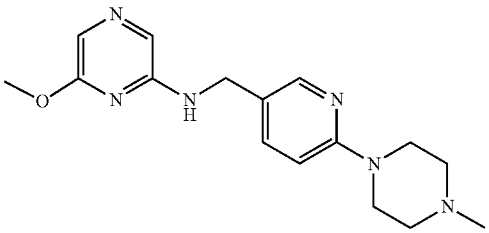 |
| 83 | 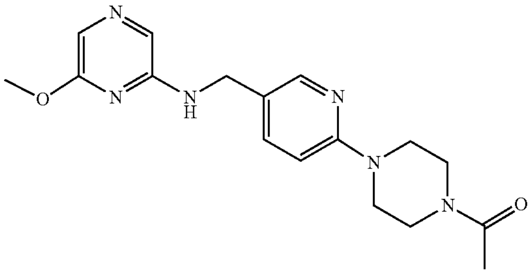 [SMILES: COc1cncc(NCc2ccc(N3CCN(C(C)=O)CC3)nc2)n1] |
| 84 | 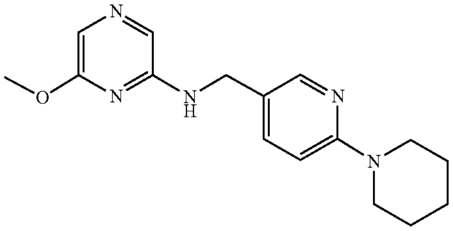 [SMILES: COc1cncc(NCc2ccc(N3CCCCC3)nc2)n1] |

-continued
| Example | Structure |
|---|---|
| 85 | 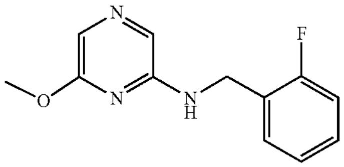 [SMILES: COc1cncc(NCc2ccccc2F)n1] |
| 86 | 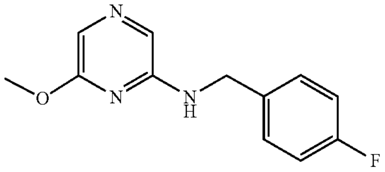 [SMILES: COc1cncc(NCc2ccc(F)cc2)n1] |
| 87 | 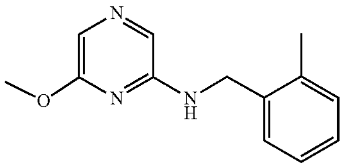 [SMILES: COc1cncc(NCc2ccccc2C)n1] |
| 88 | 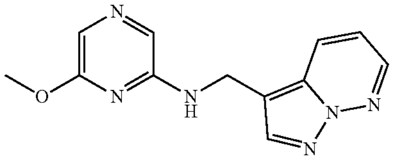 [SMILES: COc1cncc(NCc2cnn3ncccc23)n1] |
| 89 | 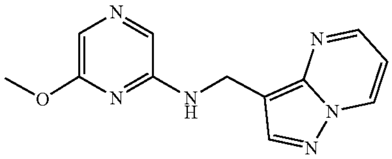 [SMILES: COc1cncc(NCc2cnn3cccnc23)n1] |
| 90 | 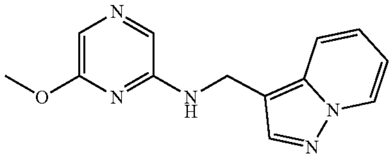 [SMILES: COc1cncc(NCc2cnn3ccccc23)n1] |
| 91 | 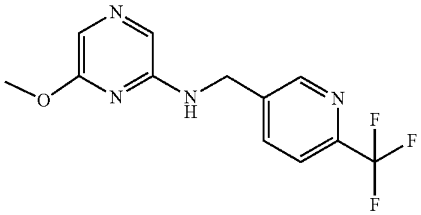 [SMILES: COc1cncc(NCc2ccc(C(F)(F)F)nc2)n1] |
| 92 | 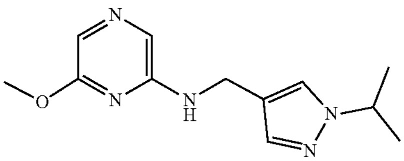 [SMILES: COc1cncc(NCc2cnn(C(C)C)c2)n1] |

-continued
| Example | Structure |
|---|---|
| 93 | 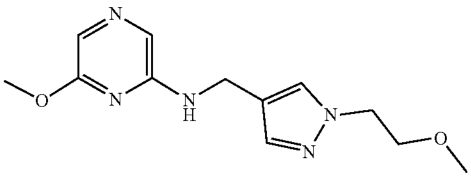 |
| 94 | 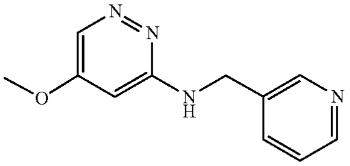 [SMILES: COc1cnnc(NCc2cccnc2)c1] |
| 95 | 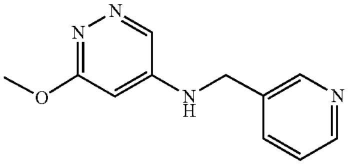 [SMILES: COc1cc(NCc2cccnc2)cnn1] |
| 96 | 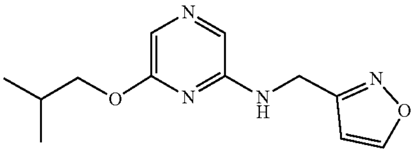 [SMILES: CC(C)COc1cncc(NCc2ccon2)n1] |
| 97 | 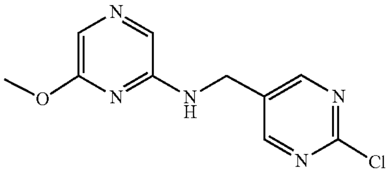 [SMILES: COc1cncc(NCc2cnc(Cl)nc2)n1] |
| 98 | 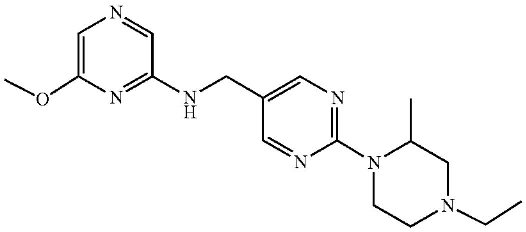 [SMILES: CCN1CCN(c2ncc(CNc3cncc(OC)n3)cn2)C(C)C1] |
| 99 | 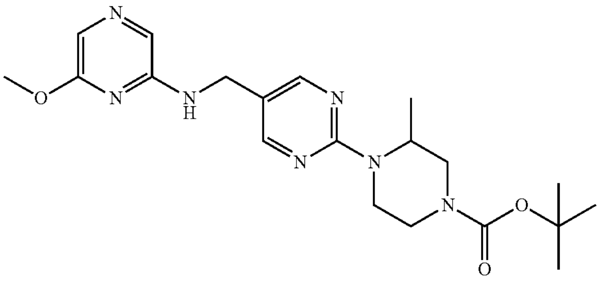 [SMILES: COc1cncc(NCc2cnc(N3CCN(C(=O)OC(C)(C)C)CC3C)nc2)n1] |

-continued
| Example | Structure |
|---|---|
| 100 | 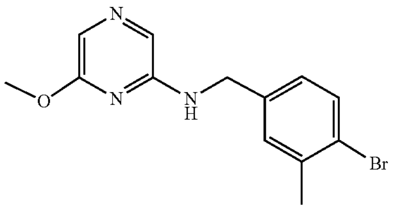 [SMILES: COc1cncc(NCc2ccc(Br)c(C)c2)n1] |
| 101 | 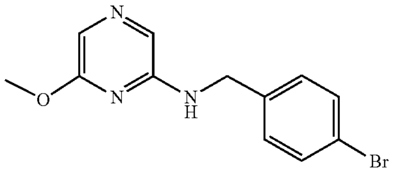 [SMILES: COc1cncc(NCc2ccc(Br)cc2)n1] |
| 102 | 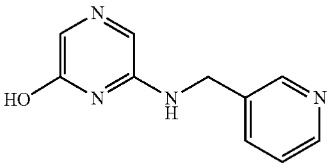 [SMILES: Oc1cncc(NCc2cccnc2)n1] |
| 103 | 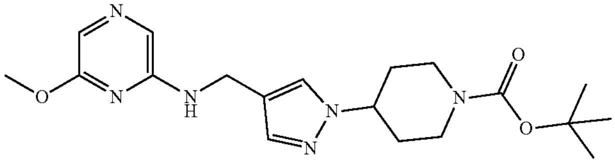 [SMILES: COc1cncc(NCc2cnn(C3CCN(C(=O)OC(C)(C)C)CC3)c2)n1] |
| 104 | 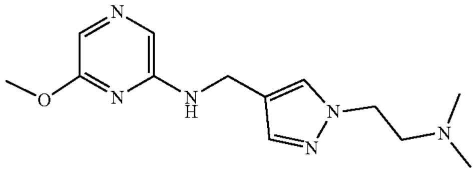 |
| 105 | 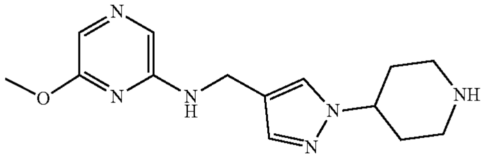 [SMILES: COc1cncc(NCc2cnn(C3CCNCC3)c2)n1] |
| 106 | 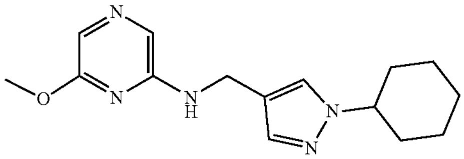 [SMILES: COc1cncc(NCc2cnn(C3CCCCC3)c2)n1] |
| 107 | 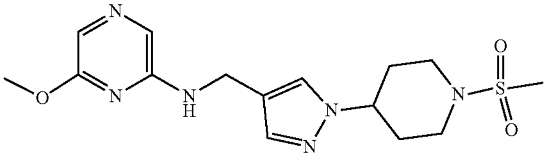 |

-continued
| Example | Structure |
|---|---|
| 108 | 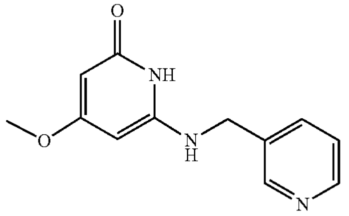 [SMILES: COc1cc(NCc2cccnc2)[nH]c(=O)c1] |
| 109 | 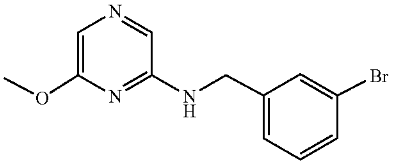 [SMILES: COc1cncc(NCc2cccc(Br)c2)n1] |
| 110 | 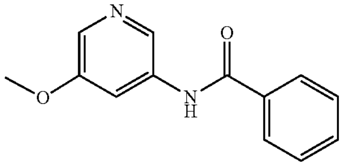 [SMILES: COc1cncc(NC(=O)c2ccccc2)c1] |
| 111 | 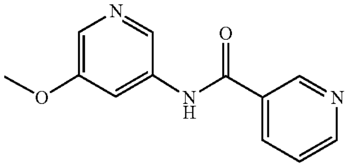 [SMILES: COc1cncc(NC(=O)c2cccnc2)c1] |
| 112 | 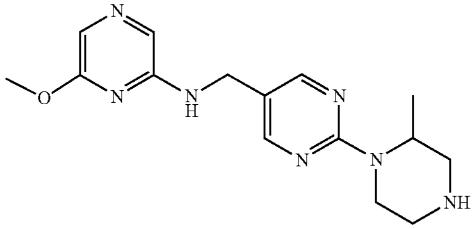 [SMILES: COc1cncc(NCc2cnc(N3CCNCC3C)nc2)n1] |
| 113 | 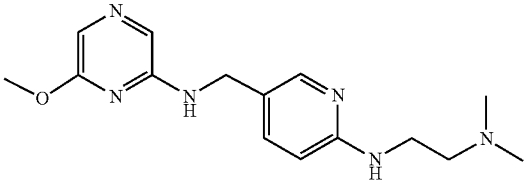 |
| 114 | 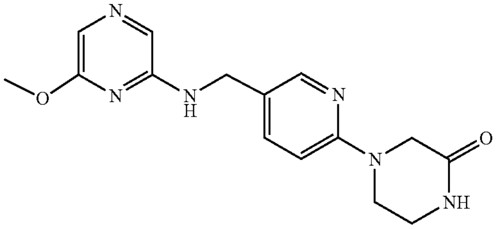 [SMILES: COc1cncc(NCc2ccc(N3CCNC(=O)C3)nc2)n1] |
| 115 | 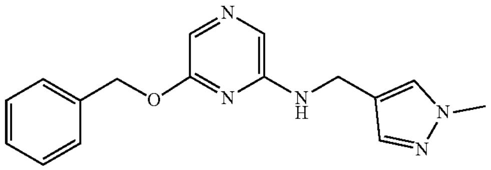 [SMILES: Cn1cc(CNc2cncc(OCc3ccccc3)n2)cn1] |

-continued
| Example | Structure |
|---|---|
| 116 | 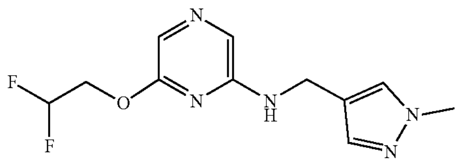 [SMILES: Cn1cc(CNc2cncc(OCC(F)F)n2)cn1] |
| 117 | 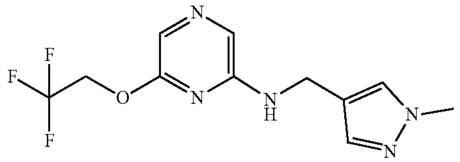 [SMILES: Cn1cc(CNc2cncc(OCC(F)(F)F)n2)cn1] |
| 118 | 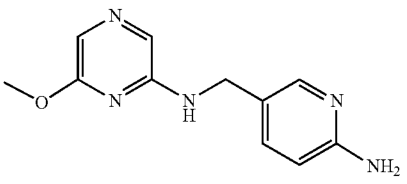 [SMILES: COc1cncc(NCc2ccc(N)nc2)n1] |
| 119 | 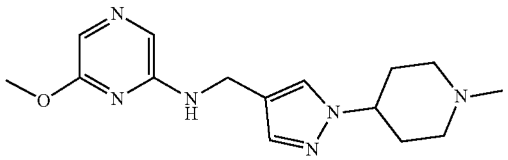 |
| 120 | 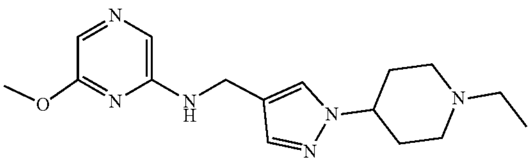 [SMILES: CCN1CCC(n2cc(CNc3cncc(OC)n3)cn2)CC1] |
| 121 | 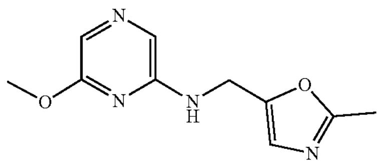 |
| 122 | 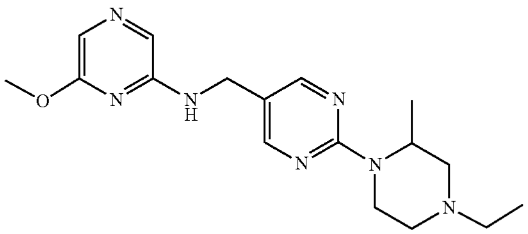 [SMILES: CCN1CCN(c2ncc(CNc3cncc(OC)n3)cn2)C(C)C1] |
| 123 | 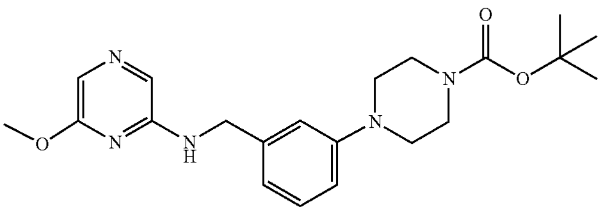 [SMILES: COc1cncc(NCc2cccc(N3CCN(C(=O)OC(C)(C)C)CC3)c2)n1] |

-continued
| Example | Structure |
|---|---|
| 124 | 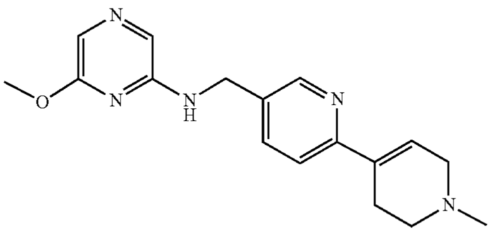 |
| 125 | 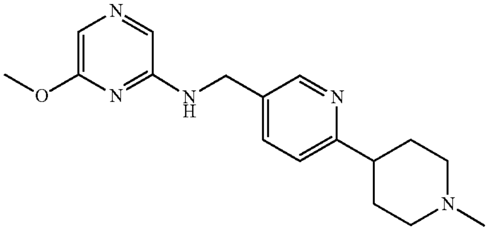 |
| 126 | 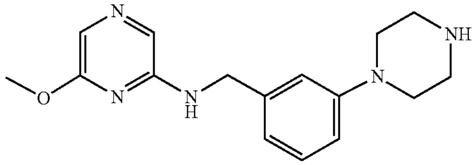 [SMILES: COc1cncc(NCc2cccc(N3CCNCC3)c2)n1] |
| 127 | 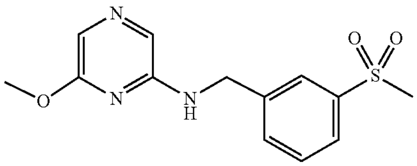 |
| 128 | 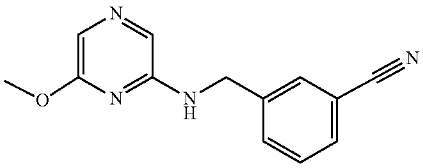 [SMILES: COc1cncc(NCc2cccc(C#N)c2)n1] |
| 129 | 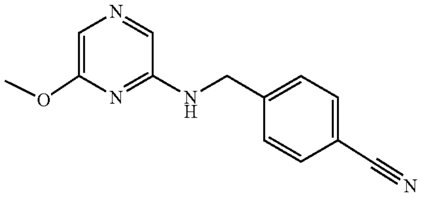 [SMILES: COc1cncc(NCc2ccc(C#N)cc2)n1] |
| 130 | 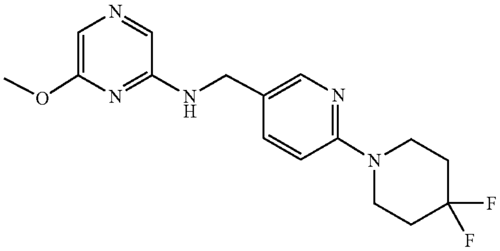 [SMILES: COc1cncc(NCc2ccc(N3CCC(F)(F)CC3)nc2)n1] |

-continued
| Example | Structure |
| --- | --- |
| 131 | 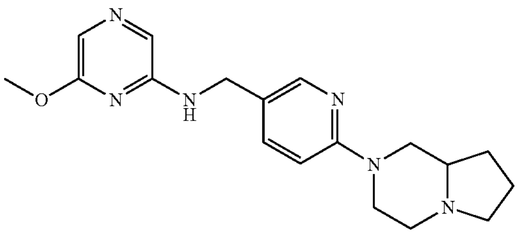 [SMILES: COc1cncc(NCc2ccc(N3CCN4CCCC4C3)nc2)n1] |
| 132 | 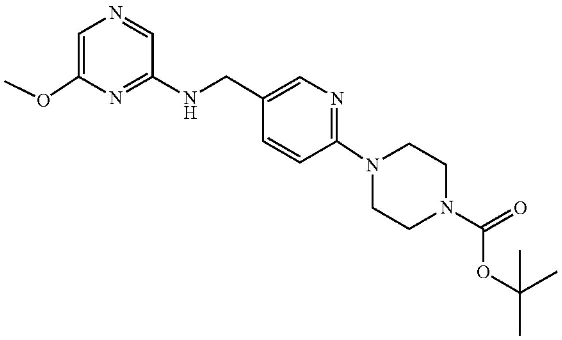 [SMILES: COc1cncc(NCc2ccc(N3CCN(C(=O)OC(C)(C)C)CC3)nc2)n1] |
| 133 | 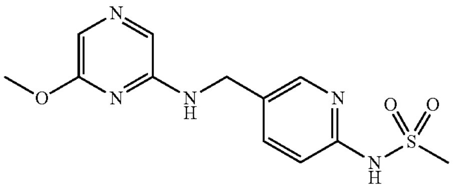 |
| 134 | 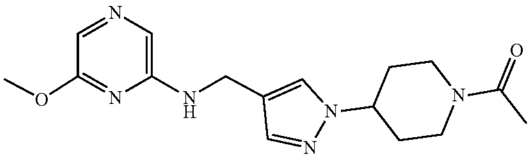 [SMILES: COc1cncc(NCc2cnn(C3CCN(C(C)=O)CC3)c2)n1] |
| 135 | 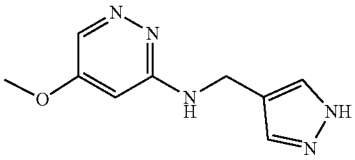 |
| 136 | 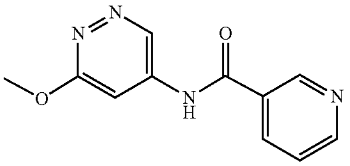 [SMILES: COc1cc(NC(=O)c2cnccn2)cnn1] |
| 137 | 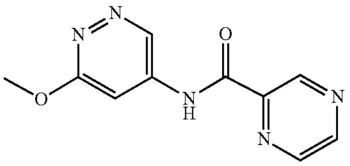 |

-continued
| Example | Structure |
| --- | --- |
| 138 | 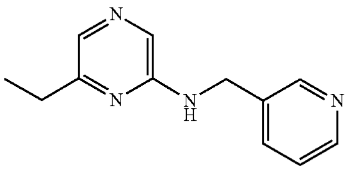 [SMILES: CCc1cncc(NCc2cccnc2)n1] |
| 139 | 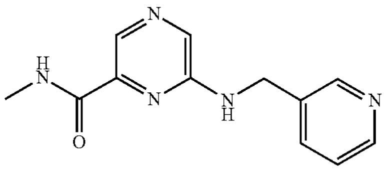 [SMILES: CNC(=O)c1cncc(NCc2cccnc2)n1] |
| 140 | 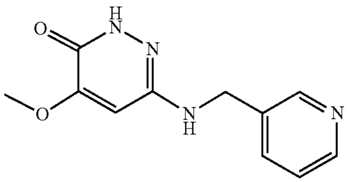 [SMILES: COc1cc(NCc2cccnc2)n[nH]c1=O] |
| 141 | 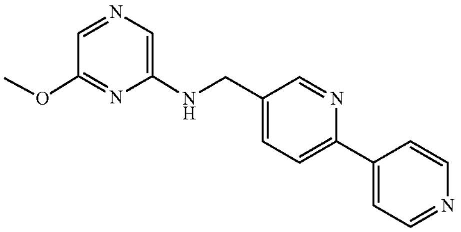 [SMILES: COc1cncc(NCc2ccc(-c3ccncc3)nc2)n1] |
| 142 | 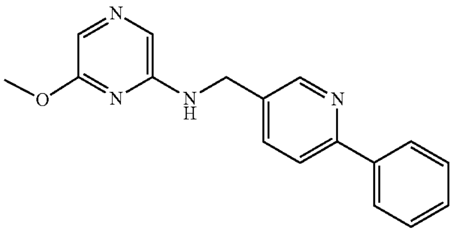 [SMILES: COc1cncc(NCc2ccc(-c3ccccc3)nc2)n1] |
| 143 | 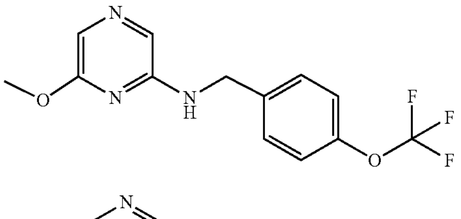 |
| 144 | 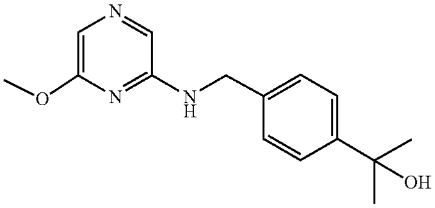 [SMILES: COc1cncc(NCc2ccc(C(C)(C)O)cc2)n1] |
| 145 | 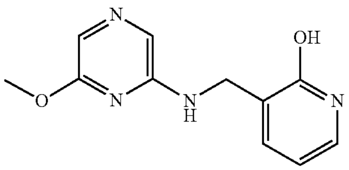 [SMILES: COc1cncc(NCc2cccnc2O)n1] |

-continued
| Example | Structure |
|---|---|
| 146 | 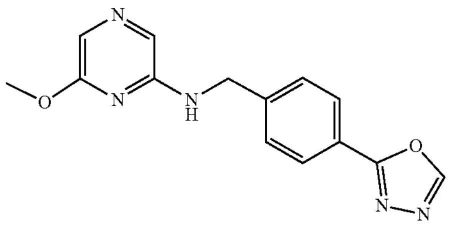 [SMILES: COc1cncc(NCc2ccc(-c3nnco3)cc2)n1] |
| 147 | 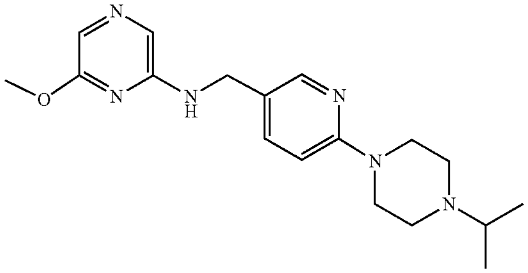 [SMILES: COc1cncc(NCc2ccc(N3CCN(C(C)C)CC3)nc2)n1] |
| 148 | 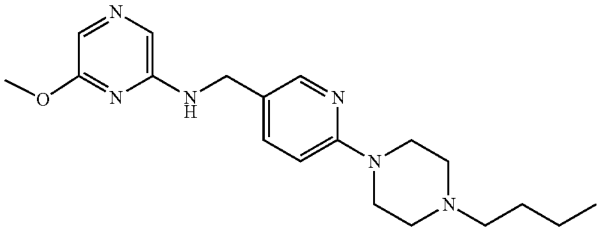 [SMILES: CCCCN1CCN(c2ccc(CNc3cncc(OC)n3)cn2)CC1] |
| 149 | 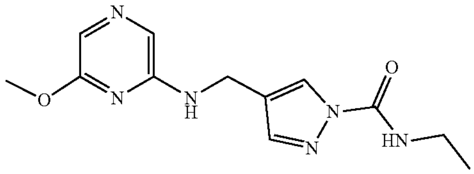 [SMILES: CCNC(=O)n1cc(CNc2cncc(OC)n2)cn1] |
| 150 | 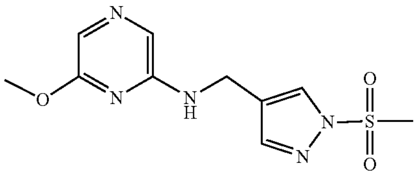 |
| 151 | 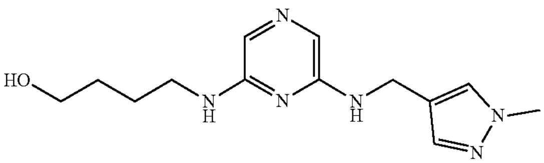 [SMILES: Cn1cc(CNc2cncc(NCCCCO)n2)cn1] |
| 152 | 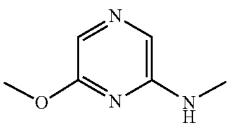 |

-continued
| Example | Structure |
|---|---|
| 153 | 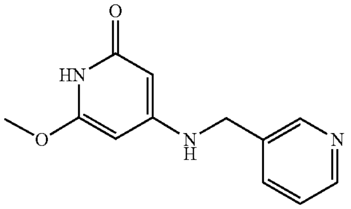 [SMILES: COc1cc(NCc2cccnc2)cc(=O)[nH]1] |
| 154 | 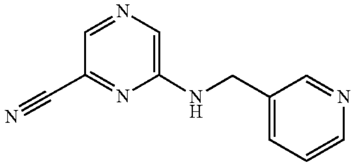 [SMILES: N#Cc1cncc(NCc2cccnc2)n1] |
| 155 | 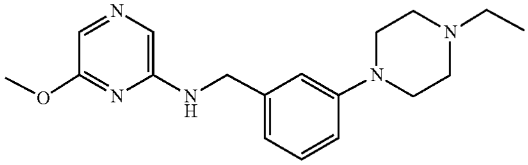 [SMILES: CCN1CCN(c2cccc(CNc3cncc(OC)n3)c2)CC1] |
| 156 | 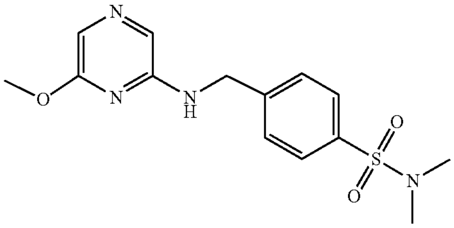 |
| 157 | 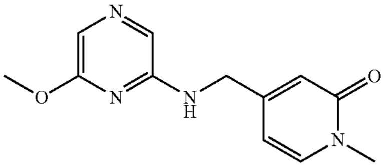 |
| 158 | 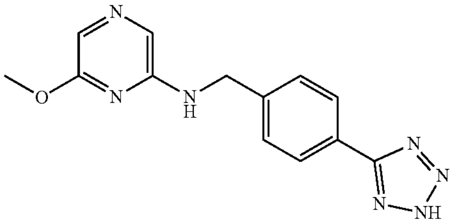 [SMILES: COc1cncc(NCc2ccc(-c3nn[nH]n3)cc2)n1] |
| 159 | 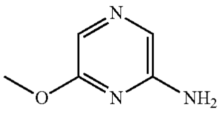 |
| 160 | 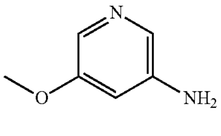 |
| 161 | 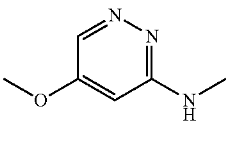 |

-continued
| Example | Structure |
|---|---|
| 162 | 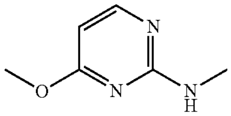 |
| 163 | 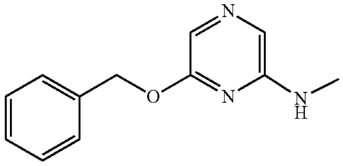 [SMILES: CNc1cncc(OCc2ccccc2)n1] |
| 164 | 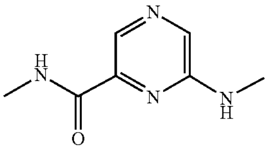 |
| 165 | 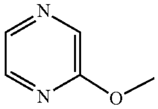 |
| 166 | 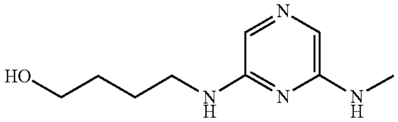 |
| 167 | 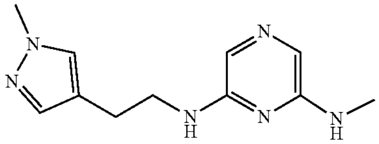 [SMILES: CNc1cncc(NCCc2cnn(C)c2)n1] |
| 168 | 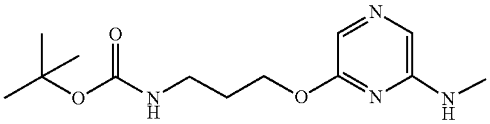 [SMILES: CNc1cncc(OCCCNC(=O)OC(C)(C)C)n1] |
| 169 | 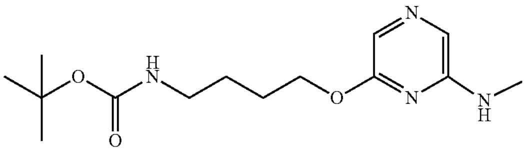 [SMILES: CNc1cncc(OCCCCNC(=O)OC(C)(C)C)n1] |
| 170 | 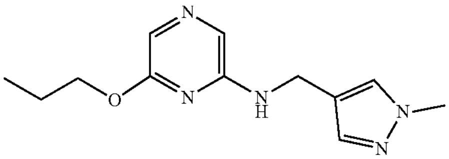 [SMILES: CCCOc1cncc(NCc2cnn(C)c2)n1] |
| 171 | 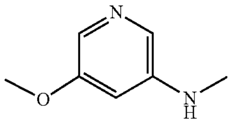 |

-continued
| Example | Structure |
| --- | --- |
| 172 | 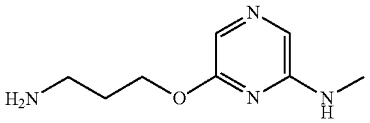 |
| 173 | 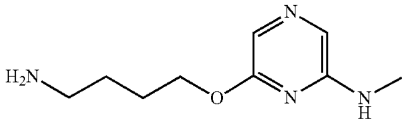 |
| 174 | 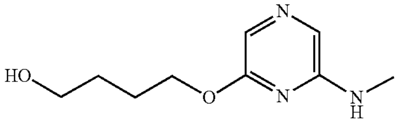 |
| 175 | 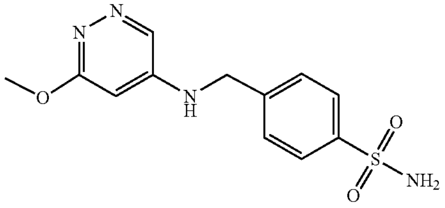 [SMILES: COc1cc(NCc2ccc(S(N)(=O)=O)cc2)cnn1] |
| 176 | 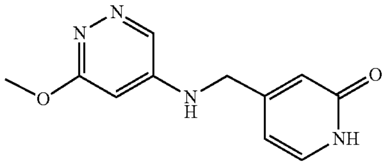 [SMILES: COc1cc(NCc2cc[nH]c(=O)c2)cnn1] |
| 177 | 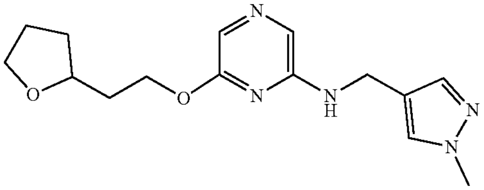 [SMILES: Cn1cc(CNc2cncc(OCCC3CCCO3)n2)cn1] |
| 178 | 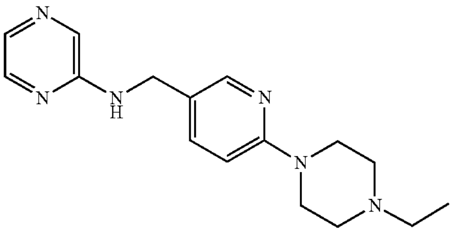 [SMILES: CCN1CCN(c2ccc(CNc3cnccn3)cn2)CC1] |
| 179 | 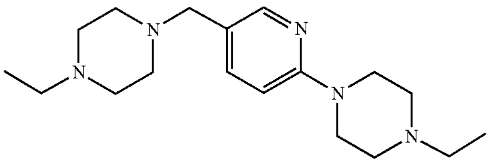 [SMILES: CCN1CCN(Cc2ccc(N3CCN(CC)CC3)nc2)CC1] |

-continued
| Example | Structure |
|---|---|
| 180 | 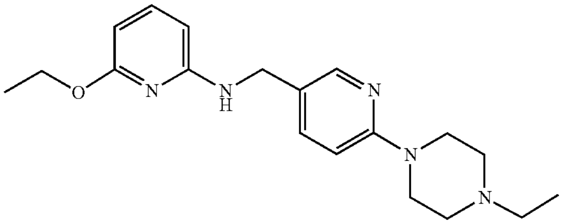 [SMILES: CCOc1cccc(NCc2ccc(N3CCN(CC)CC3)nc2)n1] |
| 181 | 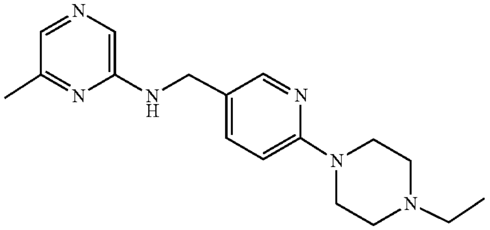 [SMILES: CCN1CCN(c2ccc(CNc3cncc(C)n3)cn2)CC1] |
| 182 | 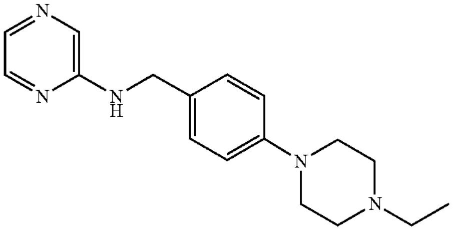 [SMILES: CCN1CCN(c2ccc(CNc3cnccn3)cc2)CC1] |
| 183 | 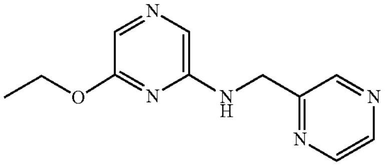 [SMILES: CCOc1cncc(NCc2cnccn2)n1] |
| 184 | 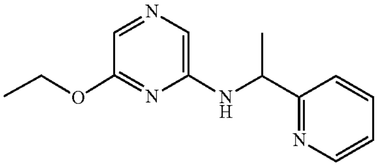 [SMILES: CCOc1cncc(NC(C)c2ccccn2)n1] |
| 185 | 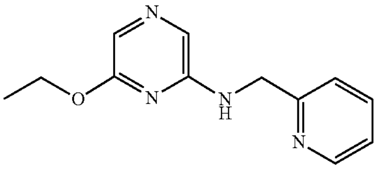 [SMILES: CCOc1cncc(NCc2ccccn2)n1] |
| 186 | 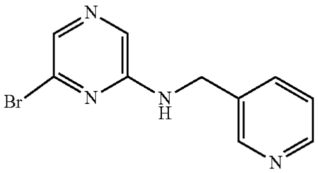 [SMILES: Brc1cncc(NCc2cccnc2)n1] |
| 187 | 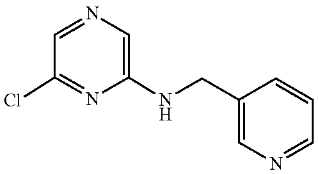 |

-continued
| Example | Structure |
| --- | --- |
| 188 | 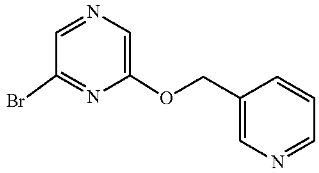 [SMILES: Brc1cncc(OCc2cccnc2)n1] |
| 189 | 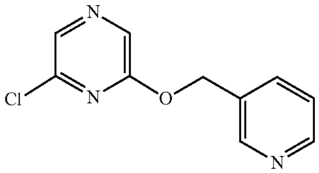 [SMILES: Clc1cncc(OCc2cccnc2)n1] |
| 190 | 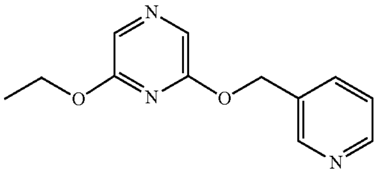 [SMILES: CCOc1cncc(OCc2cccnc2)n1] |
| 191 | 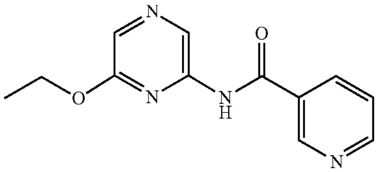 [SMILES: CCOc1cncc(NC(=O)c2cccnc2)n1] |
| 192 | 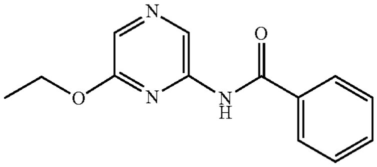 [SMILES: CCOc1cncc(NC(=O)c2ccccc2)n1] |
| 193 | 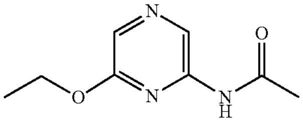 |
| 194 | 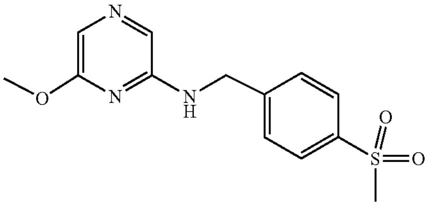 [SMILES: COc1cncc(NCc2ccc(S(C)(=O)=O)cc2)n1] |
| 195 | 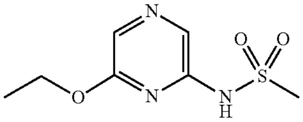 |
| 196 | 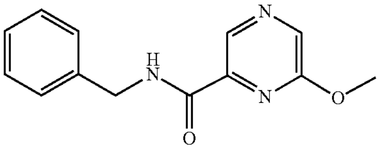 [SMILES: COc1cncc(C(=O)NCc2ccccc2)n1] |

-continued
| Example | Structure |
|---|---|
| 197 | 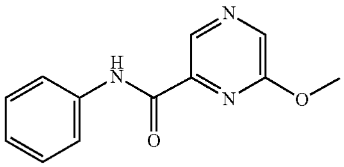 [SMILES: COc1cncc(C(=O)Nc2ccccc2)n1] |
| 198 | 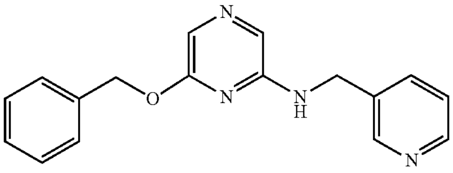 [SMILES: c1ccc(COc2cncc(NCc3cccnc3)n2)cc1] |
| 199 | 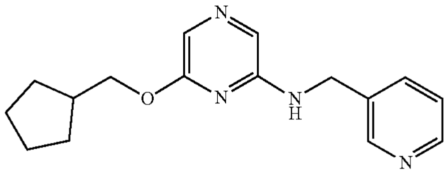 [SMILES: c1cncc(CNc2cncc(OCC3CCCC3)n2)c1] |
| 200 | 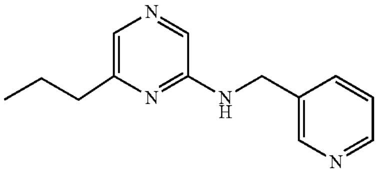 [SMILES: CCCc1cncc(NCc2cccnc2)n1] |
| 201 | 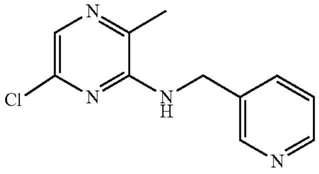 [SMILES: Cc1ncc(Cl)nc1NCc1cccnc1] |
| 202 | 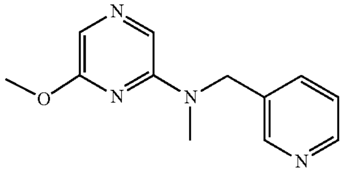 [SMILES: COc1cncc(N(C)Cc2cccnc2)n1] |
| 203 | 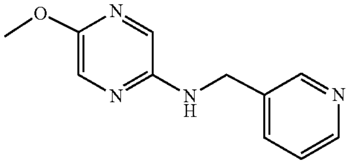 [SMILES: COc1cnc(NCc2cccnc2)cn1] |
| 204 | 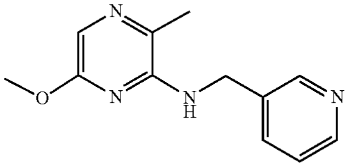 [SMILES: COc1cnc(C)c(NCc2cccnc2)n1] |

-continued
| Example | Structure |
| --- | --- |
| 205 | 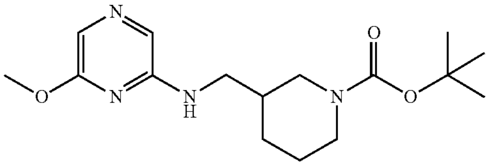 [SMILES: COc1cncc(NCC2CCCN(C(=O)OC(C)(C)C)C2)n1] |
| 206 | 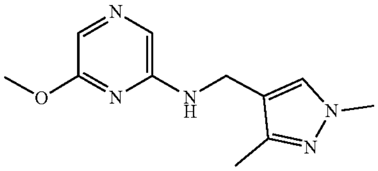 |
| 207 | 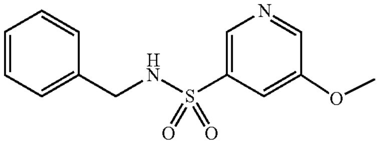 [SMILES: COc1cncc(S(=O)(=O)NCc2ccccc2)c1] |
| 208 | 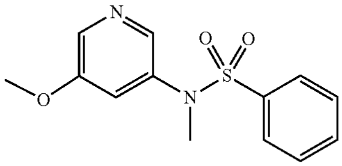 [SMILES: COc1cncc(N(C)S(=O)(=O)c2ccccc2)c1] |
| 209 | 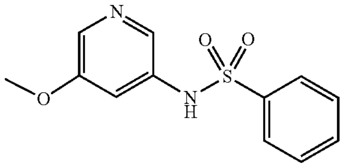 [SMILES: COc1cncc(NS(=O)(=O)c2ccccc2)c1] |
| 210 | 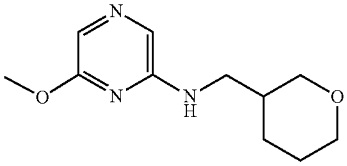 |
| 211 | 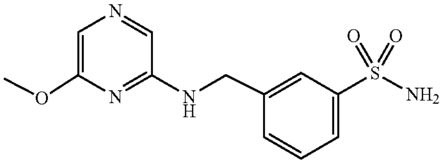 [SMILES: COc1cncc(NCc2cccc(S(N)(=O)=O)c2)n1] |
| 212 | 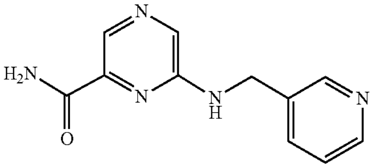 [SMILES: NC(=O)c1cncc(NCc2cccnc2)n1] |
| 213 | 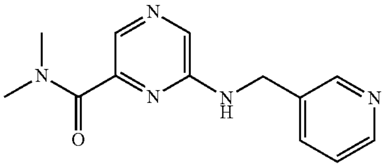 [SMILES: CN(C)C(=O)c1cncc(NCc2cccnc2)n1] |

-continued
| Example | Structure |
|---|---|
| 214 | 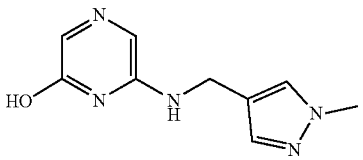 |
| 215 | 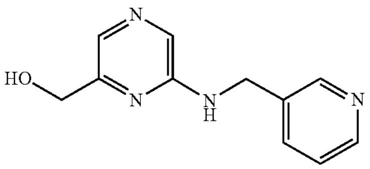 [SMILES: OCc1cncc(NCc2cccnc2)n1] |
| 216 | 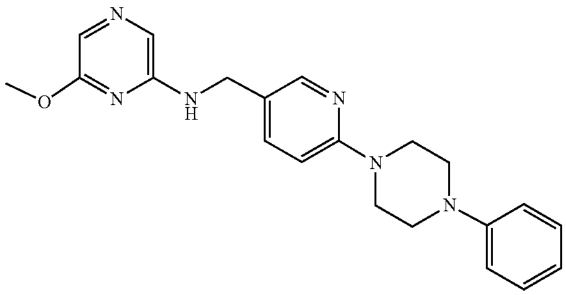 [SMILES: COc1cncc(NCc2ccc(N3CCN(c4ccccc4)CC3)nc2)n1] |
| 217 | 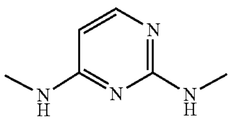 |
| 218 | 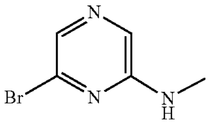 |
| 219 | 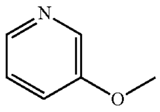 |
| 220 | 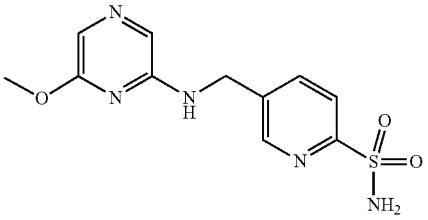 [SMILES: COc1cncc(NCc2ccc(S(N)(=O)=O)nc2)n1] |
| 221 | 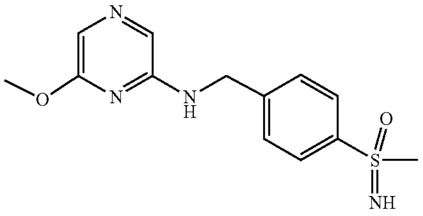 |

-continued
| Example | Structure |
| --- | --- |
| 222 | 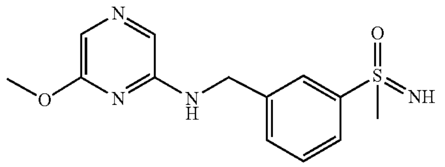 [SMILES: COc1cncc(NCc2cccc(S(C)(=N)=O)c2)n1] |
| 223 | 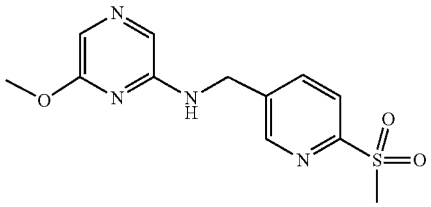 |
| 224 | 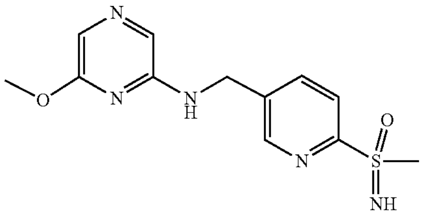 |
| 225 | 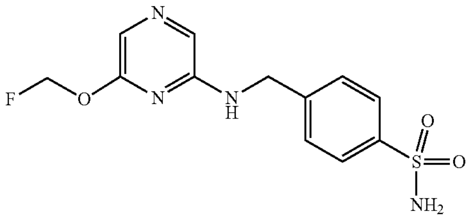 [SMILES: NS(=O)(=O)c1ccc(CNc2cncc(OCF)n2)cc1] |
| 226 | 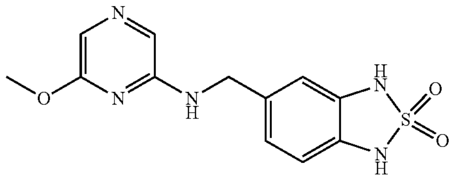 [SMILES: COc1cncc(NCc2ccc3c(c2)NS(=O)(=O)N3)n1] |
| 227 | 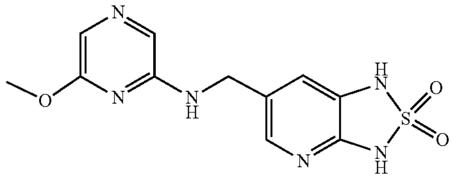 [SMILES: COc1cncc(NCc2cnc3c(c2)NS(=O)(=O)N3)n1] |
| 228 | 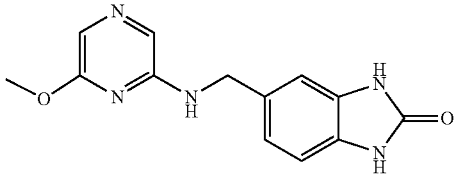 [SMILES: COc1cncc(NCc2ccc3[nH]c(=O)[nH]c3c2)n1] |
| 229 | 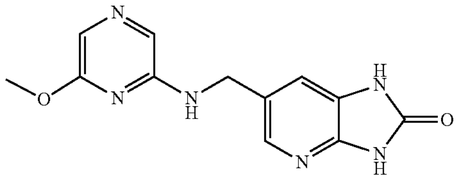 [SMILES: COc1cncc(NCc2cnc3[nH]c(=O)[nH]c3c2)n1] |

-continued

| Example | Structure |
|---|---|
| 230 | 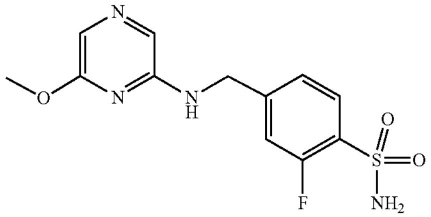 [SMILES: COc1cncc(NCc2ccc(S(N)(=O)=O)c(F)c2)n1] |
| 231 | 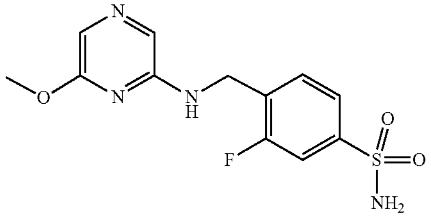 [SMILES: COc1cncc(NCc2ccc(S(N)(=O)=O)cc2F)n1] |

In some aspects, the present disclosure provides a compound according to the following embodiments:

Embodiment 1. A compound of Formula I:

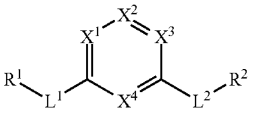

I or a pharmaceutically acceptable salt thereof, wherein:

$X^1$ is N or C—$R^{x1}$;

$X^2$ is N or C—$R^{x2}$ $X^3$ is N or C—$R^{x3}$;

$X^4$ is N or C—$R^{x4}$;

provided that one or two of $X^1$, $X^2$, $X^3$ and $X^4$ is N;

each of RX, $R^{x2}$, $R^{x3}$, and $R^{x4}$ is independently selected from —R or —OR;

$L^1$ is selected from a covalent bond, —O—, —N(R)—, —C(O)N(R)—, —$S(O)_2$—, and —$S(O)_2N(R)$—;

$L^2$ is selected from a covalent bond, —O—, —N(R)—, —N(R)C(O)—, and —$N(R)S(O)_2$-;

$R^1$ is selected from halogen, CN, and —R;

$R^2$ is —R; and

R is selected from hydrogen or an optionally substituted group selected from $C_{1-6}$ aliphatic, phenyl, a 4- to 6-membered heterocyclic ring having 1-2 heteroatoms independently selected from nitrogen, oxygen, or sulfur, a 5- to 6-membered heteroaryl ring having 1-3 heteroatoms independently selected from nitrogen, oxygen, or sulfur, and an 8- to 10-membered heteroaryl ring having 1-3 heteroatoms independently selected from nitrogen, oxygen, or sulfur.

Embodiment 2. The compound according to embodiment 1, wherein $X^1$ is N.

Embodiment 3. The compound according to embodiment 1, wherein $X^2$ is N.

Embodiment 4. The compound according to embodiment 1, wherein $X^3$ is N.

Embodiment 5. The compound according to embodiment 1, wherein $X^4$ is N.

Embodiment 6. The compound according to any one of embodiments 1-4, wherein $X^4$ is N.

Embodiment 7. The compound according to any one of embodiments 3-5, wherein $X^1$ is N.

Embodiment 8. The compound according to any one of embodiments 2, 4, and 5, wherein $X^2$ is N.

Embodiment 9. The compound according to any one of embodiments 2, 3, and 5, wherein $X^3$ is N.

Embodiment 10. The compound according to any one of embodiments 1-9, wherein the compound is selected from the group consisting of:

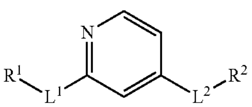 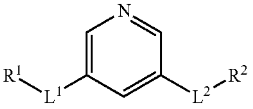

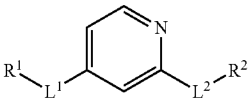 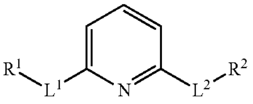

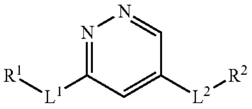 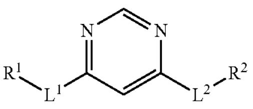

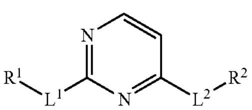 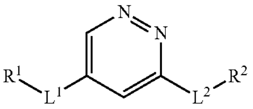

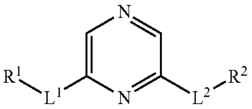 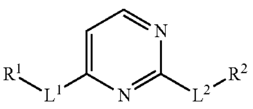

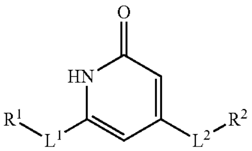 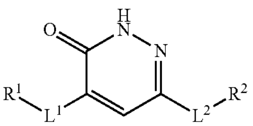

-continued

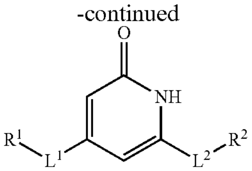

Embodiment 11. The compound according to any one of embodiments 1-10, wherein $L^1$ is —O—.

Embodiment 12. The compound according to embodiment 11, wherein $R^1$ is optionally substituted $C_{1-6}$ aliphatic.

Embodiment 13. The compound according to embodiment 12, wherein $R^1$ is $C_{1-6}$ aliphatic optionally substituted with a group selected from halogen, $—(CH_2)_{0-4}R°$, $—(CH_2)_{0-4}OR°$, $—(CH_2)_{0-4}N(R°)_2$, or $—(CH_2)_{0-4}N(R°)CO_2R°$.

Embodiment 14. The compound according to embodiment 13, wherein $R^1$ is $—CH_2—R°$, $—CH_2—OR°$, $—CH_2—N(R°)_2$, or $—CH_2—N(R°)CO_2R°$.

Embodiment 15. The compound according to embodiment 13, wherein $R^1$ is $—CH_2CH_2—R°$, $—CH_2CH_2—OR°$, $—CH_2CH_2—N(R°)_2$, or $—CH_2CH_2—N(R°)CO_2R°$.

Embodiment 16. The compound according to embodiment 13, wherein $R^1$ is $—(CH_2)_3—R°$, $—(CH_2)_3—OR°$, $—(CH_2)_3—N(R°)_2$, or $—(CH_2)_3—N(R°)CO_2R°$.

Embodiment 17. The compound according to embodiment 13, wherein $R^1$ is $—(CH_2)_4—R°$, $—(CH_2)_4—OR°$, $—(CH_2)_4—N(R°)_2$, or $—(CH_2)_4—N(R°)CO_2R°$.

Embodiment 18. The compound according to embodiment 13, wherein $R^1$ is $C_{1-6}$ aliphatic optionally substituted with —R°, wherein R° is selected from:

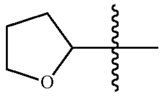 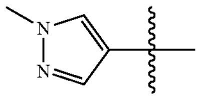 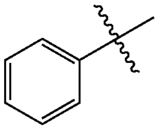

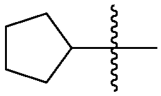

Embodiment 19. The compound according to any one of embodiments 11-13, wherein $R^1$ is selected from hydrogen, $—CH_3$, $—CH_2F$, $—CH_2CH_3$, $—CH_2CF_3$, $—CH_2CHF_2$, $—CH_2CH_2CH_3$, $—CH(CH_3)_2$, $—(CH_2)_4CH_3$, $—CH_2CH(CH_3)_2$, or a group selected from

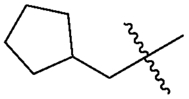 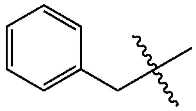

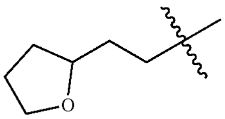 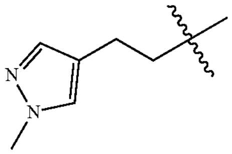

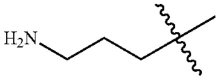 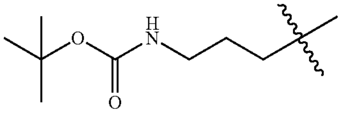

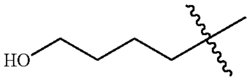 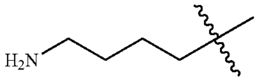

-continued

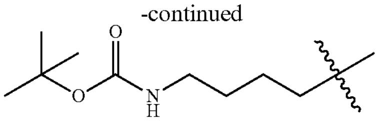

Embodiment 20. The compound according to any one of embodiments 1-10, wherein $L^1$ is a covalent bond.

Embodiment 21. The compound according to embodiment 20, wherein $R^1$ is halogen.

Embodiment 22. The compound according to embodiment 20, wherein $R^1$ is hydrogen.

Embodiment 23. The compound according to embodiment 20, wherein $R^1$ is —CN.

Embodiment 24. The compound according to embodiment 20, wherein $R^1$ is optionally substituted $C_{1-6}$ aliphatic.

Embodiment 25. The compound according to embodiment 20, wherein $R^1$ is selected from hydrogen, chloro, bromo, —CN, $—CH_3$, $—CH_2CH_3$, $—CH_2CH_2CH_3$,

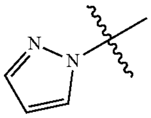 , or 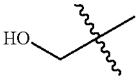 .

Embodiment 26. The compound according to any one of embodiments 1-10, wherein $L^1$ is —C(O)N(R)—.

Embodiment 27. The compound according to embodiment 26, wherein R is hydrogen.

Embodiment 28. The compound according to embodiment 26, wherein R is $—CH_3$.

Embodiment 29. The compound according to any one of embodiments 26-28, wherein $R^1$ is selected from hydrogen, $—CH_3$, phenyl,

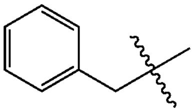 , or 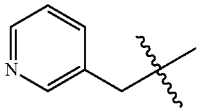 .

Embodiment 30. The compound according to any one of embodiments 1-10, wherein $L^1$ is $—S(O)_2$-.

Embodiment 31. The compound according to embodiment 30, wherein $R^1$ is $—CH_3$.

Embodiment 32. The compound according to any one of embodiments 1-10, wherein $L^1$ is $—S(O)_2N(R)—$.

Embodiment 33. The compound according to embodiment 32, wherein R is hydrogen.

Embodiment 34. The compound according to embodiment 32, wherein R is $—CH_3$.

Embodiment 35. The compound according to any one of embodiments 32-34, wherein $R^1$ is phenyl or

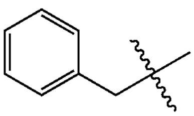 .

Embodiment 36. The compound according to any one of embodiments 1-10, wherein $L^1$ is —N(R)—.

Embodiment 37. The compound according to embodiment 36, wherein R is hydrogen.

Embodiment 38. The compound according to embodiment 36, wherein R is —$CH_3$.

Embodiment 39. The compound according to any one of embodiments 36-38, wherein $R^1$ is optionally substituted CI-6 aliphatic.

Embodiment 40. The compound according to embodiment 39, wherein $R^1$ is selected from —$CH_3$, —$CH_2CH_3$,

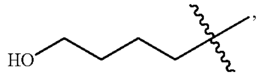, and 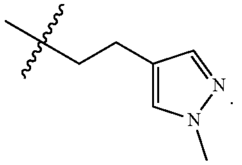.

Embodiment 41. The compound according to any one of embodiments 1-40, wherein $L^2$ is —N(R)—.

Embodiment 42. The compound according to embodiment 41, wherein R is hydrogen.

Embodiment 43. The compound according to embodiment 41, wherein R is —$CH_3$.

Embodiment 44. The compound according to embodiment 42, wherein $R^2$ is hydrogen.

Embodiment 45. The compound according to any one of embodiments 41-43, wherein $R^2$ is optionally substituted $C_{1-6}$ aliphatic.

Embodiment 46. The compound according to embodiment 45, wherein $R^2$ is $C_{1-6}$ aliphatic optionally substituted with halogen.

Embodiment 47. The compound according to embodiment 45, wherein $R^2$ is $C_{1-6}$ aliphatic optionally substituted with —R°, wherein R° is selected from:

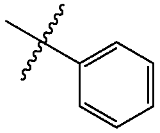 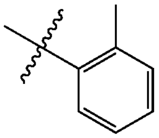 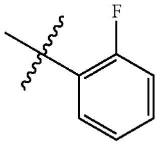

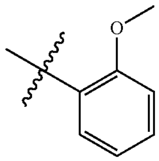 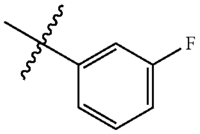

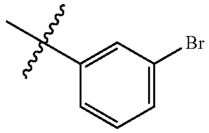 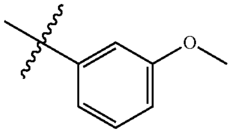

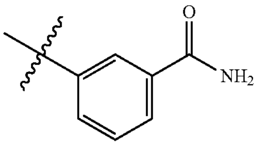 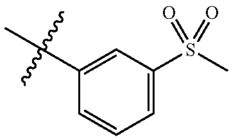

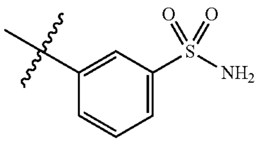 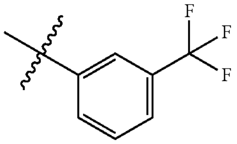

-continued

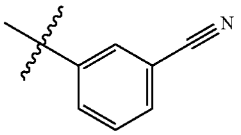 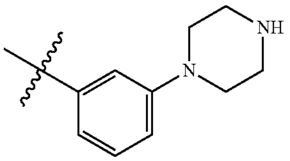

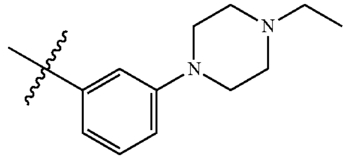

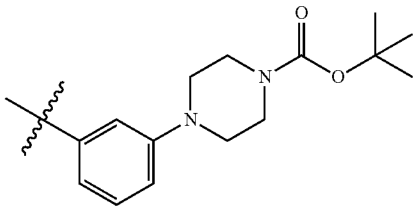

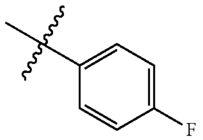 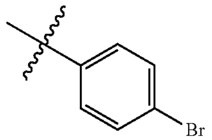

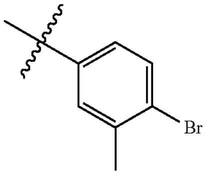 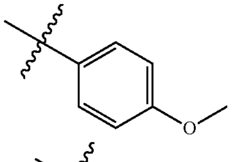

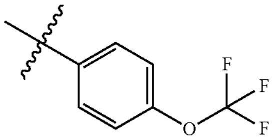 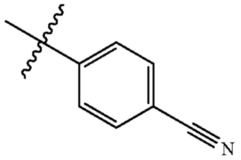

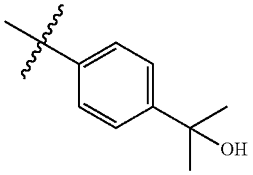 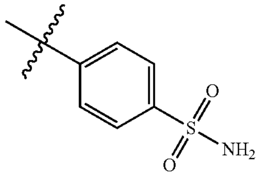

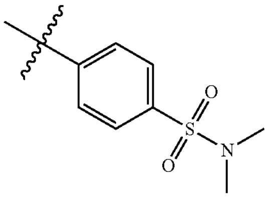 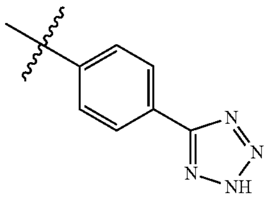

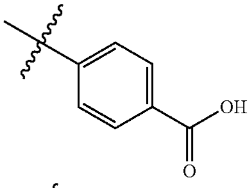 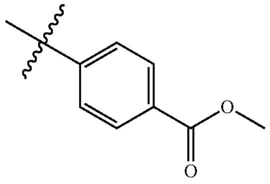

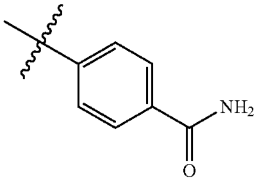 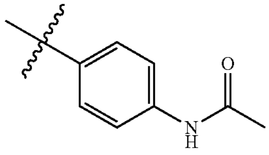

-continued
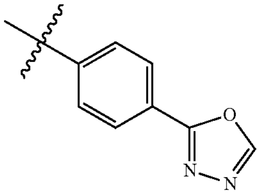
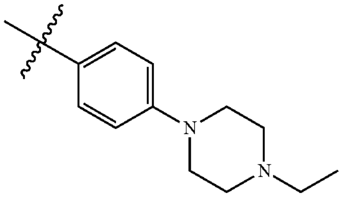
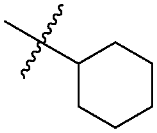
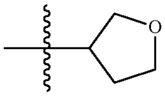
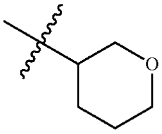
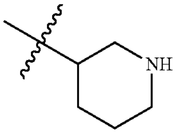
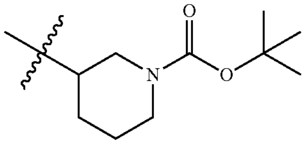
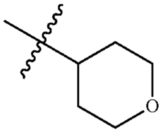
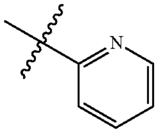
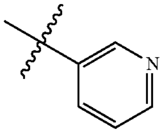
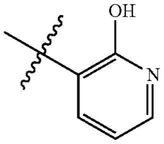
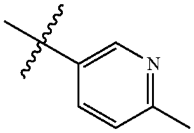
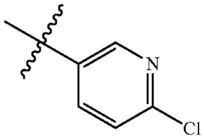
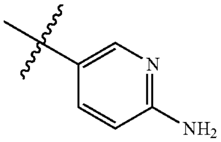
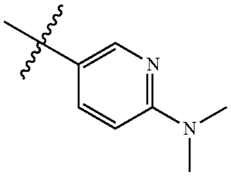
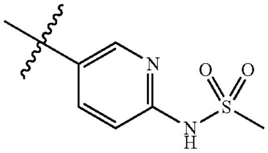
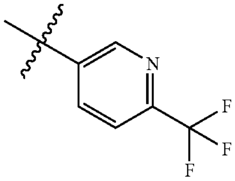
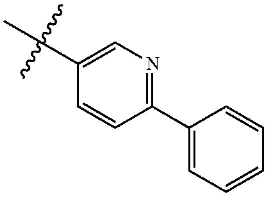
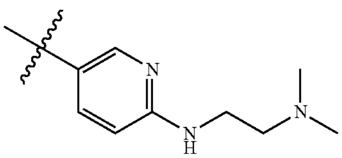
-continued
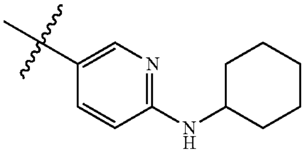
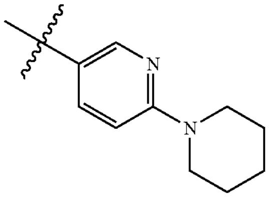
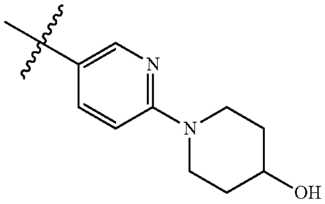
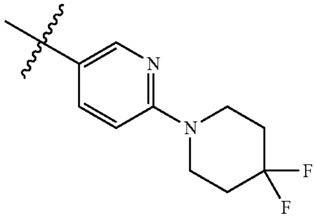
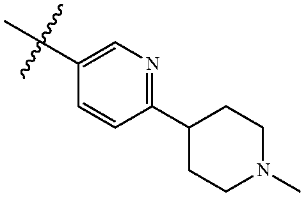
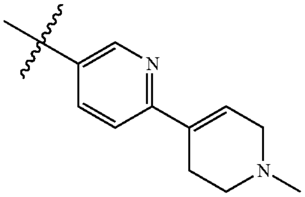
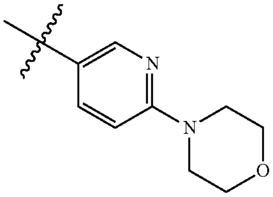
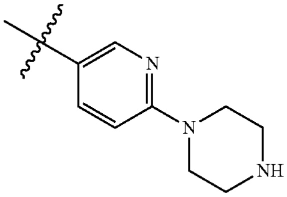
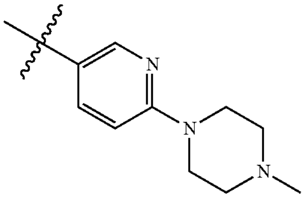

-continued
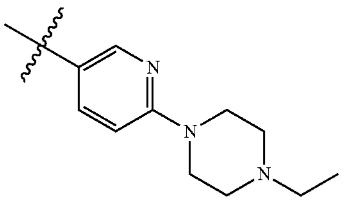
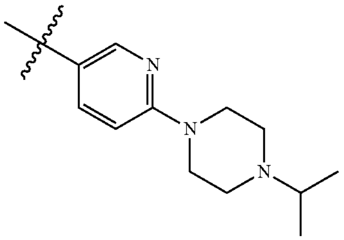
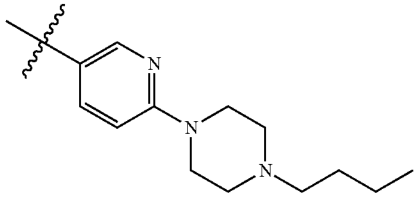
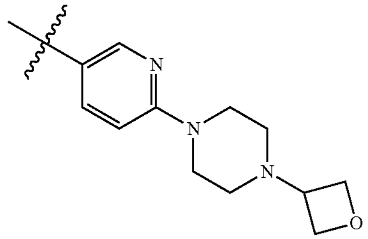
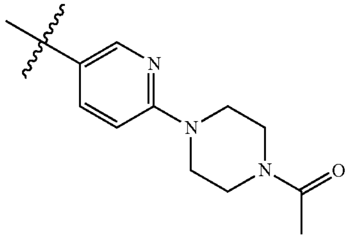
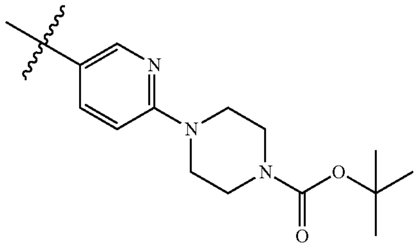
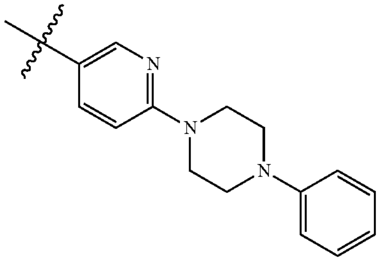
-continued
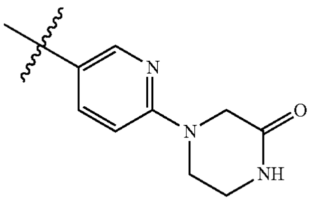
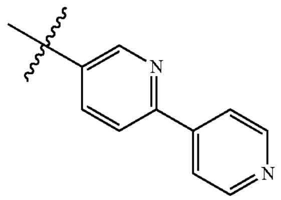
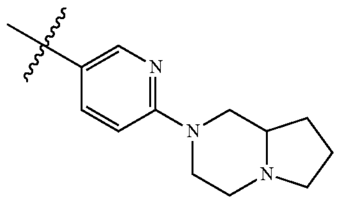
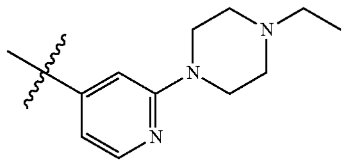
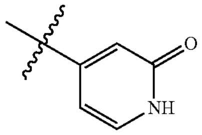
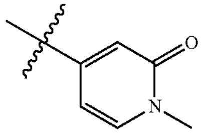
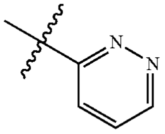
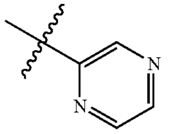
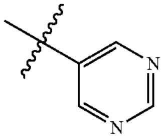
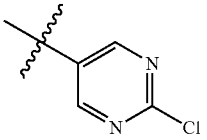
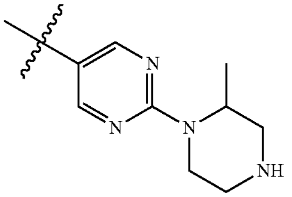
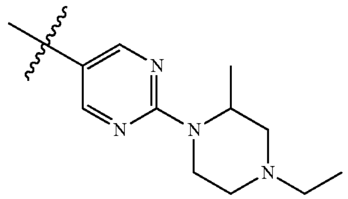
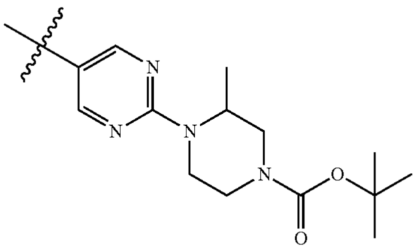

-continued
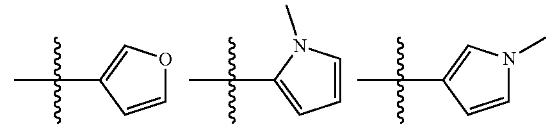
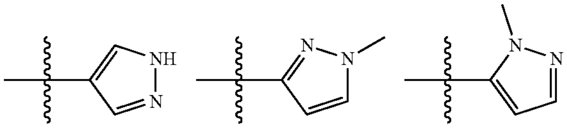
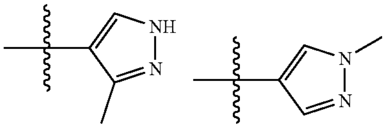
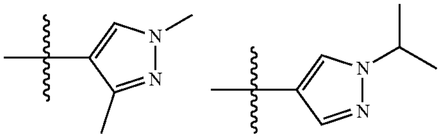
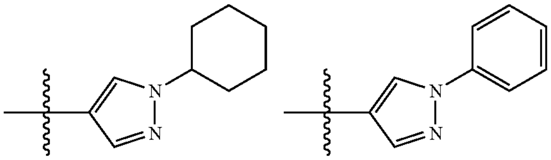
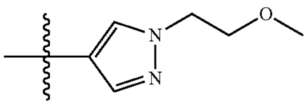
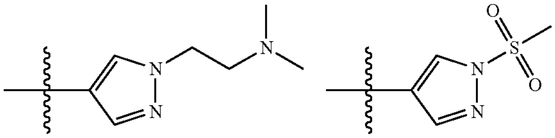
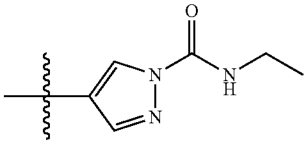
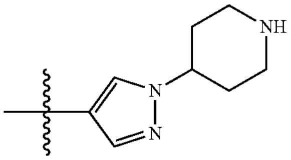
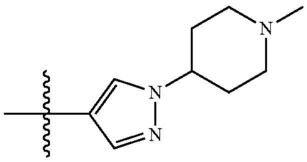
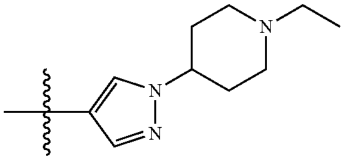
-continued
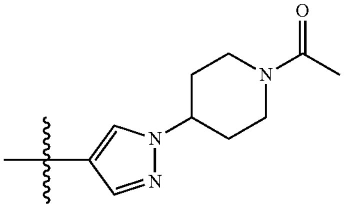
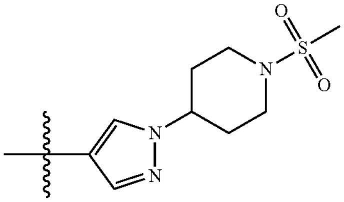
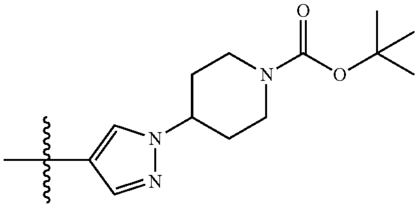
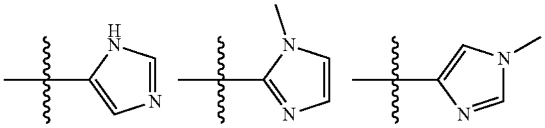
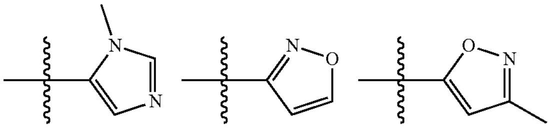
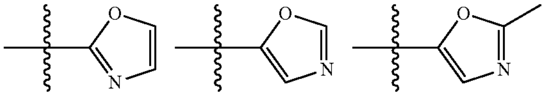
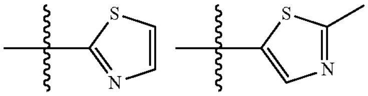
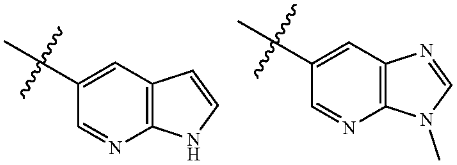
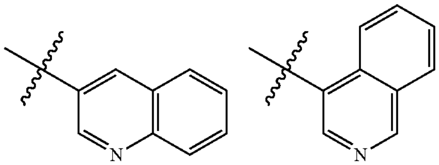
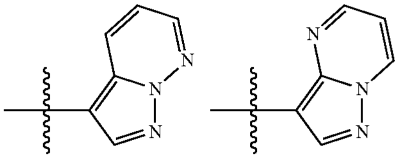
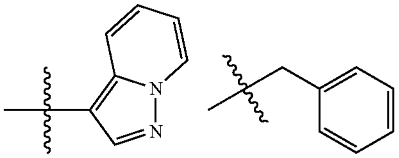

-continued

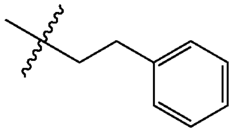

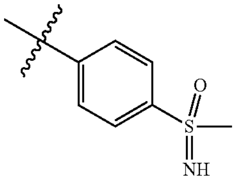

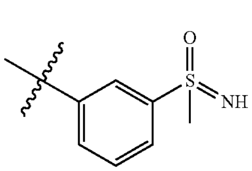

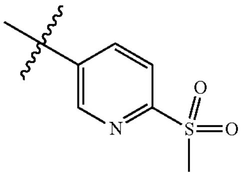

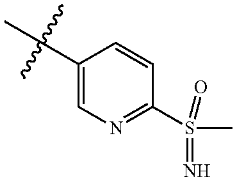

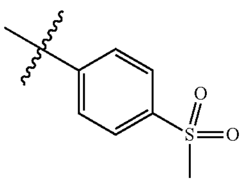

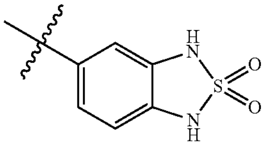

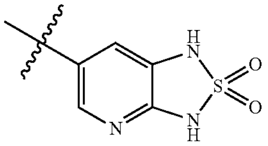

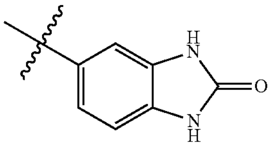

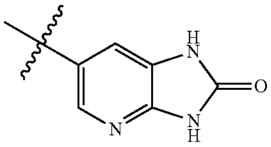

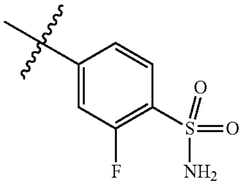

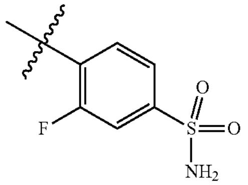

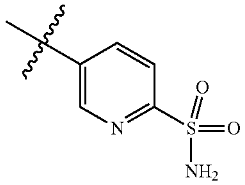

Embodiment 48. The compound according to any one of embodiments 1-40, wherein $L^2$ is a covalent bond.

Embodiment 49. The compound according to embodiment 48, wherein $R^2$ is optionally substituted $C_{1-6}$ aliphatic.

Embodiment 50. The compound according to embodiment 49, wherein $R^2$ is

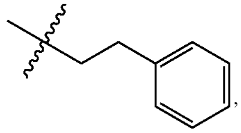,

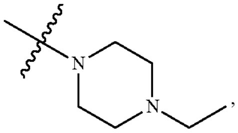, or

-continued

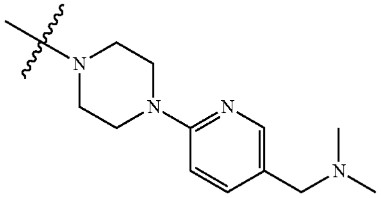.

Embodiment 51. The compound according to any one of embodiments 1-40, wherein $L^2$ is —O—.

Embodiment 52. The compound according to embodiment 51, wherein $R^2$ is $—CH_3$.

Embodiment 53. The compound according to embodiment 51, wherein $R^2$ is

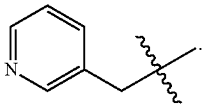 [SMILES: *Cc1cccnc1].

Embodiment 54. The compound according to any one of embodiments 1-40, wherein $L^2$ is —N(R)C(O)—.

Embodiment 55. The compound according to embodiment 54, wherein R is hydrogen.

Embodiment 56. The compound according to embodiment 54, wherein R is $—CH_3$.

Embodiment 57. The compound according to any one of embodiments 54-56, wherein $R^2$ is $—CH_3$, phenyl,

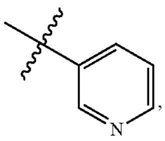,

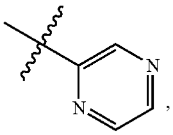,

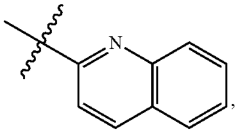, or

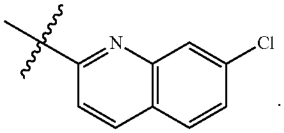.

Embodiment 58. The compound according to any one of embodiments 1-40, wherein $L^2$ is $—N(R)S(O)_2$-.

Embodiment 59. The compound according to embodiment 58, wherein R is hydrogen.

Embodiment 60. The compound according to embodiment 58, wherein R is $—CH_3$.

Embodiment 61. The compound according to any one of embodiments 58-60, wherein $R^2$ is $—CH_3$, phenyl, or

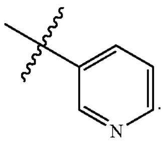.

Embodiment 62. The compound according to embodiment 1, wherein the compound is selected from:

I-a

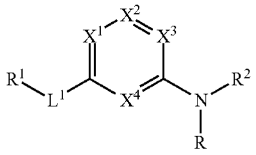

I-b

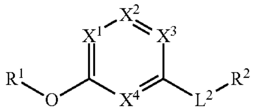

I-c

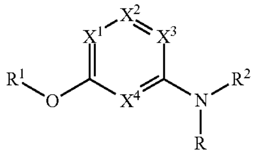

or a pharmaceutically acceptable salt thereof.

Embodiment 63. The compound according to embodiment 1, wherein the compound is:

I-d

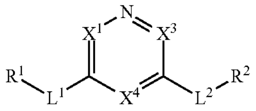

or a pharmaceutically acceptable salt thereof.

Embodiment 64. The compound according to embodiment 62 or embodiment 63, wherein the compound is selected from:

I-a-i

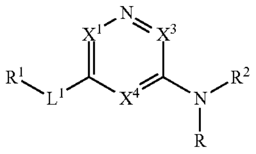

I-b-i

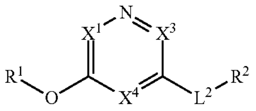

I-c-i

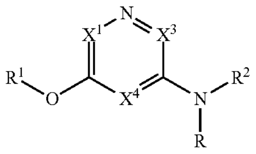

or a pharmaceutically acceptable salt thereof.

Embodiment 65. The compound according to embodiment 64, wherein the compound is selected from:

I-a-ii

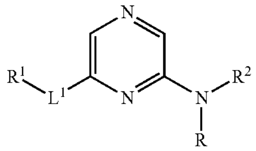

I-b-ii

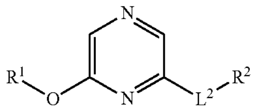

I-c-ii

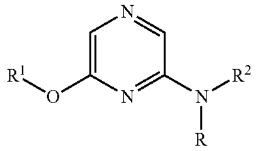

or a pharmaceutically acceptable salt thereof.

Embodiment 66. The compound according to embodiment 62, wherein the compound is selected from:

I-a-iii

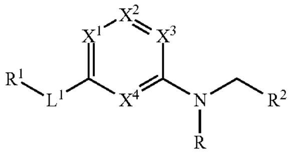

I-a-iv

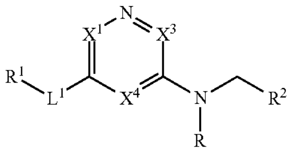

I-a-v

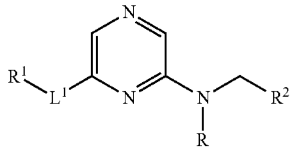

I-b-iii

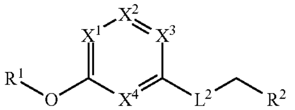

I-b-iv

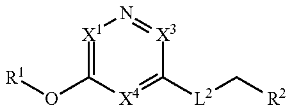

I-b-v

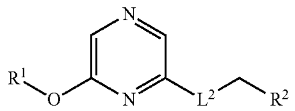

I-c-iii

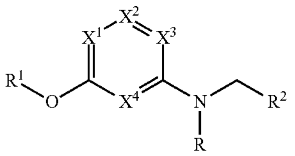

-continued

I-c-iv

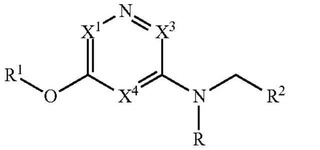

I-c-v

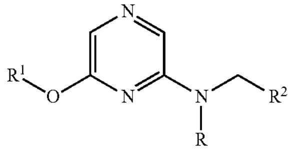

or a pharmaceutically acceptable salt thereof.

Compositions

In some embodiments, a compound of Formula I may be provided in a composition, e.g., in combination (e.g., admixture) with one or more other components.

In some embodiments, the present disclosure provides compositions that comprise and/or deliver a compound of Formula I, or an active metabolite thereof, e.g., when contacted with or otherwise administered to a system or environment e.g., which system or environment may include SARM1 NADase activity; in some embodiments, administration of such a composition to the system or environment achieves inhibition of SARM1 activity as described herein.

In some embodiments, a provided composition as described herein may be a pharmaceutical composition in that it comprises an active agent and one or more pharmaceutically acceptable excipients; in some such embodiments, a provided pharmaceutical composition comprises and/or delivers a compound of Formula I, or an active metabolite thereof to a relevant system or environment (e.g., to a subject in need thereof) as described herein.

In some embodiments, one or more compounds of Formula I is provided and/or utilized in a pharmaceutically acceptable salt form.

Among other things, the present disclosure provides compositions comprising a compound of Formula I, or a pharmaceutically acceptable salt or derivative thereof, and a pharmaceutically acceptable carrier, adjuvant, or vehicle. The amount of compound in provided compositions is such that is effective to measurably inhibit axonal degeneration in a biological sample or in a patient. In certain embodiments, a provided compound or composition is formulated for administration to a patient in need of such composition. The compounds and compositions, according to the methods of the present disclosure, may be administered using any amount and any route of administration effective for treating or lessening the severity of any disease or disorder described herein. Provided compounds are preferably formulated in dosage unit form for ease of administration and uniformity of dosage. The expression "dosage unit form" as used herein refers to a physically discrete unit of agent appropriate for the patient to be treated. It will be understood, however, that the total daily usage of the provided compounds and compositions will be decided by the attending physician within the scope of sound medical judgment. The specific effective dose level for any particular patient or organism will vary from subject to subject, depending on a variety of factors, including the disorder being treated and the severity of the disorder; the activity of the specific compound employed; the specific composition employed and its route of administration; the species, age, body weight, sex and diet of the patient; the general condition of the subject; the time of administration; the rate of excretion of the specific compound employed; the duration of the treatment; drugs used in combination or coincidental with the specific compound employed, and the like.

Provided compositions may be administered orally, parenterally, by inhalation or nasal spray, topically (e.g., as by powders, ointments, or drops), rectally, buccally, intravaginally, intraperitoneally, intracisternally or via an implanted reservoir, depending on the severity of the condition being treated. Preferably, the compositions are administered orally, intraperitoneally or intravenously. In certain embodiments, provided compounds are administered orally or parenterally at dosage levels of about 0.01 mg/kg to about 50 mg/kg, of subject body weight per day, one or more times a day, to obtain the desired therapeutic effect.

The term "parenteral" as used herein includes subcutaneous, intravenous, intramuscular, intra-articular, intra-synovial, intrasternal, intrathecal, intrahepatic, intralesional and intracranial injection or infusion techniques. Sterile injectable forms of provided compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Pharmaceutically acceptable compositions described herein may be orally administered in any orally acceptable dosage form including, but not limited to, capsules, tablets, aqueous suspensions or solutions. In such solid dosage forms the active compound may be admixed with at least one inert diluent such as sucrose, lactose or starch. Such dosage forms may also comprise, as is normal practice, additional substances other than inert diluents, e.g., lubricants and other tableting aids such a magnesium stearate and microcrystalline cellulose. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents. The active compounds can also be in micro-encapsulated form with one or more excipients as noted above.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings (i.e. buffering agents) and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions described herein may be administered in the form of suppositories for rectal or vaginal administration. These can be prepared by mixing the compounds of the present disclosure with suitable non-irritating excipients or carriers that are solid at room temperature but liquid at body (e.g. rectal or vaginal) temperature and therefore will melt in the rectum or vaginal cavity to release the active compound. Such materials include cocoa butter, a suppository wax (e.g., beeswax) and polyethylene glycols.

Pharmaceutically acceptable compositions described herein may also be administered topically, especially when the target of treatment includes areas or organs readily accessible by topical application, including diseases of the eye, the skin, or the lower intestinal tract. Topical application for the lower intestinal tract can be effected in a rectal suppository formulation (see above) or in a suitable enema formulation.

Dosage forms for topical or transdermal administration of a provided compound include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration.

Identification and/or Characterization of Compounds and/or Compositions

Among other things, the present disclosure provides various technologies for identification and/or characterization of compounds and/or compositions as described herein. For example, the present disclosure provides various assays for assessing SARM1 inhibitory activity, and specifically for assessing SARM1 inhibitory activity.

In some embodiments, performance of one or more compounds or compositions of interest in an assay as described herein is compared with that of an appropriate reference. For example, in some embodiments, a reference may be absence of the relevant compound or composition. Alternatively or additionally, in some embodiments, a reference may be presence of an alternative compound or composition, e.g., which alternative compound or composition has known performance (e.g., as a positive control or a negative control, as is understood in the art) in the relevant assay. In some embodiments, a reference may be an alternative but comparable set of conditions (e.g., temperature, pH, salt concentration, etc.). In some embodiments, a reference may be performance of the compound or composition with respect to a SARM1 variant.

Still further alternatively or additionally, in some embodiments, performance of one or more compounds or compositions of interest in an assay as described herein may be assessed in the presence of an appropriate reference compound or composition, for example, so that ability of the compound or composition to compete with the reference is determined.

In some embodiments, a plurality of compounds or compositions of interest may be subjected to analysis in a particular assay and/or compared with the same reference. In some embodiments, such a plurality of compounds or compositions may be or include a set of compounds or compositions that is considered to be a "library" because multiple members share one or more features (e.g., structural elements, source identity, synthetic similarities, etc.).

Certain exemplary assays that may be useful in the practice of the present disclosure are exemplified in the Examples below. Those skilled in the art, reading the present disclosure, will be aware that useful or relevant systems for identifying and/or characterizing compounds and/or compositions in accordance with the present disclosure are not limited to those included in the Examples, or otherwise discussed below.

In some embodiments, compounds and/or compositions may be identified based on and/or characterized by one or more activities or characteristics such as, for example: promoting axonal integrity, cytoskeletal stability, and/or neuronal survival. In some embodiments, provided SARM1 inhibitors inhibit catabolism of NAD+ to by SARM1. In some embodiments, provided SARM1 inhibitors slow the rate of NAD+ catabolism.

In some embodiments, provided SARM1 inhibitors reduce or inhibit binding of NAD+ by SARM1. In some embodiments, provided SARM1 inhibitors bind to SARM1 within a pocket comprising one or more catalytic residues (e.g., a catalytic cleft of SARM1). Examples of such catalytic residues include the glutamic acid at position 642 (E642).

In some embodiments, provided SARM1 inhibitors disrupt and/or prevent multimerization of the TIR1 domain of SARM1. In some embodiments, provided SARM1 inhibitors disrupt the multimerization of the SAM domains. In some embodiments, provided SARM1 inhibitors disrupt the axonal signaling cascade that leads to depletion of NAD+.

In some embodiments, the present disclosure provides assays useful for identifying and/or characterizing one or more activities and/or characteristics of compound and/or compositions of interest. For example, in some embodiments, the present disclosure provides in vitro, cellular, and/or in vivo systems for assessing one or more such activities and/or characteristics.

SARM1 Activity Assays

In some embodiments, a method of identifying a SARM1 inhibitor comprises: a) providing a mixture comprising i) a mutant or fragment of SARM1, ii) NAD+ and iii) a candidate inhibitor, wherein the mutant or fragment has constitutive activity; b) incubating the mixture; c) quantifying NAD+ in the mixture after the incubating; and d) identifying the candidate inhibitor compound as an inhibitor if the amount of NAD+ is greater than that of a control mixture that does not contain the candidate inhibitor.

In some embodiments, provided are methods of identifying a SARM1 inhibitor, comprising: a) providing a mixture comprising i) a full-length SARM1, ii) NAD+ and iii) a candidate inhibitor, wherein the full-length SARM1 has constitutive activity; b) incubating the mixture; c) quantifying NAD+ and ADPR (or cADPR) in the mixture after the incubating; d) determining the molar ratio of NAD+:ADPR (or cADPR); and e) identifying the candidate inhibitor compound as an inhibitor if the molar ratio is greater than that of a control mixture that does not contain the candidate inhibitor.

In some embodiments, provided are methods of identifying a SARM1 inhibitor, comprising: a) providing a mixture comprising a solid support to which is bound i) a full-length SARM1 and at least one tag, ii) NAD+, and iii) a candidate inhibitor; b) incubating the mixture; c) quantifying the NAD+ after the incubating; and d) identifying the candidate inhibitor compound as a SARM1 inhibitor if the concentration of NAD+ is greater than that of a control.

SARM1 Binding Assays

In some embodiments, the efficacy of provided SARM1 inhibitors can be determined according to, e.g., the assays described in WO 2018/057989, published on Mar. 29, 2018, which is hereby incorporated by reference in its entirety. In some embodiments, the provided SARM1 inhibitors can be applied to a solution containing SARM1 or a fragment thereof. In some embodiments, the provided SARM1 inhibitors can be applied to an in vitro system. In some embodiments, the provided SARM1 inhibitors can be applied to an in vivo. In some embodiments, the provided SARM1 inhibitors can be applied to a patient. In some embodiments, a SARM1 inhibitor can be mixed with SARM1 or fragment thereof that has been labeled with an epitope tag. In some embodiments, the amount of bound SARM1 inhibitor can be compared to the amount of unbound SARM1 inhibitor, yielding the affinity for the SARM1 inhibitor.

In some embodiments, the mutant or fragment of SARM1 is a SAM-TIR fragment having constitutive activity. Fragments of SARM1 having constitutive activity include, for example and without limitation, a SARM1 with the autoinhibitory domain deleted; at least one point mutation of SARM1 that renders the autoinhibitory domain inactive; a fragment of SARM1 containing a TIR domain; or a fragment of SARM1 consisting of SAM and TIR domains. In some embodiments a SARM1 polypeptide can include one or more additional amino acid sequences that can act as tags, such as a His tag, a streptavidin tag, or a combination thereof. In some embodiments a SARM1 polypeptide can include a tag at the amino terminus, at the carboxy terminus, or a combination thereof. In some embodiments, SARM1 or fragment thereof labeled with an epitope tag can be used to measure the binding efficacy of provided SARM1 inhibitors.

Purification of SARM1-TIR domains

In some embodiments, a SARM1-TIR domain can be engineered with various protein, or epitope, tags that can be useful, for example, in purification. In some embodiments, the present disclosure also provides for a NRK1-HEK293T cell line comprising HEK293T cells transformed with a Nicotinamide Riboside Kinase 1 (NRK1). In some embodiments, HEK293T cells transformed or transfected with a DNA sequence encoding Nicotinamide Riboside Kinase 1 (NRK1). In some embodiments, the DNA encoding NRK1 can be genomic or cDNA. In some embodiments, HEK293T cells are stably or transiently transfected with DNA encoding NRK1 from a source exogenous to the host cell. In some embodiments, HEK293T cells are stably or transiently transfected with DNA encoding NRK1 such that the cells express NRK1 at an elevated level compared to control cells. In some embodiments, DNA encoding NRK1 is under the control of one or more exogenous regulatory DNA sequences such as a promoter, an enhancer or a combination thereof. In some embodiments, a combination of a DNA sequences encoding NRK1 and regulatory sequences is a non-naturally occurring combination. In some embodiments, DNA encoding NRK1, either genomic or cDNA, comprises an expression vector such as an FCIV expression vector. In some embodiments, DNA encoding NRK1 is derived from genomic DNA or cDNA from a vertebrate or invertebrate species such as, but not limited to, human, mouse, zebrafish or a *Drosophila*. In some configurations, the NRK1 DNA is a human NRK1 DNA.

Applications and Uses

The present disclosure provides a variety of uses and applications for compounds and/or compositions as described herein, for example in light of their activities and/or characteristics as described herein. In some embodiments, such uses may include therapeutic and/or diagnostic uses. Alternatively, in some embodiments such uses may include research, production, and/or other technological uses.

In one aspect, the present disclosure provides methods comprising administering one or more compounds of Formula I to a subject, e.g., to treat, prevent, or reduce the risk of developing one or more conditions characterized by axonal degeneration. In some such embodiments, the compound of Formula I is a SARM1 inhibitor.

Another embodiment of the present disclosure relates to a method of inhibiting SARM1 activity in a patient comprising steps of administering to said patient a provided compound, or a composition comprising said compound.

Inhibition of enzymes in a biological sample is useful for a variety of purposes that are known to one of skill in the art. Examples of such purposes include, but are not limited to biological assays, gene expression studies, and biological target identification.

In certain embodiments, the present disclosure relates to a method of treating axonal degeneration in a biological sample comprising the step of contacting said biological sample with a compound or composition of Formula I. In some embodiments, one or more compounds and/or compositions as described herein are useful, for example as a method of for inhibiting the degradation of neurons derived from a subject. In some embodiments, one or more compounds and/or compositions as described herein, are useful for inhibiting the degeneration of a neuron, or portion thereof, cultured in vitro. In some embodiments, one or more compounds and/or compositions as described herein, are useful as stabilizing agents to promote in vitro neuronal survival.

In some embodiments, provided compounds and/or compositions inhibit NADase activity of SARM1. Alternatively or additionally, in some embodiments, provided compounds alleviate one or more attributes of neurodegeneration. In some embodiments, the present disclosure provides methods of treating a neurodegenerative disease or disorder associated with axonal degeneration.

In some embodiments, one or more compounds and/or compositions as described herein are useful, for example, in the practice of medicine. In some embodiments, one or more compounds and/or compositions as described herein are useful, for example, to treat, prevent, or ameliorate axonal degeneration (e.g., one or more features or characteristics thereof). In some embodiments, one or more compounds and/or compositions as described herein are useful, for example to inhibit axonal degeneration, including axonal degeneration that results from reduction or depletion of NAD+. In some embodiments, one or more compounds and/or compositions as described herein are useful, for example to prevent the axon distal to an axonal injury from degenerating.

In some embodiments, one or more compounds and/or compositions as described herein are useful, for example as a method for inhibiting the degradation of a peripheral nervous system neuron or a portion thereof. In some embodiments, one or more compounds and/or compositions as described herein are useful, for example as a method for inhibiting or preventing degeneration of a central nervous system (neuron) or a portion thereof. In some embodiments, one or more compounds or compositions as described herein is characterized that, when administered to a population of subjects, reduces one or more symptoms or features of neurodegeneration. For example, in some embodiments, a relevant symptom or feature may be selected from the group consisting of extent, rate, and/or timing of neuronal disruption.

In certain embodiments, the present disclosure provides compounds that are useful, for example, as analytical tools, as probes in biological assays, or as therapeutic agents in accordance with the present disclosure. Compounds provided by this disclosure are also useful for the study of SARM1 activity in biological and pathological phenomena and the comparative evaluation of new SARM1 activity inhibitors in vitro or in vivo. In certain embodiments, the present disclosure provides assays for identifying and/or characterizing compounds and/or compositions provided herein. In some embodiments, provided assays utilize particular reagents and/or systems (e.g., certain vector constructs and/or polypeptides) useful in assaying SARM1 activity. For example, in some embodiments, provided assays may utilize, for example, a SAM-TIR in which the SARM1 N-terminal auto-inhibitory domain is deleted, and/or one or more tagged versions of a TIR domain.

In some embodiments, one or more compounds and/or compositions as described herein are useful, for example as a method of for inhibiting the degradation of neurons derived from a subject. In some embodiments, one or more compounds and/or compositions as described herein, are useful for inhibiting the degeneration of a neuron, or portion thereof, cultured in vitro. In some embodiments, one or more compounds and/or compositions as described herein, are useful as stabilizing agents to promote in vitro neuronal survival.

In some embodiments, one or more compounds and/or compositions as described herein are useful, for example in affecting biomarkers associated with neurodegeneration. In some embodiments, changes in biomarkers can be detected systemically or with a sample of cerebral spinal fluid (CSF), plasma, serum, and/or tissue from a subject. In some embodiments, one or more compounds and/or compositions can be used to affect a change in the concentration of neurofilament protein light (NF-L) and/or neurofilament protein heavy (NF—H) contained the cerebral spinal fluid of a subject. In some embodiments, one or more compounds and/or compositions as described herein can affect constitutive NAD and/or cADPR levels in neurons and/or axons.

In some embodiments, one or more compounds and/or compositions as described herein can affect a detectable change in the levels of one or more neurodegeneration-associated proteins in a subject. Such proteins include, but are not limited to, albumin, amyloid-β (Aβ)38, A040, A042, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, one or more compounds and/or compositions as described herein can affect a change in cytokines and/or chemokines, including, but not limited to, Ccl2, Ccl7, Ccl12, Csf1, and/or Il6.

Diseases, Disorders, and Conditions

In some embodiments, compounds and/or compositions as described herein may be administered to subjects suffering from one or more diseases, disorders, or conditions.

In some embodiments, the condition is an acute condition. In some embodiments, the condition is a chronic condition.

In some embodiments, the condition is characterized by axonal degeneration in the central nervous system, the peripheral nervous system, the optic nerve, the cranial nerves, or a combination thereof.

In some embodiments, the condition is or comprises acute injury to the central nervous system, e.g., injury to the spinal cord and/or traumatic brain injury. In some embodiments, the condition is or comprises a chronic injury to the central nervous system, e.g., injury to the spinal cord, traumatic brain injury, and/or traumatic axonal injury. In some embodiments, the condition is or comprises chronic traumatic encephalopathy (CTE).

In some embodiments, the condition is a chronic condition affecting the central nervous system, e.g., Parkinson's disease, amyotrophic lateral sclerosis, multiple sclerosis, or Huntington disease, Alzheimer's disease.

In some embodiments, the condition is an acute peripheral neuropathy. Chemotherapy-induced peripheral neuropathy (CIPN) is an example of an acute peripheral neuropathy. CIPN can be associated with various drugs, such as, but not limited to, thalidomide, epothilones (e.g., ixabepilone), taxanes (e.g., paclitaxel and docetaxel), *vinca* alkaloids (e.g., vinblastine, vinorelbine, vincristine, and vindesine), proteasome inhibitors (e.g., bortezomib), platinum-based drugs (e.g., cisplatin, oxaliplatin, and carboplatin).

In some embodiments, the condition is a chronic condition affecting the peripheral nervous system, e.g., diabetic neuropathy, HIV neuropathy, Charcot Marie Tooth disease, or amyotrophic lateral sclerosis.

In some embodiments, the condition is an acute condition affecting the optic nerve, e.g., acute optic neuropathy (AON) or acute angle closure glaucoma.

In some embodiments, the condition is a chronic condition affecting the optic nerve, e.g., Leber's congenital amaurosis, Leber's hereditary optic neuropathy, primary open angle glaucoma, and autosomal dominant optic atrophy.

In some embodiments, one or more compounds and/or compositions as described herein are useful, for example, to treat one or more neurodegenerative diseases, disorders or conditions selected from the group consisting of neuropathies or axonopathies. In some embodiments, one or more compounds and/or compositions as described herein are useful, for example to treat a neuropathy or axonopathy associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration is selected from a list contained herein. In some embodiments, a neuropathy or axonopathy is associated with axonal degeneration, including, but not limited to Parkinson's disease, non-Parkinson's disease, Alzheimer's disease, Herpes infection, diabetes, amyotrophic lateral sclerosis, a demyelinating disease, ischemia or stroke, chemical injury, thermal injury, and AIDS.

In some embodiments, one or more compounds or compositions as described herein is characterized that, when administered to a population of subjects, reduces one or more symptoms or features of neurodegeneration. For example, in some embodiments, a relevant symptom or feature may be selected from the group consisting of extent, rate, and/or timing of neuronal disruption. In some embodiments, neuronal disruption may be or comprise axonal degradation, loss of synapses, loss of dendrites, loss of synaptic density, loss of dendritic arborization, loss of axonal branching, loss of neuronal density, loss of myelination, loss of neuronal cell bodies, loss of synaptic potentiation, loss of action-potential potentiation, loss of cytoskeletal stability, loss of axonal transport, loss of ion channel synthesis and turnover, loss of neurotransmitter synthesis, loss of neurotransmitter release and reuptake capabilities, loss of axon-potential propagation, neuronal hyperexcitability, and/or neuronal hypoexcitability. In some embodiments, neuronal disruption is characterized by an inability to maintain an appropriate resting neuronal membrane potential. In some embodiments, neuronal disruption is characterized by the appearance of inclusion bodies, plaques, and/or neurofibrillary tangles. In some embodiments, neuronal disruption is characterized by the appearance of stress granules. In some embodiments, neuronal disruption is characterized by the intracellular activation of one or more members of the cysteine-aspartic protease (Caspase) family. In some embodiments, neuronal disruption is characterized by a neuron undergoing programed cell death (e.g. apoptosis, pyroptosis, ferroapoptosis, and/or necrosis) and/or inflammation.

In some embodiments, the neurodegenerative or neurological disease or disorder is associated with axonal degeneration, axonal damage, axonopathy, a demyelinating disease, a central pontine myelinolysis, a nerve injury disease or disorder, a metabolic disease, a mitochondrial disease, metabolic axonal degeneration, axonal damage resulting from a leukoencephalopathy or a leukodystrophy. In some embodiments, the neurodegenerative or neurological disease or disorder is selected from the group consisting of spinal cord injury, stroke, multiple sclerosis, progressive multifocal leukoencephalopathy, congenital hypomyelination, encephalomyelitis, acute disseminated encephalomyelitis, central pontine myelolysis, osmotic hyponatremia, hypoxic demyelination, ischemic demyelination, adrenoleukodystrophy, Alexander's disease, Niemann-Pick disease, Pelizaeus Merzbacher disease, periventricular leukomalacia, globoid cell leukodystrophy (Krabbe's disease), Wallerian degeneration, optic neuritis, transverse myelitis, amyotrophic lateral sclerosis (ALS, Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy (chemotherapy induced neuropathy; CIPN), neuropathy, acute ischemic optic neuropathy, vitamin $B_{12}$ deficiency, isolated vitamin E deficiency syndrome, Bassen-Kornzweig syndrome, Glaucoma, Leber's hereditary optic atrophy (neuropathy), Leber congenital amaurosis, neuromyelitis optica, metachromatic leukodystrophy, acute hemorrhagic leukoencephalitis, trigeminal neuralgia, Bell's palsy, cerebral ischemia, multiple system atrophy, traumatic glaucoma, tropical spastic paraparesis human T-lymphotropic virus 1 (HTLV-1) associated myelopathy, west Nile virus encephalopathy, La Crosse virus encephalitis, Bunyavirus encephalitis, pediatric viral encephalitis, essential tremor, Charcot-Marie-Tooth disease, motor neuron disease, spinal muscular atrophy (SMA), hereditary sensory and autonomic neuropathy (HSAN), adrenomyeloneuropathy, progressive supra nuclear palsy (PSP), Friedrich's ataxia, hereditary ataxias, noise induced hearing loss, congenital hearing loss, Lewy Body Dementia, frontotemporal dementia, amyloidosis, diabetic neuropathy, HIV neuropathy, enteric neuropathies and axonopathies, Guillain-Barre syndrome, severe acute motor axonal neuropathy (AMAN), Creutzfeldt-Jakob disease, transmissible spongiform encephalopathy, spinocerebellar ataxias, pre-eclampsia, hereditary spastic paraplegias, spastic paraparesis, familial spastic paraplegia, French settlement disease, Strumpell-Lorrain disease, and non-alcoholic steatohepatitis (NASH).

In some embodiments, the present disclosure provides inhibitors of SARM1 activity for treatment of neurodegenerative or neurological diseases or disorders that involve axon degeneration or axonopathy. The present disclosure also provides methods of using inhibitors of SARM1 activity to treat, prevent or ameliorate axonal degeneration, axonopathies and neurodegenerative or neurological diseases or disorders that involve axonal degeneration.

In some embodiments, the present disclosure provides methods of treating neurodegenerative or neurological diseases or disorders related to axonal degeneration, axonal damage, axonopathies, demyelinating diseases, central pontine myelinolysis, nerve injury diseases or disorders, metabolic diseases, mitochondrial diseases, metabolic axonal degeneration, axonal damage resulting from a leukoencephalopathy or a leukodystrophy.

In some embodiments, neuropathies and axonopathies include any disease or condition involving neurons and/or supporting cells, such as for example, glia, muscle cells or fibroblasts, and, in particular, those diseases or conditions involving axonal damage. Axonal damage can be caused by traumatic injury or by non-mechanical injury due to diseases, conditions, or exposure to toxic molecules or drugs. The result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

In some embodiments, a peripheral neuropathy can involve damage to the peripheral nerves, and/or can be caused by diseases of the nerves or as the result of systemic illnesses. Some such diseases can include diabetes, uremia, infectious diseases such as AIDs or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis nodosa. In some embodiments, peripheral nerve degeneration results from traumatic (mechanical) damage to nerves as well as chemical or thermal damage to nerves. Such conditions that injure peripheral nerves include compression or entrapment injuries such as glaucoma, carpal tunnel syndrome, direct trauma, penetrating injuries, contusions, fracture or dislocated bones; pressure involving superficial nerves (ulna, radial, or peroneal) which can result from prolonged use of crutches or staying in one position for too long, or from a tumor; intraneural hemorrhage; ischemia; exposure to cold or radiation or certain medicines or toxic substances such as herbicides or pesticides. In particular, the nerve damage can result from chemical injury due to a cytotoxic anticancer agent such as, for example, taxol, cisplatinin, a proteasome inhibitor, or a *vinca* alkaloid such as vincristine. Typical symptoms of such peripheral neuropathies include weakness, numbness, paresthesia (abnormal sensations such as burning, tickling, pricking or tingling) and pain in the arms, hands, legs and/or feet. In some embodiments, a neuropathy is associated with mitochondrial dysfunction. Such neuropathies can exhibit decreased energy levels, i.e., decreased levels of NAD and ATP.

In some embodiments, peripheral neuropathy is a metabolic and endocrine neuropathy which includes a wide spectrum of peripheral nerve disorders associated with systemic diseases of metabolic origin. These diseases include, for example, diabetes mellitus, hypoglycemia, uremia, hypothyroidism, hepatic failure, polycythemia, amyloidosis, acromegaly, *porphyria*, disorders of lipid/glycolipid metabolism, nutritional/vitamin deficiencies, and mitochondrial disorders, among others. The common hallmark of these diseases is involvement of peripheral nerves by alteration of the structure or function of myelin and axons due to metabolic pathway dysregulation.

In some embodiments, neuropathies include optic neuropathies such as glaucoma; retinal ganglion degeneration such as those associated with retinitis pigmentosa and outer retinal neuropathies; optic nerve neuritis and/or degeneration including that associated with multiple sclerosis; traumatic injury to the optic nerve which can include, for example, injury during tumor removal; hereditary optic neuropathies such as Kjer's disease and Leber's hereditary optic neuropathy; ischemic optic neuropathies, such as those secondary to giant cell arteritis; metabolic optic neuropathies such as neurodegenerative diseases including Leber's neuropathy mentioned earlier, nutritional deficiencies such as deficiencies in vitamins B12 or folic acid, and toxicities such as due to ethambutol or cyanide; neuropathies caused by adverse drug reactions and neuropathies caused by vitamin deficiency. Ischemic optic neuropathies also include non-arteritic anterior ischemic optic neuropathy.

In some embodiments neurodegenerative diseases that are associated with neuropathy or axonopathy in the central nervous system include a variety of diseases. Such diseases include those involving progressive dementia such as, for example, Alzheimer's disease, senile dementia, Pick's disease, and Huntington's disease; central nervous system diseases affecting muscle function such as, for example, Parkinson's disease, motor neuron diseases and progressive ataxias such as amyotrophic lateral sclerosis; demyelinating diseases such as, for example multiple sclerosis; viral encephalitides such as, for example, those caused by enteroviruses, arboviruses, and herpes simplex virus; and prion diseases. Mechanical injuries such as glaucoma or traumatic injuries to the head and spine can also cause nerve injury and degeneration in the brain and spinal cord. In addition, ischemia and stroke as well as conditions such as nutritional deficiency and chemical toxicity such as with chemotherapeutic agents can cause central nervous system neuropathies.

In some embodiments, the present disclosure provides a method of treating a neuropathy or axonopathy associated with axonal degeneration. In some such embodiments, a neuropathy or axonopathy associated with axonal degeneration can be any of a number of neuropathies or axonopathies such as, for example, those that are hereditary or congenital or associated with Parkinson's disease, Alzheimer's disease, Herpes infection, diabetes, amyotrophic lateral sclerosis, a demyelinating disease, ischemia or stroke, chemical injury, thermal injury, and AIDS. In addition, neurodegenerative diseases not mentioned above as well as a subset of the above mentioned diseases can also be treated with the methods of the present disclosure. Such subsets of diseases can include Parkinson's disease or non-Parkinson's diseases, or Alzheimer's disease.

Subjects

In some embodiments, compounds and/or compositions as described herein are administered to subjects suffering from or susceptible to a disease, disorder or condition as described herein; in some embodiments, such a disease, disorder or condition is characterized by axonal degeneration, such as one of the conditions mentioned herein.

In some embodiments, a subject to whom a compound or composition is administered as described herein exhibits one or more signs or symptoms associated with axonal degeneration; in some embodiments, the subject does not exhibit any signs or symptoms of neurodegeneration.

In some embodiments, provided methods comprise administering a compound of Formula I to a patient in need thereof. In some such embodiments, the patient is at risk of developing a condition characterized by axonal degeneration. In some embodiments, the patient has a condition characterized by axonal degeneration. In some embodiments, the patient has been diagnosed with a condition characterized by axonal degeneration.

In some embodiments, provided methods comprise administering a composition as described herein to a patient population of in need thereof. In some embodiments, the population is drawn from individuals who engage in activities where the potential for traumatic neuronal injury is high. In some embodiments, the population is drawn from athletes who engage in contact sports or other high-risk activities.

In some embodiments, the subject is at risk of developing a condition characterized by axonal degeneration. In some embodiments, the subject is identified as being at risk of axonal degeneration, e.g., based on the subject's genotype, a diagnosis of a condition associated with axonal degeneration, and/or exposure to an agent and/or a condition that induces axonal degeneration.

In some embodiments, the patient is at risk of developing a neurodegenerative disorder. In some embodiments the patient is elderly. In some embodiments, the patient is known to have a genetic risk factor for neurodegeneration. In some embodiments, the patient has a family history of neurodegenerative disease. In some embodiments, the patient expresses one or more copies of a known genetic risk factor for neurodegeneration. In some embodiments, the patient is drawn from a population with a high incidence of neurodegeneration. In some embodiments, the patient has a hexanucleotide repeat expansion in chromosome 9 open reading frame 72. In some embodiments, the patient has one or more copies of the ApoE4 allele.

In some embodiments, subjects to which a compound or composition as described herein is administered may be or comprise subjects suffering from or susceptible to a neurodegenerative disease, disorder or condition. In some embodiments, a neurodegenerative disease, disorder or condition may be or comprise a traumatic neuronal injury. In some embodiments, a traumatic neuronal injury is blunt force trauma, a closed-head injury, an open head injury, exposure to a concussive and/or explosive force, a penetrating injury in to the brain cavity or innervated region of the body. In some embodiments, a traumatic neuronal injury is a force which causes the axons to deform, stretch, crush or sheer.

In some embodiments, the subject engages in an activity identified as a risk factor for neuronal degradation, e.g., a subject that engages in contact sports or occupations with a high chance for traumatic neuronal injury.

For example, the subject may be a patient who is receiving, or is prescribed, a chemotherapy associated with peripheral neuropathy. Examples of chemotherapeutic agents include, but not limited to, thalidomide, epothilones (e.g., ixabepilone), taxanes (e.g., paclitaxel and docetaxel), *vinca* alkaloids (e.g., vinblastine, vinorelbine, vincristine, and vindesine), proteasome inhibitors (e.g., bortezomib), platinum-based drugs (e.g., cisplatin, oxaliplatin, and carboplatin).

In some embodiments, provided methods comprise administering a composition as described herein to a patient or patient population based on the presence or absence of one or more biomarkers. In some embodiments, provided methods further comprise monitoring the level of a biomarker in a patient or patient population and adjusting the dosing regimen accordingly.

Dosing

Those of skill in the art will appreciate that, in some embodiments, the exact amount of a particular compound included in and/or delivered by administration of a pharmaceutical composition or regimen as described herein may be selected by a medical practitioner and may be different for different subjects, for example, upon consideration of one or more of species, age, and general condition of the subject, and/or identity of the particular compound or composition, its mode of administration, and the like. Alternatively, in some embodiments, the amount of a particular compound included in and/or delivered by administration of a pharmaceutical composition or regimen as described herein may be standardized across a relevant patient population (e.g., all patients, all patients of a particular age or stage of disease or expressing a particular biomarker, etc.).

A provided compound or composition of the present disclosure is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided compound or composition of the present disclosure will be decided by the attending physician within the scope of sound medical judgment. The specific effective dose level for any particular patient or organism will depend upon a variety of factors including the disorder being treated and the severity of the disorder; the clinical condition of the individual patient; the cause of the disorder; the activity of the specific compound employed; the specific composition employed; the age, body weight, general health, sex and diet of the patient; the time of administration, delivery site of the agent, route of administration, and rate of excretion of the specific compound employed; the duration of the treatment; drugs used in combination or coincidental with the specific compound employed, and like factors well known in the medical arts. The effective amount of the compound to be administered will be governed by such considerations, and is the minimum amount necessary to inhibit SARM1 activity as required to prevent or treat the undesired disease or disorder, such as for example, neurodegeneration or traumatic neural injury.

A pharmaceutically acceptable composition of this disclosure can be administered to humans and other animals orally, rectally, intravenously, parenterally, intracisternally, intravaginally, intraperitoneally, topically (as by powders, ointments, or drops), bucally, as an oral or nasal spray, or the like, depending on the severity of the disease, disorder or infection being treated. The daily dose is, in certain embodiments, given as a single daily dose or in divided doses two to six times a day, or in sustained release form. This dosage regimen may be adjusted to provide the optimal therapeutic response. The compounds may be administered on a regimen of 1 to 4 times per day, preferably once or twice per day.

In some embodiments, compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intradermal, intraocular, intralesional and intracranial injection or infusion techniques. Preferably, the compositions are administered orally, intraperitoneally or intravenously.

In some embodiments, pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

Those additional agents may be administered separately from a provided compound or composition thereof, as part of a multiple dosage regimen. Alternatively, those agents may be part of a single dosage form, mixed together with a provided compound in a single composition. If administered as part of a multiple dosage regime, the two active agents may be submitted simultaneously, sequentially or within a period of time from one another, normally within five hours from one another.

It should also be understood that a specific dosage and treatment regimen for any particular patient may depend upon a variety of factors, including the activity of the specific compound employed, the age, body weight, general health, sex, diet, time of administration, rate of excretion, drug combination, and the judgment of the treating physician and the severity of the particular disease being treated. In some embodiments, the amount of a compound of the present disclosure in the composition will also depend upon the particular compound in the composition.

In some embodiments, SARM1 inhibition as described herein may be utilized in combination with one or more other therapies to treat a relevant disease, disorder, or condition. In some embodiments, dosing of a SARM1 inhibitor is altered when utilized in combination therapy as compared with when administered as monotherapy; alternatively or additionally, in some embodiments, a therapy that is administered in combination with SARM11 inhibition as described herein is administered according to a regimen or protocol that differs from its regimen or protocol when administered alone or in combination with one or more therapies other than SARM1 inhibition. In some embodiments, compositions which comprise an additional therapeutic agent, that additional therapeutic agent and a provided compound may act synergistically. In some embodiments, one or both therapies utilized in a combination regimen is administered at a lower level or less frequently than when it is utilized as monotherapy.

In some embodiments, compounds and/or compositions described herein are administered with a chemotherapeutic agent including, but not limited to, alkylating agents, anthracyclines, taxanes, epothilones, histone deacetylase inhibitors, topoisomerase inhibitors, kinase inhibitors, nucleotide analogs, peptide antibiotics, platinum-based agents, retinoids, *vinca* alkaloids and derivatives. In some embodiments, compounds and/or compositions described herein are administered in combination with PARP inhibitors.

Exemplification

The present teachings including descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Methods

Some methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods In Molecular Biology, ed. Richard, Humana Press, N J, 1995; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Methods of administration of pharmaceuticals and dosage regimes, can be determined according to standard principles of pharmacology, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

Example 1: Synthesis of Compounds

General Synthetic Methods

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid, 0.1-0.01% TFA, 10 mM aqueous ammonium bicarbonate or 0.2% aqueous ammonium hydroxide and used one of the following columns:

a) Waters Xbridge C18 10 μm 30×100 mm column
b) Waters Sunfire C18 10 μm 30×100 mm column
c) Waters Xbridge C18 3.5 μm 50×4.6 mm column
d) HALO C18 2.7 μm 30×4.6 mm column
e) Waters Sunfire C18 3.5 μm 50×4.6 mm column

Synthetic Example A: Synthesis of Example 105

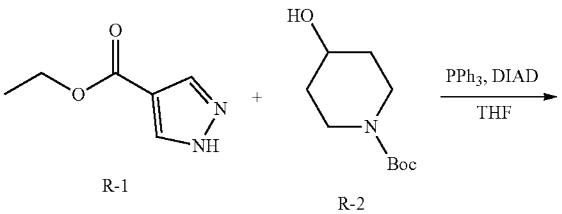

R-1

R-2

-continued

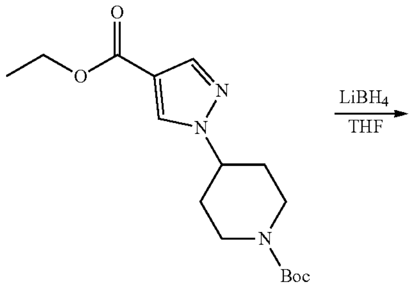

I-1

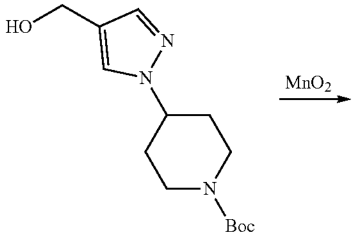

I-2

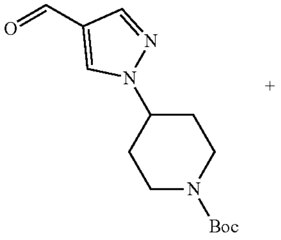

I-3

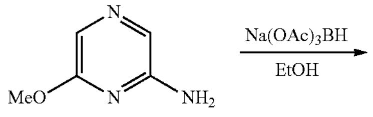

Ex 159

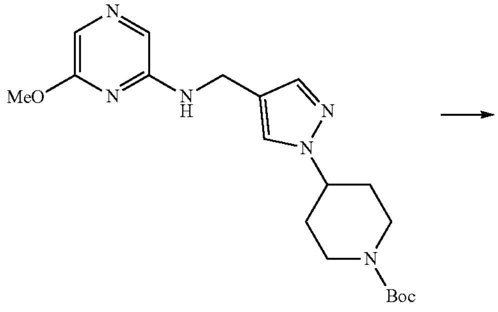

Ex 103

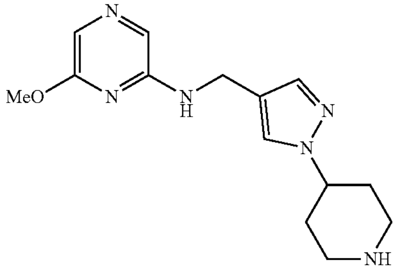

Ex 105

The solution of R-2 (6.63 g, 33 mmol) and triphenylphosphine (10.5 g, 40 mmol) in THE (150 mL) at 0° C. is added diisopropyl azodicarboxylate (8.08 g, 40 mmol) dropwise. After 5 minutes the solution of R-2 (4.2 g, 30 mmol) in THE (10 mL) is added. The reaction mixture is stirred at room temperature overnight then concentrated under reduced pressure. The residue is purified by flash chromatography ($SiO_2$, petroleum ether:acetone=2:1) to afford I-1 (7.3 g, 75%).

The solution of I-1 (8.5 g, 26.3 mmol) in anhydrous THE (80 mL) is added $LiBH_4$ (11.46 g, 526 mmol) in portions at room temperature. The mixture is stirred at 60° C. for 16 h. The reaction mixture is cooled to 0° C., and then EtOAc (100 mL) is added dropwise, followed with saturated aqueous solution of $NH_4Cl$ (100 mL) and water (50 mL) at 0° C. The mixture is extracted with EtOAc (100 mL×3). The combined organic layers are washed with brine (100 mL), dried over $Na_2SO_4$, and concentrated under reduced pressure. The residue is purified by flash chromatography ($SiO_2$, acetone:petroleum ether=1:1) to afford I-2 (3.08 g, 41.5%).

A suspension of activated Manganese (IV) oxide (8.14 g, 93.6 mmol) and I-2 (2.63 g, 9.36 mmol) in acetone (50 mL) is stirred at 60° C. for 6 h. The mixture is filtered, and the filtrate is concentrated under reduced pressure. The residue is purified by flash chromatography ($SiO_2$, petroleum ether: EtOAc=1:1) to afford I-3 (2.4 g, 92%).

A solution of I-3 (2.4 g, 8.6 mmol) and Example 159 (1.08 g, 8.6 mmol) in EtOH (40 mL) is stirred at 80° C. overnight. The mixture is cooled to room temperature and sodium triacetoxyborohydride (5.47 g, 25.8 mmol) is added in portions. The mixture is stirred at room temperature for 16 h then poured into water (80 mL) and extracted with EtOAc (50 mL×4). The combined organic layers are washed with brine, dried over $Na_2SO_4$, and concentrated under reduced pressure. The residue is purified by flash chromatography ($SiO_2$, petroleum ether:EtOAc=1:3) to afford Example 103 (1.47 g, 44%).

A solution of Example 103 (1.47 g, 3.78 mmol) in MeOH (20 mL) is added HCl/dioxane (4 M, 10 mL), and then stirred at room temperature overnight. The solvent is removed under reduced pressure. The residue is purified by prep-HPLC to afford Example 105 (837 mg, 77%).

The following examples are prepared in similar fashion from the appropriate reagents: Examples 62, 104, 106, 119-120, 141-142, 147-148, and 205.

Synthetic Example B: Synthesis of Example 20

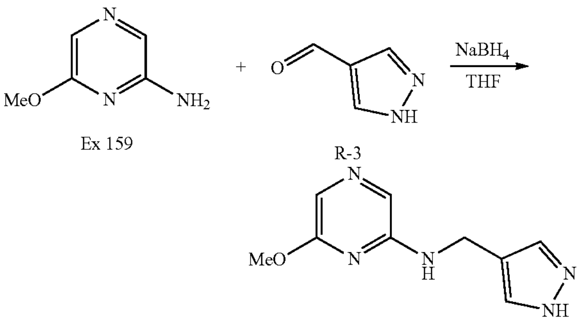

Ex 159

R-3

Ex 20

A mixture of Example 206 (7.0 g, 56 mmol) and R-3 (6.5 g, 68 mmol) in EtOH (50 mL) is stirred at 60° C. overnight.

The mixture is cooled to room temperature and $NaBH_4$ (8.6 g, 224 mmol) is added in portions. The mixture is stirred at room temperature for 2 h. The reaction mixture is poured into saturated aqueous $NH_4Cl$ solution (100 mL), and then extracted with EtOAc (300 mL×3). The combined organic layers are dried over $Na_2SO_4$, and concentrated under reduced pressure. The residue is purified by flash chromatography ($SiO_2$, petroleum ether:EtOAc=1:1) to afford the crude product that is further purified by stirring in EtOAc (50 mL) and petroleum ether (10 mL) at room temperature for 2 h, filtered, and dried to afford Example 38 (2.6 g, 21%).

The following examples are prepared in similar fashion from the appropriate aniline and aldehyde reagents: Examples 7-10, 12, 14, 18-22, 26-27, 33-34, 36-42, 44, 47-61, 64-70, 73, 75-76, 85-93, 97, 100-101, 109, 113-114, 118, 121, 123, 126-132, 143-146, 154-158, 170, 178-179, 181-185, 194, 203-204, 206, 210, and 214-216.

Synthetic Example C: Synthesis of Example 3

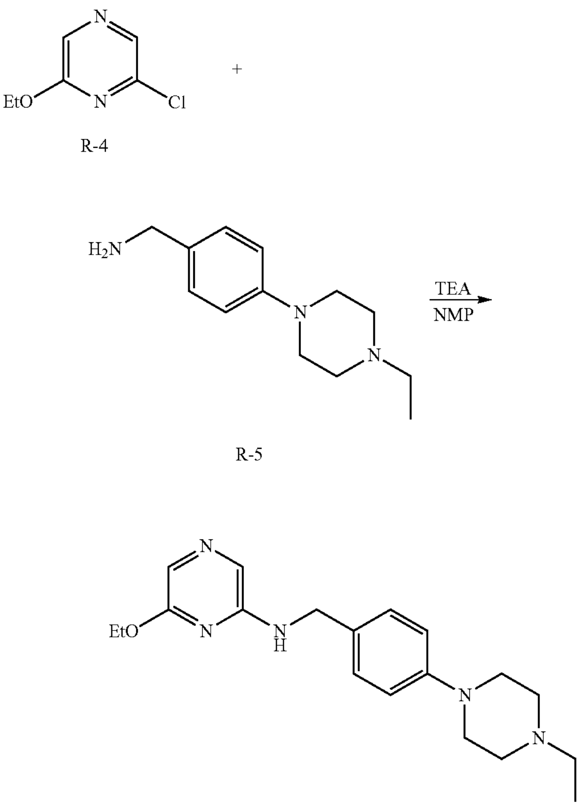

R-4

R-5

Ex 3

R-4 (50 mg, 0.315 mmol), R-5 (69 mg, 0.315 mmol), triethylamine (88 uL, 0.631 mmol) and NMP (1 mL) are added to a pressure tube and sealed. The reaction is stirred and heated to 160° C. for 24 hrs. The reaction is cooled to ambient temperature and purified by preparative HPLC to afford Example 3 (17 mg, 16%).

The following examples are prepared in similar fashion from the appropriate heteroaryl halide and amine: Examples 4-6, 180, and 186-187.

Synthetic Example D: Synthesis of Example 111

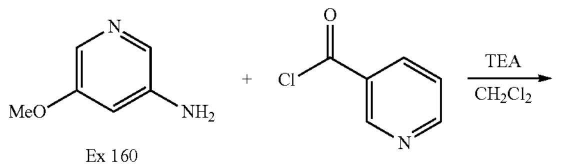

Ex 160

R-6

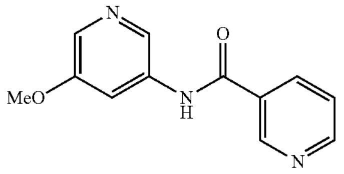

Ex 111

Example 160 (50 mg, 0.36 mmol) and R-6 (96 mg, 0.539 mmol) are dissolved in $CH_2Cl_2$ (1 mL). Triethylamine (0.15 mL, 1.08 mmol) is added and the reaction mixture is stirred at room temperature for 20 hrs. The reaction is diluted with water (2 mL) and $CH_2Cl_2$ (2 mL) and passed through a Telos phase separator. Additional $CH_2Cl_2$ (2 mL) is passed through the phase separator. The combined organic layers are concentrated in vacuo to give crude residue that is purified by preparative HPLC to afford the title compound Example 111 (16 mg, 17%).

The following examples are prepared in similar fashion from the appropriate aniline and acid chloride: Examples 23, 46, and 110.

Synthetic Example E: Synthesis of Example 71

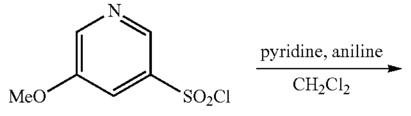

R-9

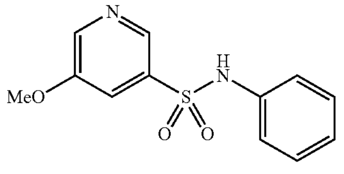

Ex 71

Aniline (22 mg, 0.241 mmol) and pyridine (0.097 mL, 1.20 mmol) are suspended in $CH_2Cl_2$ (5 mL) and cooled to 0° C. and stirred for 5 minutes. To the reaction mixture R-9 (50 mg, 0.241 mmol) is added and the reaction mixture is stirred for 10 minutes. The reaction mixture is concentrated in vacuo. The crude product is purified by preparative HPLC to afford Example 71 (22 mg, 35%).

Synthetic Example F: Synthesis of Example 11

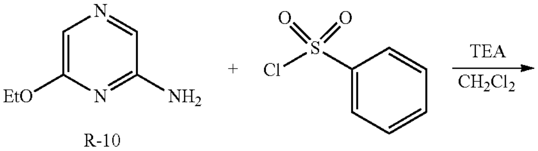

R-10

R-11

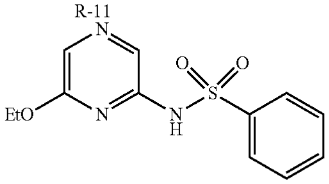

Ex 11

R-10 (50 mg, 0.359 mmol), R-11 (69 uL, 0.539 mmol) are dissolved in $CH_2Cl_2$ (2 mL). Triethylamine (0.15 mL, 1.08 mmol) is added and the reaction mixture is stirred at room temperature for 17 hrs. The mixture is washed with water (2 mL) then passed through a Telos phase separator. Additional $CH_2Cl_2$ (2 mL) is passed through the phase separator. The combined organic layers are concentrated in vacuo to give the crude product. The crude material is purified by preparative HPLC to afford Example 11 (6.0 mg, 5.9%).

The following examples are prepared in similar fashion from the appropriate aniline and sulphonyl chloride: Examples 17, 195, and 207-209.

Synthetic Example G: Synthesis of Example 23

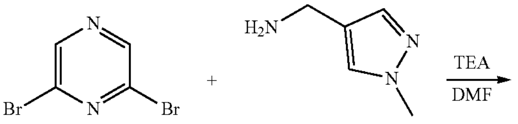

R-12

R-13

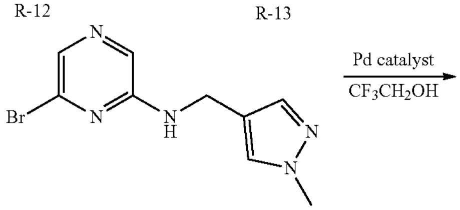

I-4

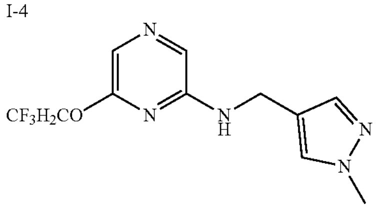

Ex 117

R-12 (5.00 g, 20.6 mmol), triethylamine (8.6 mL, 61.8 mmol) and R-13 (2.29 g, 20.6 mmol) are suspended in DMF (10 mL). The reaction mixture is sealed under a nitrogen atmosphere and stirred at 80° C. for 1 hour then cooled to room temperature and partitioned between EtOAc (20 mL)

and brine (20 mL). The organic phase is separated and concentrated in vacuo to afford a crude material that was purified by flash chromatography (KP—NH $SiO_2$, Heptane/EtOAc) to give I-4 (1.49, 26%).

I-4 (45 mg, 0.169 mmol), (1{E},4{E})-1,5-diphenylpenta-1,4-dien-3-one; palladium (7.7 mg, 8.46 μmol), ditert-butyl-[2-(1,3,5-triphenylpyrazol-4-yl)pyrazol-3-yl]phosphane (8.6 mg, 0.0169 mmol) and potassium hydroxide (11 mg, 0.186 mmol) are suspended in trifluoro ethanol (1 mL) and the mixture is degassed with nitrogen for 10 minutes. The reaction is sealed under a nitrogen atmosphere and stirred at 70° C. for 2 hours. The reaction is diluted with EtOAc (5 mL), filtered, and reduced in vacuo to yield crude product. The crude material is purified by preparative HPLC to afford Example 117 (12 mg, 29%).

The following examples are prepared in similar fashion from the appropriate heteroaryl halide, amine, and alcohol: Examples 13, 15, 35, 74, 96, 108, 115-116, 140, 151, 153, 161-164, 166-169, 172-174, 177, 190, 198-199, and 201-202.

Synthetic Example H: Synthesis of Example 24

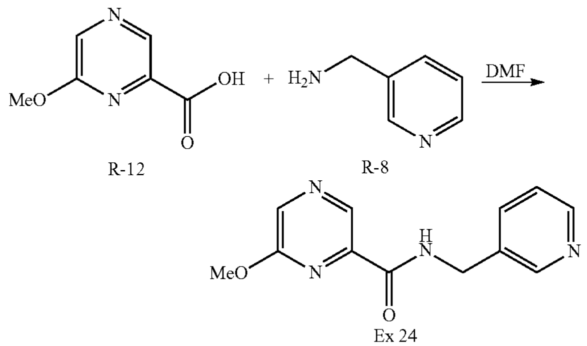

R-12 R-8

Ex 24

R-12 (100 mg, 0.649 mmol), 1-[bis(dimethylamino)methylidene]-1H-[1,2,3]triazolo[4,5-b]pyridin-1-ium 3-oxide hexafluorophosphate (370 mg, 0.973 mmol) and N-ethyl-N-isopropyl-propan-2-amine (0.34 mL, 1.95 mmol) are suspended in DMF (1 mL) at room temperature and stirred for 10 minutes. R-8 (80 mg, 0.714 mmol) is added to the reaction mixture and the reaction is stirred for 2 hours. The reaction mixture is purified by preparative HPLC to afford Example 24 (92 mg, 55%).

The following examples are made in similar fashion from the appropriate amine and acylating agent: Examples 191-193 and 196-197.

Synthetic Example I: Synthesis of Example 31

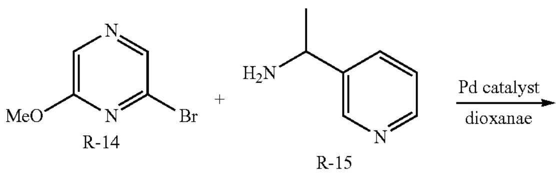

R-14 R-15

-continued

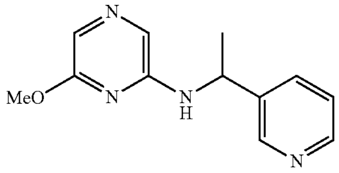

Ex 31

R-15 (0.14 mL, 1.06 mmol), R-14 (100 mg, 0.529 mmol), potassium hydroxide (33 mg, 0.582 mmol), Ditert-butyl-[2-(1,3,5-triphenylpyrazol-4-yl)pyrazol-3-yl]phosphane (27 mg, 0.0529 mmol), (1{E},4{E})-1,5-Diphenylpenta-1,4-dien-3-one; palladium (24 mg, 0.0265 mmol) are suspended then dissolved in 1,4-dioxane (2 mL). The reaction mixture is purged with $N_2$. The reaction mixture is heated to 100° C. for 18 hrs. Additional (1{E},4{E})-1,5-Diphenylpenta-1,4-dien-3-one; palladium (24 mg, 0.0265 mmol) and Ditert-butyl-[2-(1,3,5-triphenylpyrazol-4-yl)pyrazol-3-yl]phosphane (72 mg, 0.0529 mmol) are added and the reaction heated to 120° C. for 24 hrs. The reaction is cooled to room temperature and diluted with water (2 mL). The mixture is extracted with EtOAc (3×2 mL) and the combined organic layers are passed through a Telos phase separator and concentrated in vacuo to give the crude product. The crude product is purified by preparative HPLC to give Example 31 (5.0 mg, 4.1%).

The following examples are prepared in similar fashion from the appropriate heteroaryl halide and amine: Examples 16, 25, 30, 32, 43, and 45.

Synthetic Example J: Synthesis of Example 28

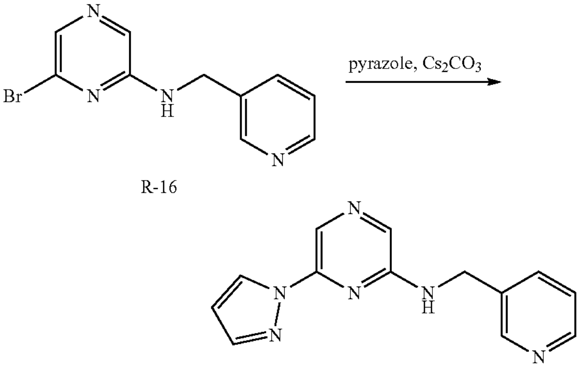

R-16

EX 28

R-16 (100 mg, 0.377 mmol) is dissolved in 1,4-dioxane (3 mL) and pyrazole (51 mg, 0.754 mmol), N,N'-dimethylethane-1,2-diamine (0.020 mL, 0.189 mmol) and cesium carbonate (270 mg, 0.830 mmol) are added. The reaction mixture is degassed for 5 min, then copper iodide (14 mg, 0.0754 mmol) is added. The reaction mixture is stirred at 120° C. for 4 h. The reaction mixture is diluted with EtOAc (10 mL) filtered through glass fiber filter paper. The organic phase is washed with saturated aqueous $NaHCO_3$ (2×10 mL) and concentrated under vacuum. The crude is purified by preparative HPLC to give Example 28 (68 mg, 70%).

Synthetic Example K: Synthesis of Example 63

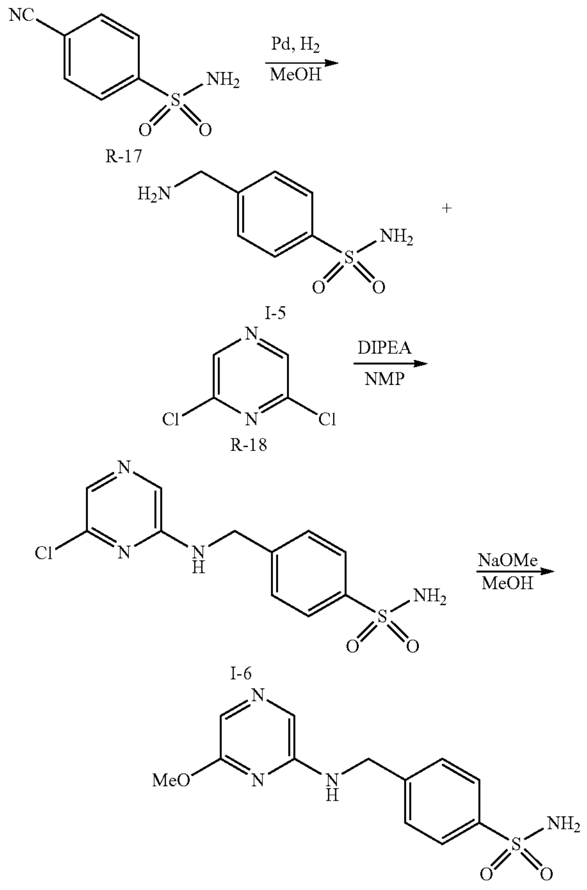

R-17

I-5

R-18

I-6

Ex 63

A mixture of R-17 (6.0 g, 33 mmol), conc. HCl (12 M, 18 mL, 216 mmol) and 10% Pd/C (0.6 g) in MeOH (250 mL) is degassed 3 times and refilled with H2. The reaction mixture is stirred at room temperature under H2 balloon for 4 h. The reaction mixture is filtered, and the filtrate is concentrated under reduced pressure. The residue is washed with EtOAc (100 mL), dried in vacuo to afford I-5 (7.0 g, 95%).

The mixture of I-5 (33 g, 148 mmol), R-18 (20 g, 134.5 mmol) and DIPEA (122 mL, 740 mmol) in NMP (200 mL) is stirred at 100° C. for 16 h. The reaction mixture is cooled to room temperature, diluted with EtOAc (1500 mL), washed with water (200 mL×2) and brine (200 mL×3). The organic layer is concentrated under reduced pressure. The residue is washed with MeOH to afford I-6 (32 g, 79%).

The mixture of I-6 (16 g, 53.7 mmol) in 30% MeONa/MeOH solution (250 mL) is stirred at 50° C. for 18 h. The reaction mixture was cooled to room temperature and diluted with water (50 mL). The mixture is neutralized with 6 mol/L HCl to pH=7 at 0° C., and then concentrated under reduced pressure to about 200 mL. The solid is filtered and washed with water. The resulting solid is dissolved in DMF (60 mL), and purified by prep-HPLC to afford Example 63 (8.5 g, 54%).

Example 211 was prepared in similar fashion.

Synthetic Example L: Synthesis of Example 29

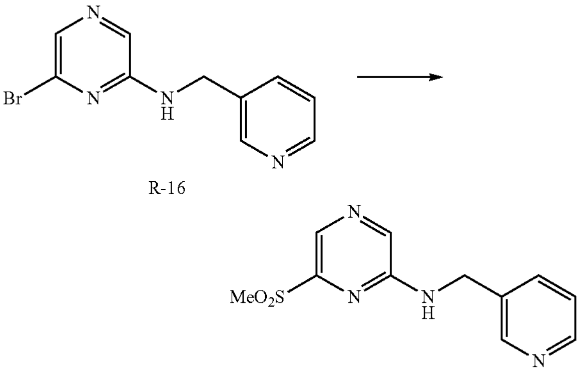

R-16

Ex 29

R-16 (100 mg, 0.377 mmol) is dissolved in DMF (2 mL) and sodium methanesulfinate (96 mg, 0.943 mmol) and N,N'-dimethylethane-1,2-diamine (0.020 mL, 0.189 mmol) are added. The reaction mixture is degassed for 5 min, then copper iodide (14 mg, 0.0754 mmol) is added. The reaction mixture is heated to 120° C. and stirred for 3 h. The reaction mixture is diluted with EtOAc (10 mL) and filtered through glass fiber filter paper. The filtrate is washed with sat. $NaHCO_3$ (10 mL) and the organic phase is dried over $Na_2SO_4$ and concentrated under vacuum. The crude is purified by preparative HPLC to afford Example 29 (45 mg, 44%).

Synthetic Example M: Synthesis of Example 72

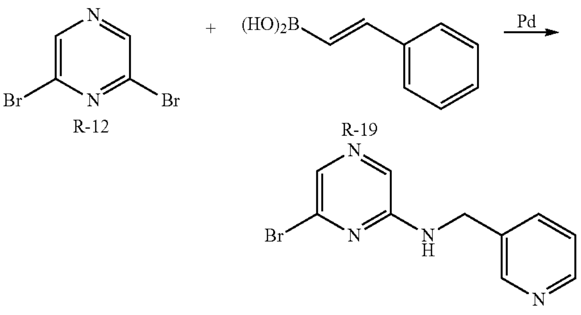

R-12

R-19

Ex 72

Cesium carbonate (1027 mg, 3.15 mmol), cyclopentyl (diphenyl)phosphane; dichloropalladium; iron (77 mg, 0.105 mmol) are suspended in DCE (2 mL) and acetic acid (10 uL). The reaction mixture was stirred room temperature. R-19 (156 mg, 1.05 mmol) and R-12 (240 mg, 1.05 mmol) are added and the reaction mixture is stirred for 3 hrs. The reaction is quenched with water (2 mL) and extracted with DCM (3×2 mL) and the combined organic layers are passed through a Telos phase separator and concentrated in vacuo to give the crude product. The crude product is purified by preparative HPLC to afford Example 72 (65 mg, 24%).

Synthetic Example N: Synthesis of Example 77

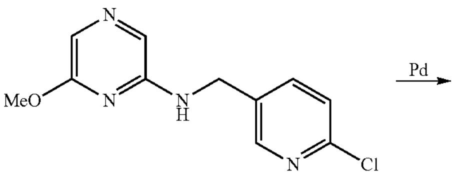

Ex 74

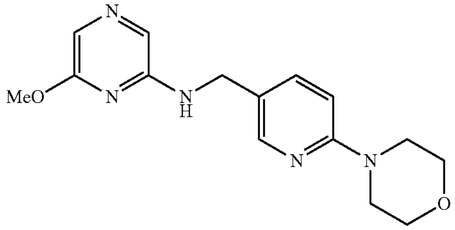

Ex 77

Example 74 (38 mg, 0.391 mmol) and morpholine (0.034 mL, 0.391 mmol) are suspended in toluene (2 mL). The reaction mixture is degassed for 5 min, then dicyclohexyl-[2-(2,4,6-triisopropylphenyl)phenyl]phosphane (9.3 mg, 0.0195 mmol) and (1{E},4{E})-1,5-diphenylpenta-1,4-dien-3-one; palladium (8.9 mg, 9.77 μmol) are added. The reaction mixture is heated at 100° C. and stirred for 2 h then cooled to ambient temperature and partitioned between $CH_2Cl_2$ (3 mL) and water (3 mL). The mixture is filtered and concentrated then purified by preparative HPLC to afford Example 77 (3.0 mg, 5%).

The following examples are prepared in similar fashion from the appropriate heteroaryl halide (Example 74 or Example 95) and amine: Examples 78-84, 98-99, 112, and 122.

Synthetic Example O: Synthesis of Example 107

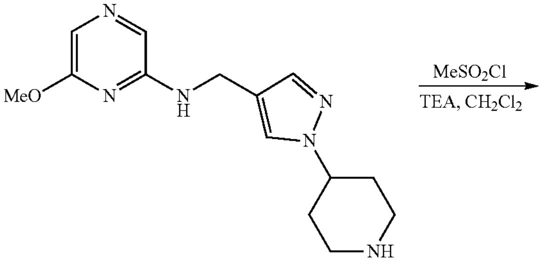

Ex 105

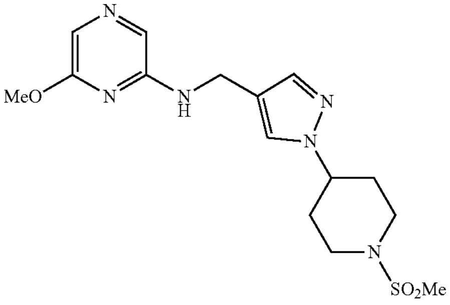

Ex 107

Example 105 (50 mg, 0.173 mmol) and methanesulfonyl chloride (15 uL, 0.191 mmol) are dissolved in $CH_2Cl_2$ (2 mL) and stirred at room temperature. Triethylamine (36 uL, 0.260 mmol) is added and the reaction is purged with $N_2$, stirred for 16 hrs. The reaction is quenched with water (2 mL) and the organic layer separated. The aqueous layer is extracted with $CH_2Cl_2$ (2×2 mL) and the combined organic layers are passed through a Telos phase separator and concentrated in vacuo to give the crude product. The crude product is purified by preparative HPLC to give Example 107 (27 mg, 41%).

The following examples are prepared in similar fashion from the appropriate sulphonylating or acylating agent and Example 20, 105, and 118: Example 133-134, 149-150

Synthetic Example P: Synthesis of Example 124 and 125

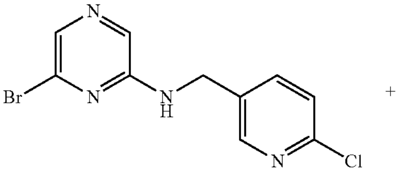

Ex 74

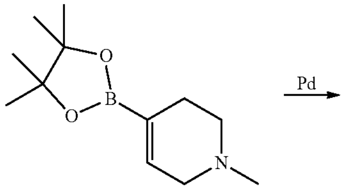

R-20

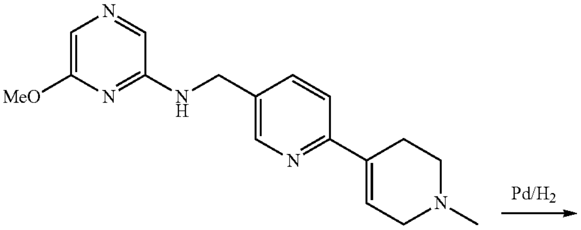

Ex 124

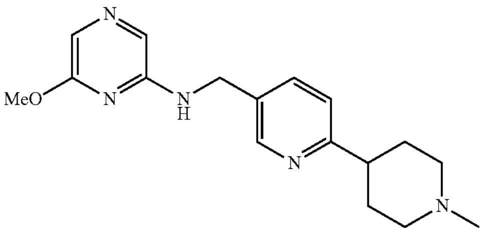

Ex 125

Example 74 (100 mg, 0.399 mmol), R-20 (134 mg, 0.598 mmol) and 2 M aqueous potassium carbonate (0.40 mL, 0.798 mmol) are suspended in 1,4-dioxane (2 mL). The reaction mixture is degassed with nitrogen gas for 5 min before adding cyclopentyl(diphenyl)phosphane; dichloropalladium; iron (29 mg, 0.0399 mmol) and degassing for a further 5 min. The vial is sealed and stirred at 100° C. (external) for 18 h. The reaction mixture is diluted with $CH_2Cl_2$ and washed with brine, separated through a hydrophobic frit and the retained aqueous washed with $CH_2Cl_2$ and separated. The combined organics are concentrated in vacuo to give the crude product. The crude product is purified by preparative HPLC to yield Example 124 (79 mg, 64%).

Example 124 (79 mg, 0.254 mmol) is dissolved in ethanol (5 mL) and sodium acetate (63 mg, 0.761 mmol) and Pd/C (10%, 27 mg, 0.0254 mmol) are added. The reaction mixture is stirred under an atmosphere of H2 for 24 h. The reaction mixture is filtered through a pad of Celite, washed with methanol, and filtrate concentrated in vacuo to yield the crude product. The crude product is purified by preparative HPLC to give Example 125 (65 mg, 82%).

Synthetic Method Q: Synthesis of Example 136

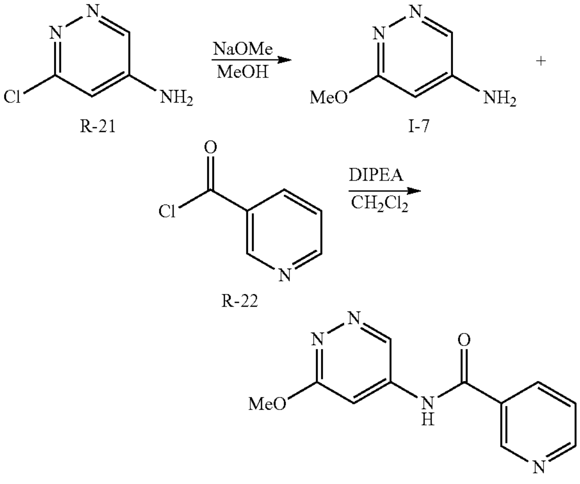

R-21 I-7 R-22 Ex 136

A solution of R-21 (1.0 g, 7.75 mmol) in MeOH (20 ml) is added MeONa (1.255 g, 23.25 mmol), and then is stirred at 75° C. overnight. The mixture is concentrated under reduced pressure. The residue is purified by flash chromatography ($SiO_2$ eluting with 65% of EtOAc in petroleum ether) to give I-7 (500 mg, 51%).

The mixture of I-7 (306 mg, 2.4 mmol) and DIPEA (1.55 g, 12 mmol) in $CH_2Cl_2$ (15 ml) is added R-22 (344 mg, 2.4 mmol) and then stirred at room temperature for 2 h. The mixture is diluted with water (40 ml), and extracted with $CH_2Cl_2$ (150 ml×4). The combined extracts are washed with water, brine, dried, and concentrated under reduced pressure. The residue is purified by prep-HPLC to give Example 136 (100 mg, 18%).

Example 137 was prepared in similar fashion from the appropriate acylating agent.

Synthetic Method R: Synthesis of Example 175

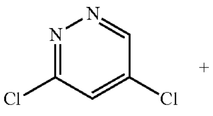

R-23

-continued

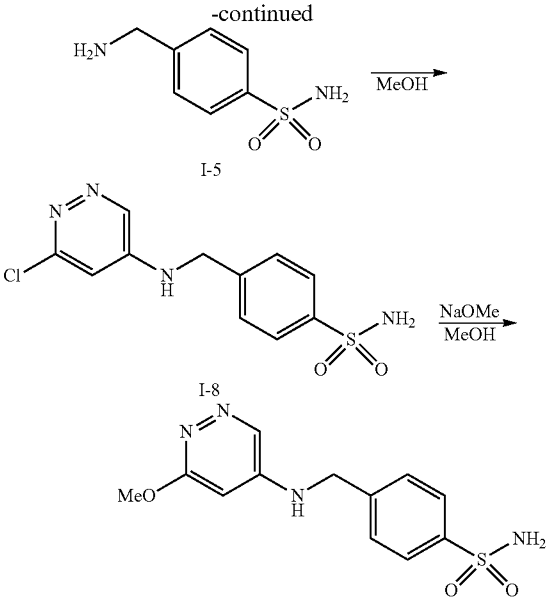

I-5 I-8 Ex 175

To a solution of R-23 (5.5 g, 37.6 mmol) in methanol (100 ml) is added DIPEA (9.6 g, 75 mmol) and I-5 (7.0 g, 37.6 mmol). The reaction mixture is heated at 80° C. overnight. The mixture is concentrated under reduced pressure. The residue is purified by flash chromatography ($SiO_2$, 0 to 15% of methanol in dichloromethane) to afford I-8 (3.4 g, 30%).

A suspension of I-8 (3.4 g, 11.4 mmol) in a solution of MeONa in methanol (30%, 10 ml, 57 mmol) is stirred at 80° C. overnight. Water (2 ml) is added, and then concentrated in vacuo. The residue is purified by flash chromatography ($SiO_2$, 0 to 20% of methanol in dichloromethane) to give Example 175 (1.2 g, 36%).

The following examples are prepared in similar fashion from the appropriate amines: Examples 95 and 176.

Synthetic Method S: Synthesis of Example 138

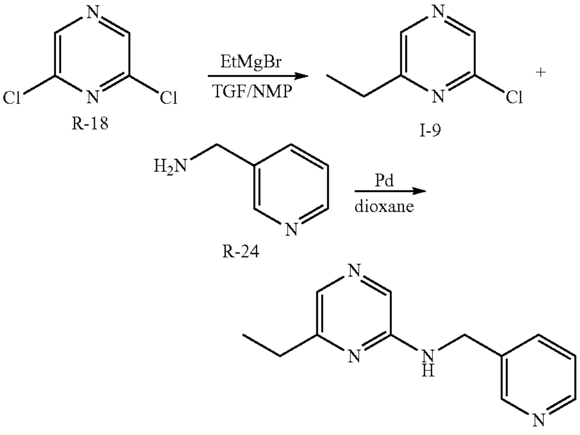

R-18 I-9 R-24 Ex 138

To a solution of R-18 (1 g, 6.75 mmol) and iron acetylacetonate (119 mg, 0.33 mmol) in THF (5 mL) and NMP (0.5 mL) is added EtMgBr (3 mol/L in THF, 3.3 mL, 9.9 mmol) dropwise at 0° C., and then stirred at 0° C. for 3 h.

The reaction mixture is poured into saturated aqueous $NH_4Cl$ (20 mL), and extracted with EtOAc (20 mL×2). The combined organic phases are dried over $Na_2SO_4$, and concentrated under reduced pressure to give I-9, which is used in the next step without further purification.

To a solution of I-9 (150 mg, 1 mmol), R-24 (130 mg, 1.2 mmol), BINAP (62 mg, 0.1 mmol), $Pd(dba)_3$ (45.8 mg, 0.05 mmol) and t-BuONa (144 mg, 1.5 mmol) in dioxane (3 mL) is stirred at 85° C. for 2 h under $N_2$ atmosphere. The mixture is concentrated under reduced pressure. The residue is partitioned between EtOAc (20 mL) and water (15 mL). The organic phase is dried, and concentrated under reduced pressure. The residue is purified by prep-HPLC to afford Example 138 (55 mg, 24.3%).

Example 200 was made in similar fashion.

Synthetic Method T: Synthesis of Example 139

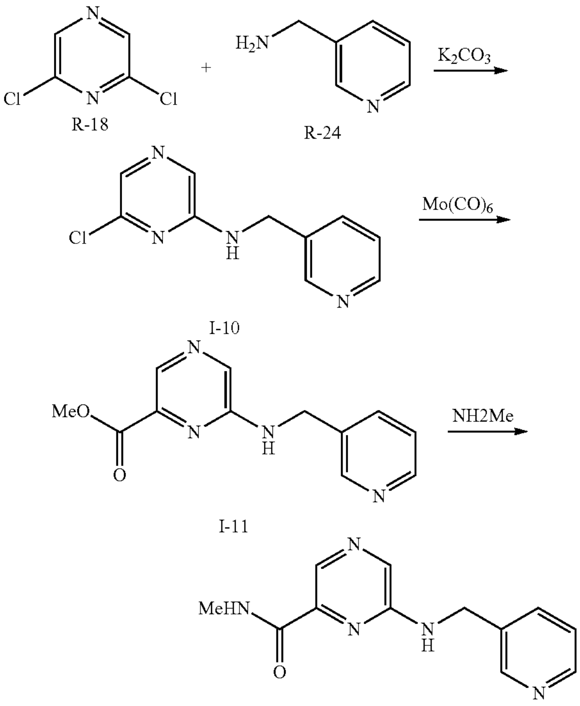

R-18 R-24 I-10 I-11 Ex139

A mixture of R-18 (5.0 g, 33.7 mmol), R-24 (4.37 g, 40.5 mmol), and $K_2CO_3$ (7.0 g, 50.6 mmol) in 1,4-dioxane (100 ml) is stirred at 100° C. overnight, and then concentrated to dryness under reduced pressure. The residue is partitioned between water (100 ml) and ethyl acetate (100 ml). The organic layer is washed with brine, and concentrated in vacuo. The residue is purified by flash chromatography ($SiO_2$, ethyl acetate) to give I-10 (3.0 g, yield=40%).

To a solution of I-10 (3.0 g, 13.6 mmol) in DMF (20 ml) and methanol (5 ml) is added $Mo(CO)_6$ (2.15 g, 8.16 mmol), $Pd_2(dba)_3$ (1.2 g, 1.36 mmol), and dppf (1.5 g, 2.72 mmol). The mixture is flushed with $N_2$, and then sealed. The mixture is stirred at 130° C. overnight. The mixture is poured into water (100 ml), and extracted with ethyl acetate (100 ml×3). The combined extracts are washed with water, brine, and concentrated in vacuo. The residue is purified by flash chromatography ($SiO_2$, 0 to 10% of methanol in DCM) to give I-11 (2.2 g, 67%).

To a solution of methylamine in tetrahydrofuran (1 mol/L, 2 mL, 2 mmol) is added I-11 (100 mg, 0.41 mmol), and then stirred at room temperature for 4 hours. The mixture is filtered, and the filtrate is concentrated in vacuo. The residue is purified by flash chromatography ($SiO_2$, 7% of methanol in dichloromethane) to give Example 139 (20 mg, 20%).

The following examples were made in similar fashion: Example 212-213.

Synthetic Method U: Synthesis of Example 94

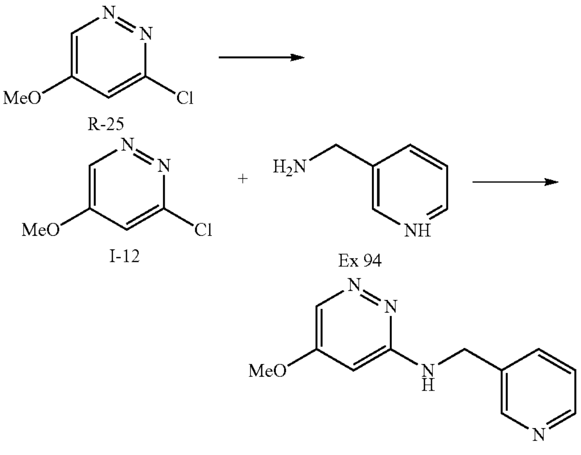

R-25 I-12 Ex 94 Ex 94

A suspension of R-25 (1.8 g, 14 mmol) in phosphoryl trichloride (25 ml) is rapidly heated to 75° C. under nitrogen and stirred until all the solid had dissolved in the reaction mixture. The mixture is cooled to room temperature, and then concentrated in vacuo. The residue is diluted with dichloromethane (100 ml), and washed with water (60 ml×2). The organic layer is filtered through a pad of silica. The silica gel is washed with EtOAc:petroleum ether (1:1). The filtrate is concentrated in vacuo to give I-12 (1.09 g, 52%).

The mixture of I-12 (200 mg, 1.4 mmol), R-24 (0.19 ml, 1.4 mmol), BINAP (173 mg, 0.27 mmol), t-BuONa (200 mg, 2 mmol), and $Pd_3$ $(dba)_2$ (127 mg, 0.14 mmol) in dioxane (4 ml) is refluxed at 100° C. for 1 h under nitrogen. The mixture is added water (30 ml), and extracted with EtOAc (50 mL×2). The organic phase is concentrated in vacuo, and the residue is purified by Prep-HPLC to give Example 94 (20 mg, 15%).

Example 135 is prepared in similar fashion from the appropriate amine.

Synthetic Method V: Synthesis of Example 188 and 189

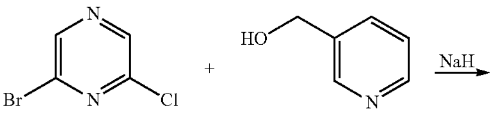

R-26 R-27

-continued

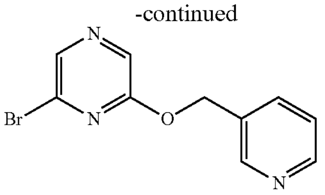

+

Ex 188

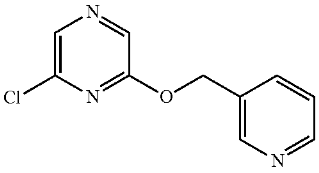

Ex 189

R-26 (0.22 mL, 1.03 mmol) and R-27 (113 mg, 1.03 mmol) are suspended in 1,4-dioxane (2 mL) and to this is added sodium hydride (60%, 45 mg, 1.14 mmol). The resulting mixture is left to stir for 2 hours at room temperature under a nitrogen atmosphere. The reaction is cooled to room temperature and quenched with water (5 mL), partitioned between ethyl acetate (20 mL) and brine (20 mL). The organic phase is separated and concentrated in vacuo. The crude material is purified by preparative HPLC afford Example 188 (26 mg, 9.4%) and Example 189 (35 mg, 15%).

Example 2. Characterization of Compounds

LCMS methods:

Analytical LC/MS Analysis Method A:

ESI+/− ion mode 150-850 Da

Column: Phenomenex Kinetix-XB C18, Part No. 00D-4498-AN, 2.1×100 mm, 1.7 μm

Temperature: 40° C.

Gradient:

| Time (min) | 0.1% formic acid in water | acetonitrile | Flow (mL/min) |
|---|---|---|---|
| 0 | 95% | 5% | 0.6 |
| 5.30 | 0% | 100% | 0.6 |
| 5.80 | 0% | 100% | 0.6 |
| 5.82 | 95% | 5% | 0.6 |
| 7.00 | 95% | 5% | 0.6 |

Analytical LC/MS Analysis Method B:

ESI+/− ion mode 150-850 Da

Column: Waters UPLC® BEH™ C18, Part No. 186002352, 2.1×100 mm, 1.7 μm

Temperature: 40° C.

Gradient:

| Time (min) | 2 mM aqueous ammonium bicarbonate | acetonitrile | Flow (mL/min) |
|---|---|---|---|
| 0 | 95% | 5% | 0.6 |
| 5.30 | 0% | 100% | 0.6 |
| 5.80 | 0% | 100% | 0.6 |
| 5.82 | 95% | 5% | 0.6 |
| 7.00 | 95% | 5% | 0.6 |

Analytical LC/MS Analysis Method C:

ESI+/− ion mode 100-1000 Da

Column: HALO C18 2.7 μm 30×4.6 mm column

Temperature: 40° C.

Gradient:

| Time (min) | 0.01% TFA in water | 0.01% TFA in acetonitrile | Flow (mL/min) |
|---|---|---|---|
| 0 | 95% | 5% | 2.2 |
| 1.0 | 5% | 95% | 2.2 |

Analytical LC/MS Analysis Method D:

ESI+/− ion mode 150-850 Da

Column: Phenomenex Gemini NX C18, Part No. 00D-4453-B0, 3.0 μm 2.0×100 mm column Temperature: 40° C.

Gradient:

| Time (min) | 2 mM aqueous ammonium bicarbonate | Acetonitrile | Flow (mL/min) |
|---|---|---|---|
| 0.00 | 95% | 5% | 0.6 |
| 5.50 | 0% | 100% | 0.6 |
| 5.90 | 0% | 100% | 0.6 |
| 5.92 | 95% | 5% | 0.6 |
| 7.00 | 95% | 5% | 0.6 |

Analytical LC/MS Analysis Method E:

ESI+/− ion mode 100-1000 Da

Column: XBridge C18, 3.5 μm 4.6×50 mm column

Temperature: 50° C.

Gradient:

| Time (min) | 10 mM aqueous ammonium bicarbonate | Acetonitrile | Flow (mL/min) |
|---|---|---|---|
| 0.00 | 90% | 10% | 1.5 |
| 1.50 | 5% | 95% | 1.5 |

Analytical LC/MS Analysis Method F:

ESI+/− ion mode 100-1000 Da

Column: XBridge C18, 3.5 μm 4.6×50 mm column

Temperature: 40° C.

Gradient:

| Time (min) | 10 mM aqueous ammonium bicarbonate | Acetonitrile | Flow (mL/min) |
|---|---|---|---|
| 0.00 | 90% | 10% | 1.6 |
| 1.40 | 5% | 95% | 1.6 |
| 3.00 | 5% | 95% | 1.6 |

Analytical LC/MS Analysis Method G:

ESI+/− ion mode 100-1000 Da

Column: XBridge SB-C18, 3.5 μm 4.6×50 mm column

Temperature: 40° C.

Gradient:

| Time (min) | 10 mM aqueous ammonium bicarbonate | Acetonitrile | Flow (mL/min) |
|---|---|---|---|
| 0.00 | 95% | 5% | 2.0 |
| 1.40 | 5% | 95% | 2.0 |
| 3.00 | 5% | 95% | 2.0 |

Analytical LC/MS Analysis Method H:

ESI+/− ion mode 100-1000 Da

Column: XBridge C18, 3.5 μm 4.6×50 mm column

Temperature: 40° C.

Gradient:

| Time (min) | 10 mM aqueous ammonium bicarbonate | Acetonitrile | Flow (mL/min) |
|---|---|---|---|
| 0.00 | 95% | 5% | 2.0 |
| 1.20 | 5% | 95% | 2.0 |

Analytical LC/MS Analysis Method I:

ESI+/− ion mode 100-1000 Da

Column: XBridge C18, 3.5 μm 4.6×50 mm column

Temperature: 50° C.

Gradient:

| Time (min) | 10 mM aqueous ammonium bicarbonate | Acetonitrile | Flow (mL/min) |
|---|---|---|---|
| 0.00 | 90% | 10% | 1.8 |
| 1.50 | 5% | 95% | 1.8 |

Analytical LC/MS Analysis Method J:

ESI+/− ion mode 100-1000 Da

Column: Zorbox SB-C18, 1.8 μm 4.6×30 mm column

Temperature: 40° C.

Gradient:

| Time (min) | 0.01% TFA in water | 0.01% TFA in Acetonitrile | Flow (mL/min) |
|---|---|---|---|
| 0.00 | 95% | 5% | 1.8 |
| 1.30 | 5% | 95% | 1.8 |
| 2.00 | 5% | 95% | 1.8 |

Results are presented in Table 1:

TABLE 1

| Example | LCMS method | RT (min) | Mol ion (m/z) |
|---|---|---|---|
| 1 | — | nd | nd |
| 2 | — | nd | nd |
| 3 | A | 1.21 | 343 |
| 4 | A | 1.01 | 231 |
| 5 | B | 2.92 | 274 |
| 6 | B | 2.64 | 342 |
| 7 | A | 1.53 | 342 |
| 8 | A | 0.94 | 329 |
| 9 | A | 1.14 | 245 |
| 10 | A | 3.20 | 230 |
| 11 | A | 2.63 | 280 |
| 12 | D | 1.99 | 217 |

TABLE 1-continued

| Example | LCMS method | RT (min) | Mol ion (m/z) |
|---|---|---|---|
| 13 | D | 2.53 | 245 |
| 14 | D | 0.79 | 202 |
| 15 | D | 3.27 | 273 |
| 16 | D | 2.16 | 230 |
| 17 | A | 1.67 | 267 |
| 18 | A | 3.52 | 222 |
| 19 | A | 3.02 | 230 |
| 20 | E | 1.547 | 206.1 |
| 21 | A | 1.61 | 220 |
| 22 | E | 1.524 | 218.1 |
| 23 | A | 3.51 | 281 |
| 24 | D | 1.75 | 245 |
| 25 | D | 2.01 | 230 |
| 26 | A | 1.33 | 267 |
| 27 | A | 1.60 | 267 |
| 28 | A | 2.13 | 253 |
| 29 | D | 1.52 | 265 |
| 30 | D | 2.41 | 244 |
| 31 | A | 0.94 | 231 |
| 32 | A | 3.00 | 230 |
| 33 | A | 3.28 | 244 |
| 34 | B | 2.04 | 230 |
| 35 | B | 2.30 | 231 |
| 36 | B | 3.16 | 246 |
| 37 | B | 3.02 | 246 |
| 38 | B | 3.01 | 246 |
| 39 | B | 3.10 | 234 |
| 40 | B | 1.51 | 218 |
| 41 | E | 1.727 | 224.1 |
| 42 | B | 2.67 | 219 |
| 43 | A | 1.00 | 247 |
| 44 | A | 2.30 | 251 |
| 45 | A | 2.85 | 314 |
| 46 | A | 3.95 | 315 |
| 47 | A | 1.93 | 273 |
| 48 | A | 1.31 | 271 |
| 49 | A | 1.53 | 256 |
| 50 | A | 1.69 | 210 |
| 51 | B | 1.73 | 220 |
| 52 | A | 1.80 | 223 |
| 53 | A | 1.58 | 207 |
| 54 | A | 1.65 | 220 |
| 55 | B | 1.71 | 220 |
| 56 | A | 1.95 | 221 |
| 57 | B | 1.70 | 220 |
| 58 | A | 2.30 | 206 |
| 59 | B | 2.73 | 219 |
| 60 | A | 1.42 | 220 |
| 61 | F | 1.295 | 206.2 |
| 62 | B | 2.05 | 223 |
| 63 | E | 1.633 | 295 |
| 64 | A | 1.65 | 259 |
| 65 | A | 1.71 | 259 |
| 66 | E | 1.463 | 233.1 |
| 67 | A | 2.73 | 274 |
| 68 | A | 1.56 | 207 |
| 69 | A | 1.67 | 220 |
| 70 | A | 1.81 | 237 |
| 71 | A | 2.48 | 265 |
| 72 | A | 3.62 | 263 |
| 73 | A | 2.78 | 282 |
| 74 | A | 3.47 | 215 |
| 75 | D | 2.82 | 215 |
| 76 | A | 2.07 | 260 |
| 77 | A | 1.17 | 302 |
| 78 | A | 1.66 | 314 |
| 79 | A | 1.00 | 357 |
| 80 | A | 1.05 | 316 |
| 81 | B | 2.07 | 301 |
| 82 | B | 2.36 | 315 |
| 83 | A | 1.13 | 343 |
| 84 | A | 1.39 | 300 |
| 85 | A | 2.89 | 234 |
| 86 | A | 2.87 | 234 |
| 87 | A | 3.07 | 230 |
| 88 | A | 1.83 | 257 |
| 89 | A | 1.72 | 257 |

TABLE 1-continued

| Example | LCMS method | RT (min) | Mol ion (m/z) |
|---|---|---|---|
| 90 | A | 2.18 | 256 |
| 91 | A | 2.66 | 285 |
| 92 | A | 2.13 | 248 |
| 93 | A | 1.76 | 264 |
| 94 | H | 1.135 | 217.1 |
| 95 | H | 1.154 | 217.1 |
| 97 | A | 1.96 | 252.1, 254.1 |
| 98 | A | 1.09 | 330 |
| 99 | A | 3.35 | 416 |
| 100 | A | 3.55 | 308, 310 |
| 101 | A | 3.27 | 294, 296 |
| 102 | D | 0.61 | 203 |
| 103 | A | 2.95 | 389 |
| 104 | B | 2.03 | 277 |
| 105 | C | 0.817 | 289.2 |
| 106 | A | 2.87 | 288 |
| 107 | A | 1.98 | 367 |
| 108 | I | 1.452 | 232.1 |
| 109 | A | 3.26 | 294.0, 296.0 |
| 110 | A | 1.59 | 229 |
| 111 | A | 1.01 | 230 |
| 112 | A | 1.16 | 316 |
| 113 | B | 2.31 | 303 |
| 114 | B | 1.94 | 315 |
| 115 | D | 2.88 | 296 |
| 116 | D | 2.28 | 270 |
| 117 | D | 3.51 | 288 |
| 118 | B | 1.83 | 232 |
| 119 | A | 1.00 | 303 |
| 120 | A | 1.04 | 317 |
| 121 | A | 1.73 | 221 |
| 122 | A | 1.19 | 344 |
| 123 | A | 3.59 | 400 |
| 124 | A | 0.96 | 312 |
| 125 | B | 2.45 | 314 |
| 126 | A | 1.31 | 300 |
| 127 | A | 2.09 | 294 |
| 128 | A | 2.54 | 241 |
| 129 | A | 2.53 | 241 |
| 130 | A | 1.71 | 336 |
| 131 | B | 2.71 | 341 |
| 132 | A | 1.98 | 401 |
| 133 | A | 1.54 | 310 |
| 134 | A | 1.76 | 331 |
| 135 | H | 1.05 | 206.1 |
| 136 | G | 1.196 | 231.1 |
| 137 | G | 1.221 | 232.1 |
| 138 | G | 1.385 | 215.1 |
| 139 | G | 1.12 | 244.1 |
| 140 | E | 1.336 | 233.1 |
| 141 | A | 1.28 | 294 |
| 142 | A | 2.25 | 293 |
| 143 | A | 3.44 | 300 |
| 144 | A | 2.37 | 274 |
| 145 | A | 1.34 | 233 |
| 146 | A | 2.17 | 284 |
| 147 | A | 1.01 | 343 |
| 148 | A | 1.19 | 357 |
| 149 | A | 2.16 | 277 |
| 150 | A | 1.88 | 284 |
| 151 | A | 1.01 | 277 |
| 152 | E | 1.602 | 140.1 |
| 153 | E | 1.503 | 232.1 |
| 154 | G | 1.304 | 212.1 |
| 155 | A | 1.35 | 328 |
| 156 | A | 2.53 | 323 |
| 157 | A | 1.41 | 247 |
| 158 | A | 1.98 | 284 |
| 159 | B | 1.19 | 167 |
| 160 | D | 1.09 | 249 |
| 161 | D | 1.98 | 140 |
| 162 | D | 2.68 | 140 |
| 163 | A | 2.81 | 216 |
| 164 | B | 1.24 | 167 |
| 165 | D | 2.19 | 111 |
| 166 | B | 1.46 | 197 |
| 167 | A | 1.05 | 233 |
| 168 | A | 2.45 | 283 |
| 169 | A | 2.67 | 297 |
| 170 | J | 1.111 | 248.2 |
| 171 | D | 2.55 | 139 |
| 172 | B | 1.49 | 183 |
| 173 | B | 1.71 | 197 |
| 174 | A | 1.28 | 198 |
| 175 | H | 1.148 | 295 |
| 176 | H | 1.022 | 233.1 |
| 177 | E | 1.739 | 304.1 |
| 178 | B | 2.15 | 299 |
| 179 | B | 2.13 | 318 |
| 180 | A | 1.15 | 342 |
| 181 | B | 2.42 | 313 |
| 182 | B | 2.42 | 298 |
| 183 | A | 1.83 | 232 |
| 184 | A | 1.34 | 245 |
| 185 | A | 1.19 | 231 |
| 186 | A | 1.10 | 265.0, 267.0 |
| 187 | A | 0.97 | 221 |
| 188 | A | 1.42 | 266.0, 268.0 |
| 189 | A | 1.30 | 222 |
| 190 | A | 1.43 | 232 |
| 191 | A | 1.95 | 245 |
| 192 | A | 2.82 | 244 |
| 193 | A | 1.66 | 182 |
| 194 | — | nd | nd |
| 195 | A | 1.70 | 218 |
| 196 | D | 2.69 | 244 |
| 197 | D | 2.86 | 230 |
| 198 | D | 2.94 | 293 |
| 199 | D | 3.30 | 285 |
| 200 | A | 2.51 | 229 |
| 201 | A | 1.13 | 235 |
| 202 | A | 1.04 | 231 |
| 203 | B | 1.93 | 217 |
| 204 | B | 2.09 | 231 |
| 205 | A | 3.25 | 232 |
| 206 | A | 1.72 | 234 |
| 207 | A | 2.50 | 279 |
| 208 | A | 1.03 | 279 |
| 209 | A | 1.99 | 265 |
| 210 | A | 2.06 | 224 |
| 211 | A | 1.83 | 295 |
| 212 | H | 1.075 | 230.1 |
| 213 | G | 1.143 | 258.1 |
| 214 | A | 0.80 | 206 |
| 215 | H | 1.057 | 217.1 |
| 216 | B | 3.65 | 377 |
| 217 | D | 2.12 | 139 |
| 218 | A | 1.94 | 188.0, 190.0 |
| 219 | D | 2.42 | 110 |

Example 3: ARM-SAM-TIR SARM1 IC50 Assay

This Example describes an assay of ARM-SAM-TIR NADase activity and use of this assay to measure the efficacy of compounds of Formula I to block SARM1 mediated NAD+ cleavage. This assay is optimized in such a way as to characterize the efficacy of the compounds in Formula I to inhibit SARM1 activity and to calculate an IC50 value for each compound. This assay makes use of full length SARM1, which encompasses the ARM, SAM and TIR domains. As demonstrated herein, expression of this fragment without the autoinhibitory N-terminal domain generates a constitutively active enzyme that cleaves NAD+.

Preparation of ARM-SAM-TIR Lysate (STL)

NRK1-HEK293T cells were seeded onto 150 $cm^2$ plates at 20×106 cells per plate. The next day, the cells were transfected with 15 μg ARM-SAM-TIR expression plasmid, SEQ ID NO: 1.

(SEQ ID NO: 1)

```
GCGATCGCGGCTCCCGACATCTTGGACCATTAGCT
CCACAGGTATCTTCTTCCCTCTAGTGGTCATAACA
GCAGCTTCAGCTACCTCTCAATTCAAAAAACCCCT
CAAGACCCGTTTAGAGGCCCCAAGGGGTTATGCTA
TCAATCGTTGCGTTACACACACAAAAAACCAACAC
ACATCCATCTTCGATGGATAGCGATTTTATTATCT
AACTGCTGATCGAGTGTAGCCAGATCTAGTAATCA
ATTACGGGGTCATTAGTTCATAGCCCATATATGGA
GTTCCGCGTTACATAACTTACGGTAAATGGCCCGC
CTGGCTGACCGCCCAACGACCCCCGCCCATTGACG
TCAATAATGACGTATGTTCCCATAGTAACGCCAAT
AGGGACTTTCCATTGACGTCAATGGGTGGAGTATT
TACGGTAAACTGCCCACTTGGCAGTACATCAAGTG
TATCATATGCCAAGTACGCCCCCTATTGACGTCAA
TGACGGTAAATGGCCCGCCTGGCATTATGCCCAGT
ACATGACCTTATGGGACTTTCCTACTTGGCAGTAC
ATCTACGTATTAGTCATCGCTATTACCATGCTGAT
GCGGTTTTGGCAGTACATCAATGGGCGTGGATAGC
GGTTTGACTCACGGGGATTTCCAAGTCTCCACCCC
ATTGACGTCAATGGGAGTTTGTTTTGGCACCAAAA
TCAACGGGACTTTCCAAAATGTCGTAACAACTCCG
CCCCATTGACGCAAATGGGCGGTAGGCGTGTACGG
TGGGAGGTCTATATAAGCAGAGCTGGTTTAGTGAA
CCGTCAGATCAGATCTTTGTCGATCCTACCATCCA
CTCGACACACCCGCCAGCGGCCGCTGCCAAGCTTC
CGAGCTCTCGAATTCAAAGGAGGTACCCACcatgG
CCATGCATCACCACCACCATCATAGCTCCGGCGTC
GACCTCGGCACCGAGAATTTATATTTCCAAAGCGG
CCTCAATGATATCTTCGAGGCCCAGAAGATCGAGT
GGCACGAGGGCAGCTCCGACCTCGCCGTGCCCGGT
CCCGATGGAGGCGGAGGCACTGGTCCTTGGTGGGC
TGCTGGCGGCAGAGGCCCTAGAGAAGTGAGCCCCG
GTGCTGGCACCGAGGTGCAAGACGCTCTGGAGAGG
GCTCTGCCCGAACTGCAGCAAGCTCTGTCCGCTTT
AAAGCAAGCTGGAGGAGCTAGAGCCGTCGGCGCCG
GACTGGCCGAAGTGTTCCAGCTCGTGGAGGAAGCT
```

-continued

```
TGGTTATTACCCGCTGTGGGAAGAGAGGTCGCCCA
AGGTCTGTGTGACGCCATTCGTCTGGACGGAGGTT
TAGACTTATTACTGAGGCTGCTGCAAGCTCCCGAA
CTGGAGACAAGGGTCCAAGCTGCTCGTCTGCTGGA
GCAGATCCTCGTGGCCGAGAATCGTGACAGAGTGG
CTAGAATCGGTTTAGGCGTCATCCTCAATTTAGCC
AAAGAGAGGGAGCCCGTTGAGCTGGCCAGAAGCGT
CGCTGGCATCCTCGAGCACATGTTCAAGCATTCCG
AGGAGACTTGTCAGAGACTGGTCGCCGCCGGAGGA
CTCGATGCTGTTTTATACTGGTGCAGAAGGACAGA
CCCCGCTTTACTGAGGCATTGTGCTCTGGCCCTCG
GCAATTGCGCTTTACATGGAGGCCAAGCCGTCCAG
AGAAGGATGGTGGAGAAAAGAGCCGCCGAGTGGCT
GTTCCCTTTAGCCTTCTCCAAAGAAGACGAACTGT
TACGTCTGCATGCTTGTCTCGCTGTCGCTGTTTTA
GCCACCAACAAGGAGGTGGAAAGGGAAGTGGAAAG
AAGCGGAACACTGGCTTTAGTCGAACCTCTGGTGG
CTTCTTTAGATCCCGGAAGGTTTGCCAGATGTCTG
GTCGACGCCAGCGATACCTCCCAAGGAAGAGGCCC
CGACGATCTCCAGAGACTGGTGCCTCTGCTGGACA
GCAATCGTCTGGAGGCCCAATGTATTGGCGCCTTC
TATCTCTGCGCCGAAGCCGCCATCAAGTCTTTACA
AGGTAAGACCAAGGTGTTCTCCGACATTGGAGCCA
TCCAATCTTTAAAGAGGCTGGTGAGCTATTCCACC
AACGGCACAAAAAGCGCTTTAGCCAAAAGAGCTTT
AAGACTGCTGGGCGAAGAGGTGCCTAGGCCCATTT
TACCTTCCGTGCCTAGCTGGAAGGAGGCCGAGGTG
CAGACTTGGCTGCAGCAGATCGGCTTTAGCAAATA
TTGCGAATCCTTTAGGGAGCAGCAAGTTGACGGCG
ATTTATTATTAAGGCTGACCGAGGAAGAGCTCCAG
ACAGATTTAGGCATGAAAAGCGGCATCACTCGTAA
GAGGTTCTTTCGTGAGCTCACCGAACTGAAGACCT
TCGCCAACTACTCCACTTGTGATCGTAGCAATTTA
GCTGATTGGCTCGGATCCCTCGATCCCAGATTTCG
TCAGTACACCTATGGACTCGTCTCTTGTGGACTGG
ACAGATCTTTACTGCATCGTGTGAGCGAGCAACAG
CTGCTGGAAGATTGCGGCATCCATTTAGGAGTGCA
CAGAGCCAGAATTCTGACCGCCGCTAGAGAGATGC
TGCATTCCCCTCTCCCTTGTACCGGAGGCAAGCCT
AGCGGAGACACCCCCGACGTGTTCATCAGCTATCG
```

-continued

TAGAAACAGCGGAAGCCAGCTGGCCTCTTTACTGA
AGGTCCATTTACAGCTGCACGGATTTAGCGTCTTC
ATCGACGTGGAGAAACTGGAGGCTGGCAAGTTCGA
GGACAAGCTGATCCAGTCCGTGATGGGCGCTAGGA
ATTTCGTTTTAGTGCTCAGCCCCGGCGCTCTGGAT
AAATGCATGCAAGATCATGACTGTAAGGACTGGGT
CCACAAGGAAATCGTGACCGCTCTGTCTTGTGGCA
AGAACATCGTCCCCATCATCGACGGCTTCGAATGG
CCCGAGCCTCAAGTTCTCCCCGAAGATATGCAAGC
TGTTTTAACCTTCAATGGAATCAAGTGGAGCCACG
AGTACCAAGAAGCCACAATCGAGAAGATCATTCGT
TTTCTGCAAGGTAGATCCTCCAGAGATTCCTCCGC
TGGCAGCGACACATCTTTAGAGGGCGCCGCCCCTA
TGGGTCCTACCTAATAATctagAAGTTGTCTCCTC
CTGCACTGACTGACTGATACAATCGATTTCTGGAT
CCGCAGGCCTCTGCTAGCTTGACTGACTGAGATAC
AGCGTACCTTCAGCTCACAGACATGATAAGATACA
TTGATGAGTTTGGACAAACCACAACTAGAATGCAG
TGAAAAAAATGCTTTATTTGTGAAATTTGTGATGC
TATTGCTTTATTTGTAACCATTATAAGCTGCAATA
AACAAGTTAACAACAACAATTGCATTCATTTTATG
TTTCAGGTTCAGGGGGAGGTGTGGGAGGTTTTTTA
AAGCAAGTAAAACCTCTACAAATGTGGTATTGGCC
CATCTCTATCGGTATCGTAGCATAACCCCTTGGGG
CCTCTAAACGGGTCTTGAGGGGTTTTTTGTGCCCC
TCGGGCCGGATTGCTATCTACCGGCATTGGCGCAG
AAAAAAATGCCTGATGCGACGCTGCGCGTCTTATA
CTCCCACATATGCCAGATTCAGCAACGGATACGGC
TTCCCCAACTTGCCCACTTCCATACGTGTCCTCCT
TACCAGAAATTTATCCTTAAGGTCGTCAGCTATCC
TGCAGGCGATCTCTCGATTTCGATCAAGACATTCC
TTTAATGGTCTTTTCTGGACACCACTAGGGGTCAG
AAGTAGTTCATCAAACTTTCTTCCCTCCCTAATCT
CATTGGTTACCTTGGGCTATCGAAACTTAATTAAC
CAGTCAAGTCAGCTACTTGGCGAGATCGACTTGTC
TGGGTTTCGACTACGCTCAGAATTGCGTCAGTCAA
GTTCGATCTGGTCCTTGCTATTGCACCCGTTCTCC
GATTACGAGTTTCATTTAAATCATGTGAGCAAAAG
GCCAGCAAAAGGCCAGGAACCGTAAAAAGGCCGCG
TTGCTGGCGTTTTTCCATAGGCTCCGCCCCCCTGA
CGAGCATCACAAAAATCGACGCTCAAGTCAGAGGT -continued GGCGAAACCCGACAGGACTATAAAGATACCAGGCG
TTTCCCCCTGGAAGCTCCCTCGTGCGCTCTCCTGT
TCCGACCCTGCCGCTTACCGGATACCTGTCCGCCT
TTCTCCCTTCGGGAAGCGTGGCGCTTTCTCATAGC
TCACGCTGTAGGTATCTCAGTTCGGTGTAGGTCGT
TCGCTCCAAGCTGGGCTGTGTGCACGAACCCCCCG
TTCAGCCCGACCGCTGCGCCTTATCCGGTAACTAT
CGTCTTGAGTCCAACCCGGTAAGACACGACTTATC
GCCACTGGCAGCAGCCACTGGTAACAGGATTAGCA
GAGCGAGGTATGTAGGCGGTGCTACAGAGTTCTTG
AAGTGGTGGCCTAACTACGGCTACACTAGAAGAAC
AGTATTTGGTATCTGCGCTCTGCTGAAGCCAGTTA
CCTTCGGAAAAAGAGTTGGTAGCTCTTGATCCGGC
AAACAAACCACCGCTGGTAGCGGTGGTTTTTTTGT
TTGCAAGCAGCAGATTACGCGCAGAAAAAAAGGAT
CTCAAGAAGATCCTTTGATCTTTTCTACGGGGTCT
GACGCTCAGTGGAACGAAAACTCACGTTAAGGGAT
TTTGGTCATGAGATTATCAAAAAGGATCTTCACCT
AGATCCTTTTAAATTAAAAATGAAGTTTTAAATCA
ATCTAAAGTATATATGAGTAAACTTGGTCTGACAG
TTACCAATGCTTAATCAGTGAGGCACCTATCTCAG
CGATCTGTCTATTTCGTTCATCCATAGTTGCATTT
AAATTTCCGAACTCTCCAAGGCCCTCGTCGGAAAA
TCTTCAAACCTTTCGTCCGATCCATCTTGCAGGCT
ACCTCTCGAACGAACTATCGCAAGTCTCTTGGCCG
GCCTTGCGCCTTGGCTATTGCTTGGCAGCGCCTAT
CGCCAGGTATTACTCCAATCCCGAATATCCGAGAT
CGGGATCACCCGAGAGAAGTTCAACCTACATCCTC
AATCCCGATCTATCCGAGATCCGAGGAATATCGAA
ATCGGGGCGCGCCTGGTGTACCGAGAACGATCCTC
TCAGTGCGAGTCTCGACGATCCATATCGTTGCTTG
GCAGTCAGCCAGTCGGAATCCAGCTTGGGACCCAG
GAAGTCCAATCGTCAGATATTGTACTCAAGCCTGG
TCACGGCAGCGTACCGATCTGTTTAAACCTAGATA
TTGATAGTCTGATCGGTCAACGTATAATCGAGTCC
TAGCTTTTGCAAACATCTATCAAGAGACAGGATCA
GCAGGAGGCTTTCGCATGAGTATTCAACATTTCCG
TGTCGCCCTTATTCCCTTTTTTGCGGCATTTTGCC
TTCCTGTTTTTGCTCACCCAGAAACGCTGGTGAAA
GTAAAAGATGCTGAAGATCAGTTGGGTGCGCGAGT -continued

```
GGGTTACATCGAACTGGATCTCAACAGCGGTAAGA

TCCTTGAGAGTTTTCGCCCCGAAGAACGCTTTCCA

ATGATGAGCACTTTTAAAGTTCTGCTATGTGGCGC

GGTATTATCCCGTATTGACGCCGGGCAAGAGCAAC

TCGGTCGCCGCATACACTATTCTCAGAATGACTTG

GTTGAGTATTCACCAGTCACAGAAAAGCATCTTAC

GGATGGCATGACAGTAAGAGAATTATGCAGTGCTG

CCATAACCATGAGTGATAACACTGCGGCCAACTTA

CTTCTGACAACGATTGGAGGACCGAAGGAGCTAAC

CGCTTTTTTGCACAACATGGGGGATCATGTAACTC

GCCTTGATCGTTGGGAACCGGAGCTGAATGAAGCC

ATACCAAACGACGAGCGTGACACCACGATGCCTGT

AGCAATGGCAACAACCTTGCGTAAACTATTAACTG

GCGAACTACTTACTCTAGCTTCCCGGCAACAGTTG

ATAGACTGGATGGAGGCGGATAAAGTTGCAGGACC

ACTTCTGCGCTCGGCCCTTCCGGCTGGCTGGTTTA

TTGCTGATAAATCTGGAGCCGGTGAGCGTGGGTCT

CGCGGTATCATTGCAGCACTGGGGCCAGATGGTAA

GCCCTCCCGTATCGTAGTTATCTACACGACGGGGA

GTCAGGCAACTATGGATGAACGAAATAGACAGATC

GCTGAGATAGGTGCCTCACTGATTAAGCATTGGTA

ACCGATTCTAGGTGCATTGGCGCAGAAAAAAATGC

CTGATGCGACGCTGCGCGTCTTATACTCCCACATA

TGCCAGATTCAGCAACGGATACGGCTTCCCCAACT

TGCCCACTTCCATACGTGTCCTCCTTACCAGAAAT

TTATCCTTAAGATCCCGAATCGTTTAAACTCGACT

CTGGCTCTATCGAATCTCCGTCGTTTCGAGCTTAC

GCGAACAGCCGTGGCGCTCATTTGCTCGTCGGGCA

TCGAATCTCGTCAGCTATCGTCAGCTTACCTTTTT

GGCA.
```

The cultures were supplemented with 1 mM NR at time of transfection to minimize toxicity from ARM-SAM-TIR overexpression. Forty-eight hours after transfection, cells were harvested, pelleted by centrifugation at 1,000 rpm (Sorvall ST 16R centrifuge, Thermo Fisher), and washed once with cold PBS (0.01 M phosphate buffered saline NaCl 0.138 M; KCl 0.0027 M; pH 7.4). The cells were resuspended in PBS with protease inhibitors (cOmplete™ protease inhibitor cocktail, Roche product #11873580001) and cell lysates were prepared by sonication (Branson Sonifer 450, output=3, 20 episodes of stroke). The lysates were centrifuged (12,000×g for 10 min at 4° C.) to remove cell debris and the supernatants (containing ARM-SAM-TIR protein) were stored at −80° C. for later use in the in vitro ARM-SAM-TIR NADase assay (see below). Protein concentration was determined by the Bicinchoninic (BCA) method and used to normalize lysate concentrations.

ARM-SAM-TIR IC50 Assay of Formula I Compounds.

The enzymatic assay was performed in a 384-well polypropylene plate in Dulbecco's PBS buffer in a final assay volume of 20 μL. ARM-SAM-TIR lysate with a final concentration of 5 μg/mL was pre-incubated with the respective compound at 1% DMSO final assay concentration over 2 h at room temperature. The reaction was initiated by addition of 5 μM final assay concentration of NAD+ as substrate. After a 2 hr room temperature incubation, the reaction was terminated with 40 μL of stop solution of 7.5% trichloroacetic acid in acetonitrile. The NAD+ and ADPR concentrations were analyzed by a RapidFire High Throughput Mass Spectrometry System (Agilent Technologies, Santa Clara, Calif.) using an API4000 triple quadrupole mass spectrometer (AB Sciex Framingham, Mass.).

Results are presented below in Table 2. Compounds having an activity designated as "A" provided an $IC_{50}$<5 μM; compounds having an activity designated as "B" provided an $IC_{50}$ 5-15 μM; compounds having an activity designated as "C" provided an $IC_{50}$ 15.01-30 μM; compounds having an activity designated as "D" provided an $IC_{50}$>30 μM; nd: not determined.

TABLE 2

| Example | SARM1 $IC_{50}$ (μM) |
|---|---|
| 1 | nd |
| 2 | D |
| 3 | B |
| 4 | nd |
| 5 | nd |
| 6 | nd |
| 7 | B |
| 8 | B |
| 9 | B |
| 10 | C |
| 11 | nd |
| 12 | B |
| 13 | D |
| 14 | B |
| 15 | D |
| 16 | C |
| 17 | D |
| 18 | nd |
| 19 | nd |
| 20 | B |
| 21 | C |
| 22 | B |
| 23 | B |
| 24 | D |
| 25 | C |
| 26 | B |
| 27 | B |
| 28 | B |
| 29 | nd |
| 30 | D |
| 31 | C |
| 32 | C |
| 33 | B |
| 34 | D |
| 35 | B |
| 36 | nd |
| 37 | B |
| 38 | B |
| 39 | B |
| 40 | nd |
| 41 | D |
| 42 | B |
| 43 | C |
| 44 | B |
| 45 | B |
| 46 | D |
| 47 | A |
| 48 | C |
| 49 | nd |

TABLE 2-continued

| Example | SARM1 $IC_{50}$ (μM) |
|---|---|
| 50 | C |
| 51 | D |
| 52 | nd |
| 53 | nd |
| 54 | B |
| 55 | C |
| 56 | B |
| 57 | nd |
| 58 | B |
| 59 | C |
| 60 | nd |
| 61 | A |
| 62 | nd |
| 63 | A |
| 64 | B |
| 65 | B |
| 66 | B |
| 67 | B |
| 68 | B |
| 69 | nd |
| 70 | B |
| 71 | nd |
| 72 | D |
| 73 | B |
| 74 | nd |
| 75 | D |
| 76 | D |
| 77 | B |
| 78 | nd |
| 79 | nd |
| 80 | B |
| 81 | B |
| 82 | nd |
| 83 | nd |
| 84 | B |
| 85 | B |
| 86 | B |
| 87 | nd |
| 88 | nd |
| 89 | C |
| 90 | C |
| 91 | C |
| 92 | B |
| 93 | B |
| 94 | C |
| 95 | D |
| 96 | nd |
| 97 | nd |
| 98 | B |
| 99 | nd |
| 100 | B |
| 101 | A |
| 102 | nd |
| 103 | nd |
| 104 | B |
| 105 | A |
| 106 | B |
| 107 | B |
| 108 | D |
| 109 | B |
| 110 | D |
| 111 | D |
| 112 | B |
| 113 | B |
| 114 | B |
| 115 | D |
| 116 | C |
| 117 | D |
| 118 | A |
| 119 | A |
| 120 | A |
| 121 | B |
| 122 | B |
| 123 | B |
| 124 | B |
| 125 | B |
| 126 | B |

TABLE 2-continued

| Example | SARM1 $IC_{50}$ (μM) |
|---|---|
| 127 | C |
| 128 | B |
| 129 | B |
| 130 | B |
| 131 | A |
| 132 | B |
| 133 | B |
| 134 | C |
| 135 | C |
| 136 | B |
| 137 | D |
| 138 | C |
| 139 | B |
| 140 | C |
| 141 | B |
| 142 | B |
| 143 | B |
| 144 | B |
| 145 | D |
| 146 | B |
| 147 | B |
| 148 | B |
| 149 | B |
| 150 | B |
| 151 | B |
| 152 | A |
| 153 | D |
| 154 | D |
| 155 | B |
| 156 | C |
| 157 | C |
| 158 | C |
| 159 | C |
| 160 | C |
| 161 | D |
| 162 | D |
| 163 | B |
| 164 | D |
| 165 | D |
| 166 | C |
| 167 | C |
| 168 | D |
| 169 | D |
| 170 | D |
| 171 | B |
| 172 | D |
| 173 | D |
| 174 | A |
| 175 | D |
| 176 | D |
| 177 | D |
| 178 | D |
| 179 | nd |
| 180 | nd |
| 181 | nd |
| 182 | D |
| 183 | D |
| 184 | D |
| 185 | D |
| 186 | D |
| 187 | D |
| 188 | D |
| 189 | D |
| 190 | D |
| 191 | D |
| 192 | D |
| 193 | D |
| 194 | nd |
| 195 | D |
| 196 | D |
| 197 | D |
| 198 | D |
| 199 | D |
| 200 | D |
| 201 | D |
| 202 | D |
| 203 | D |

TABLE 2-continued

| Example | SARM1 $IC_{50}$ (µM) |
|---|---|
| 204 | D |
| 205 | D |
| 206 | D |
| 207 | D |
| 208 | D |
| 209 | D |
| 210 | D |
| 211 | B |
| 212 | D |
| 213 | D |
| 214 | D |
| 215 | D |
| 216 | D |
| 217 | D |
| 218 | D |
| 219 | D |

Example 4: Axonal Degeneration Index

This Example illustrates an in vitro axon degeneration assay used to characterize compounds of Formula L. This assay is used to test the efficacy of the compounds of Formula I to prevent axonal degeneration in a mouse dorsal root ganglion (DRG) drop culture.

Mouse DRG Drop culture: Mouse dorsal root ganglion neurons (DRGs) are dissected out of E12.5 CD1 mice (50 ganglion per embryo) and incubated with 0.5% Trypsin solution containing 0.02% EDTA (Gibco) at 37° C. for 15 min. The cells are then triturated by gentle pipetting and washed 3 times with DRG growth medium (Neurobasal medium (Gibco) containing 2% B27 (Invitrogen), 100 ng/ml 2.5 S NGF (Harland Bioproducts), 1 mM 5-fluoro-2'deoxyuridine (Sigma), penicillin, and streptomycin). Cells are suspended in the DRG growth medium. DRG drop cultures are created by spotting 5000 cells/well into the center of each well of a 96-well tissue culture plate coated with poly-D-Lysine (0.1 mg/ml; Sigma) and laminin (3 mg/ml; Invitrogen). Cells are allowed to adhere to the plates in a humidified tissue culture incubator (5% $CO_2$) for 15 min and then DRG growth medium was gently added (100 ml well).

Axon degeneration assay: Axonal degeneration is stimulated either by manual axonal transection using a scalpel blade, or chemotoxic stimuli. After an appropriate experimental time period, the DRG cultures are fixed in 1% PFA plus sucrose and kept in the fridge prior to imaging. Bright-field images of DRG axons and cell bodies are collected using the 20× water immersion lens of a Phenix automated confocal microscope (PerkinElmer) and quantitation of axonal performed using in-house developed scripts (Acapella, PerkinElmer).

We claim:

1. A compound selected from the group consisting of:

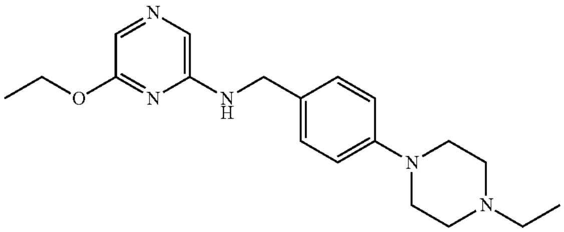

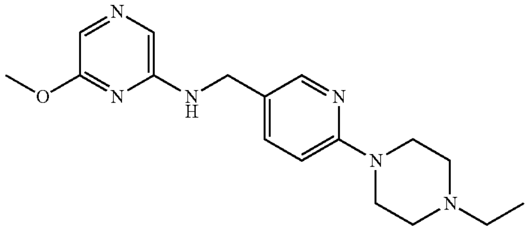

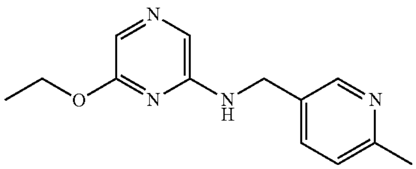

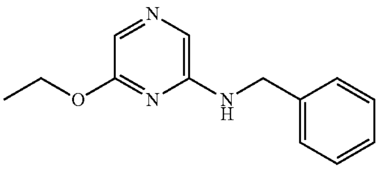

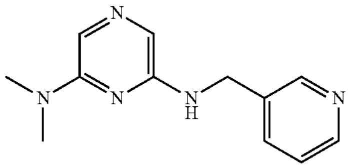

-continued

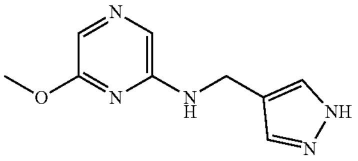

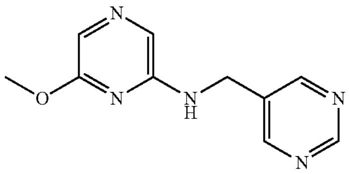

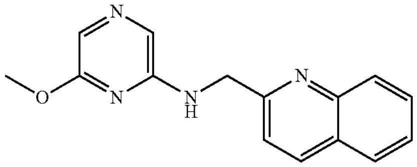

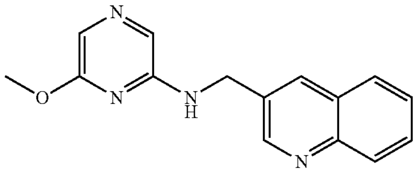

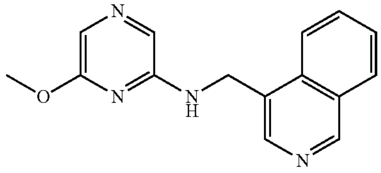

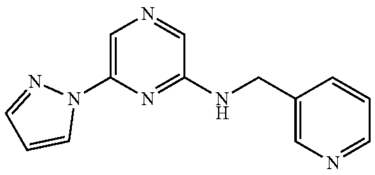

-continued
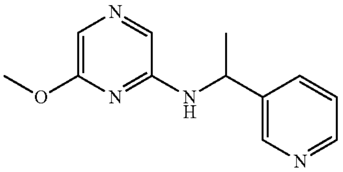
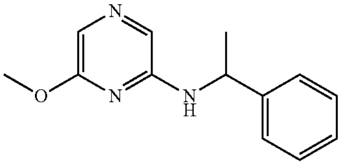
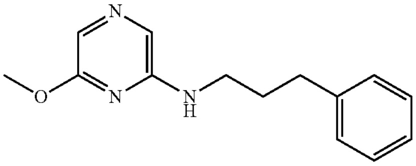
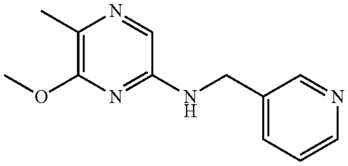
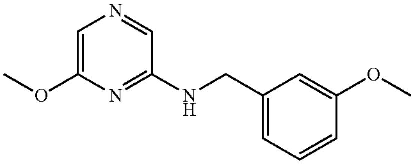
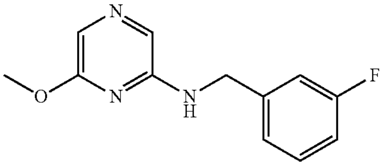
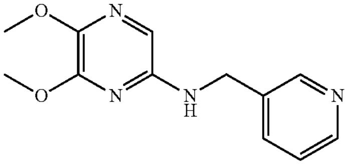
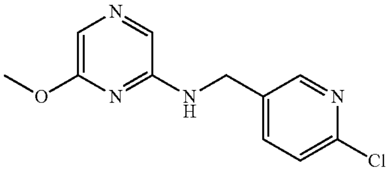
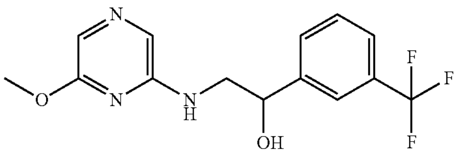
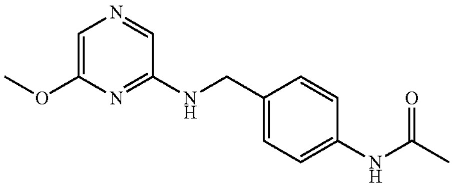
-continued
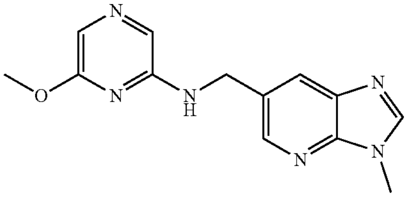
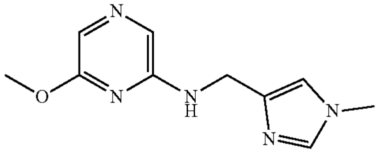
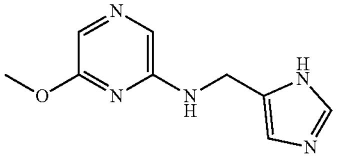
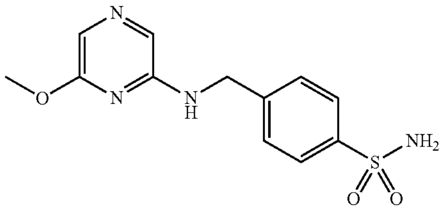
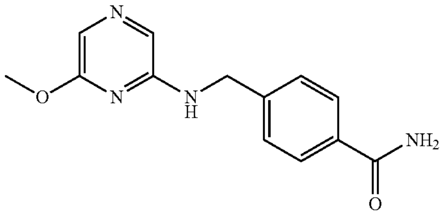
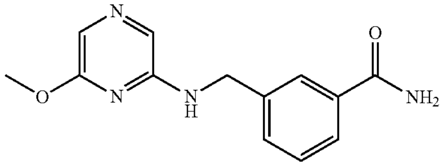
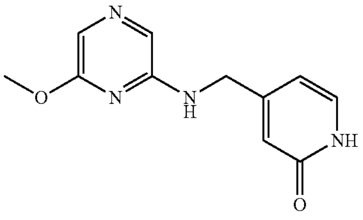
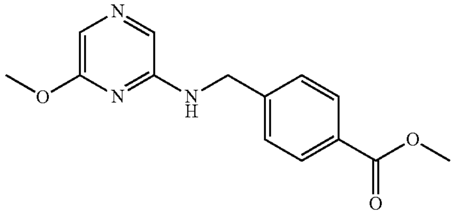
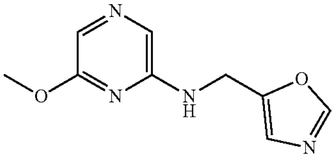

-continued
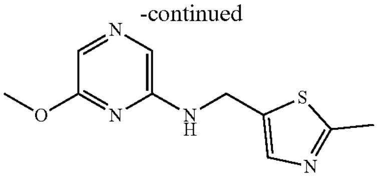
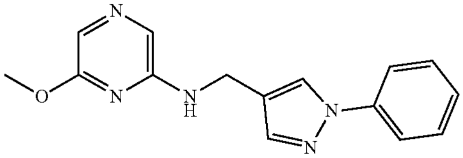
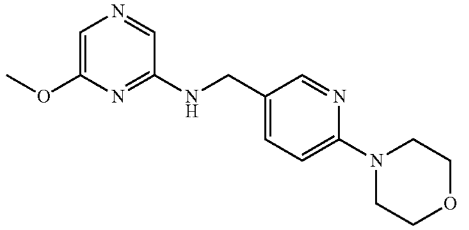
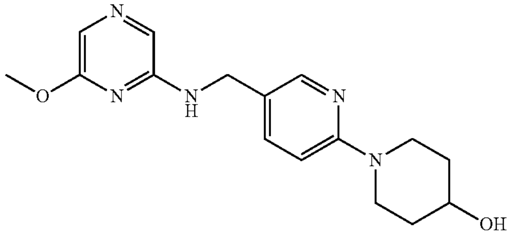
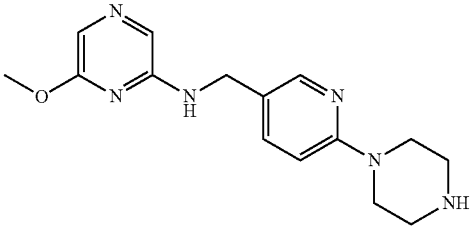
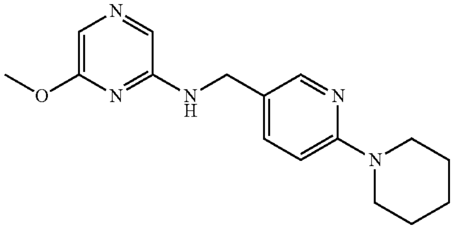
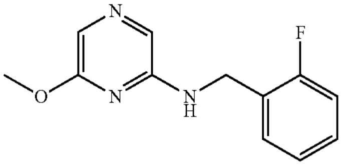
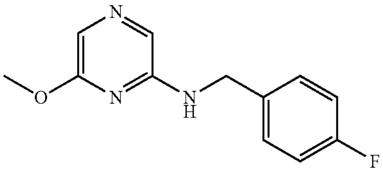
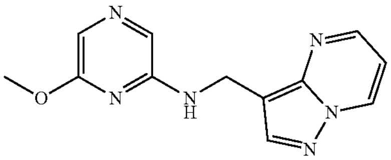
-continued
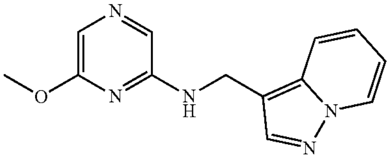
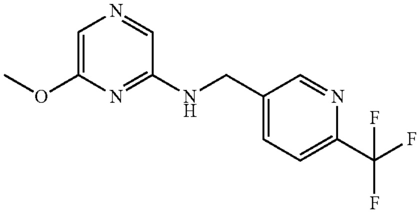
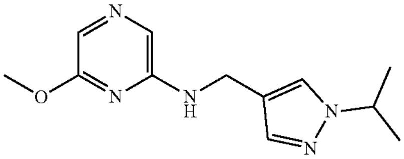
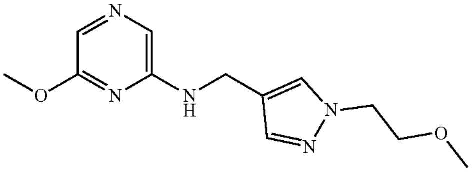
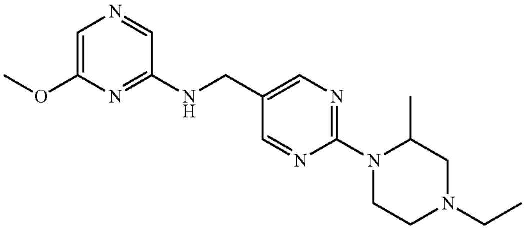
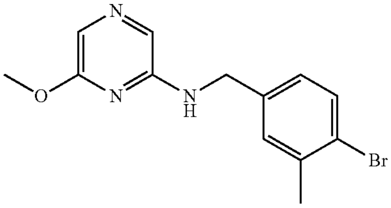
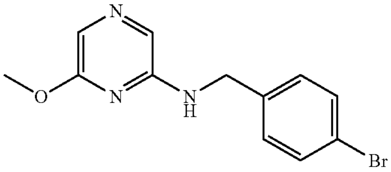
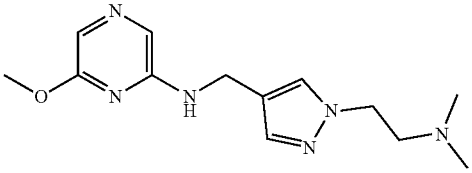
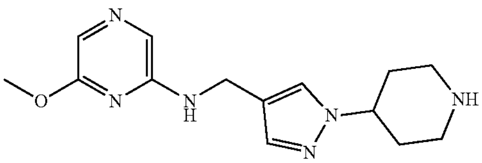

-continued
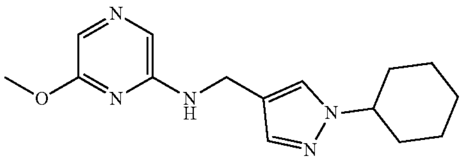
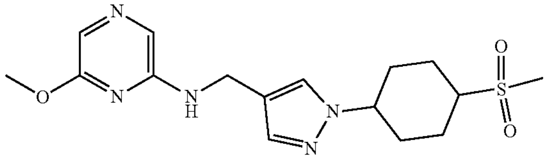
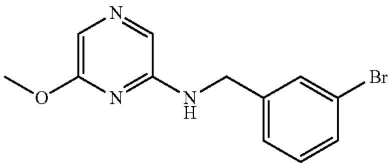
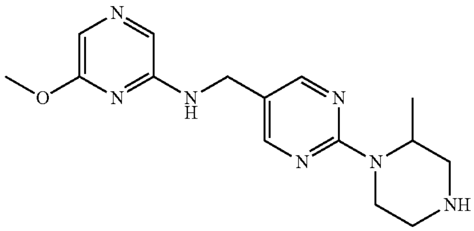
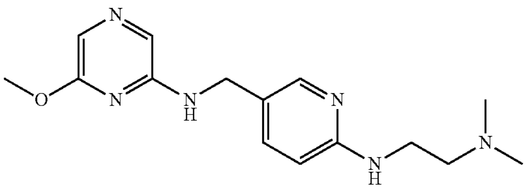
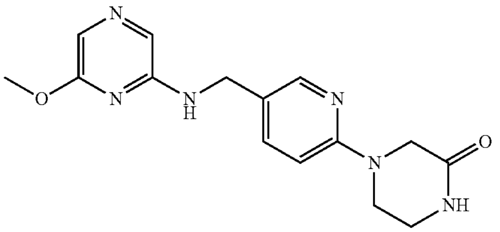
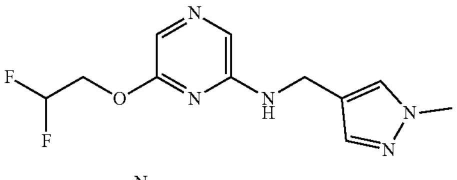
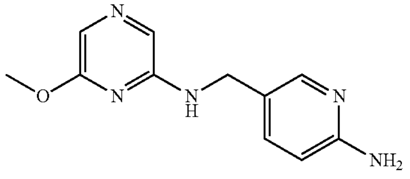
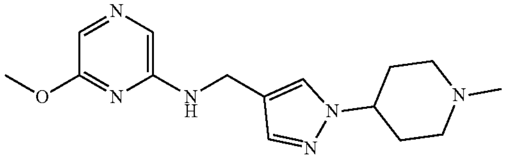
-continued
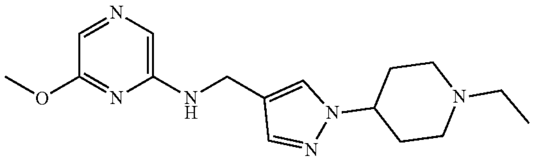
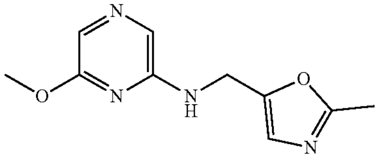
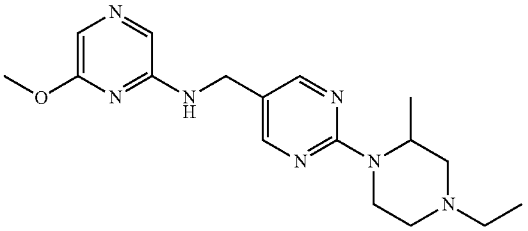
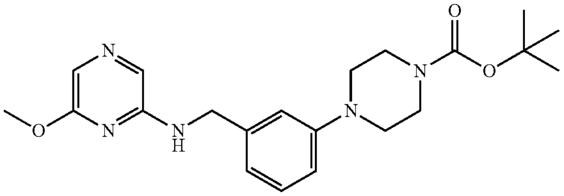
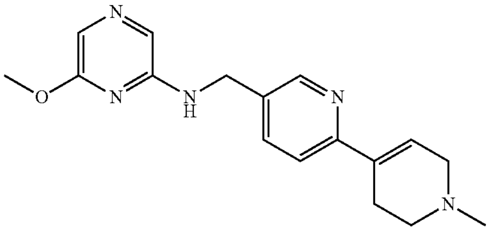
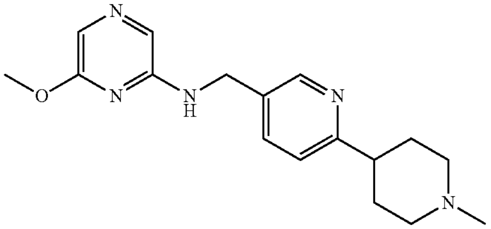
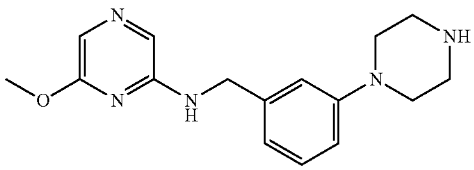
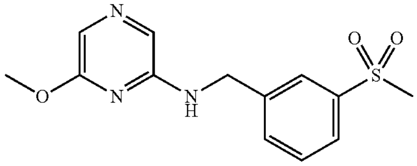
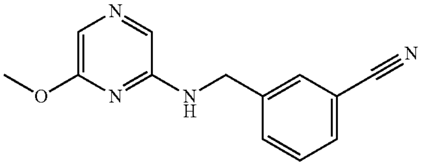

-continued
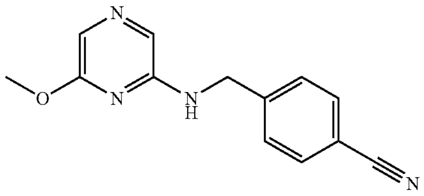
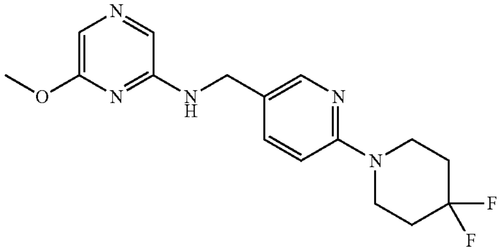
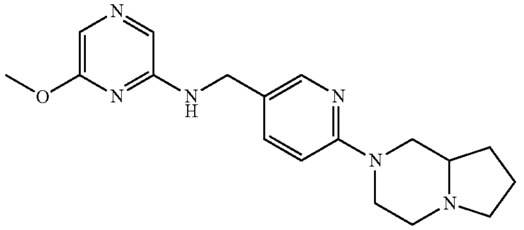
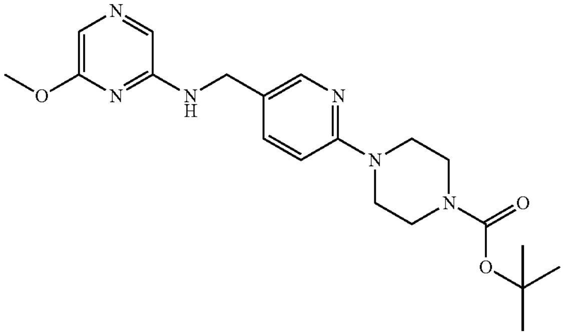
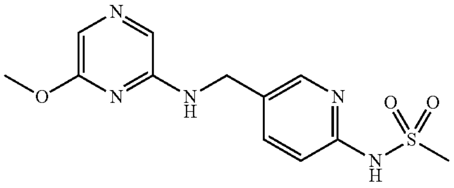
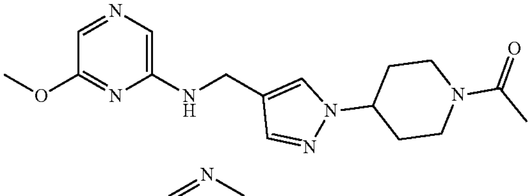
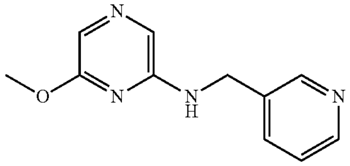
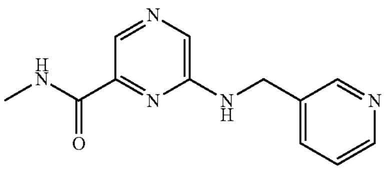
-continued
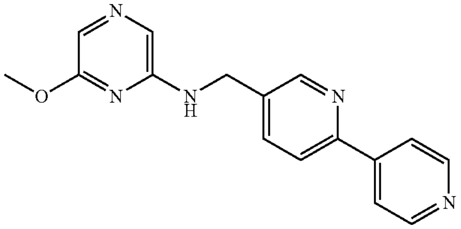
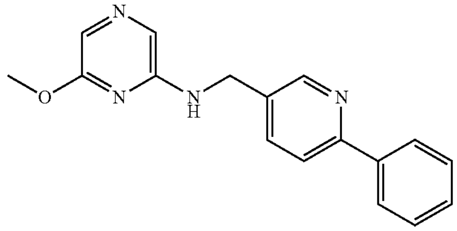
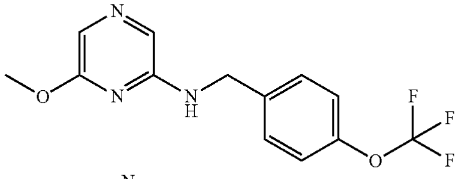
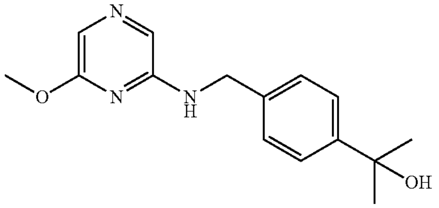
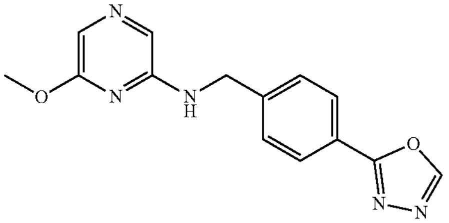
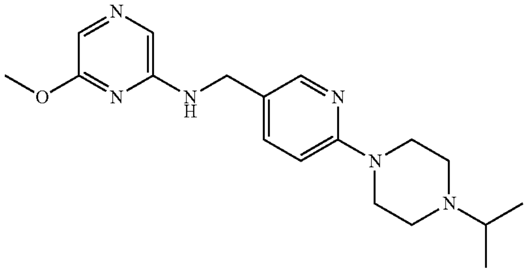
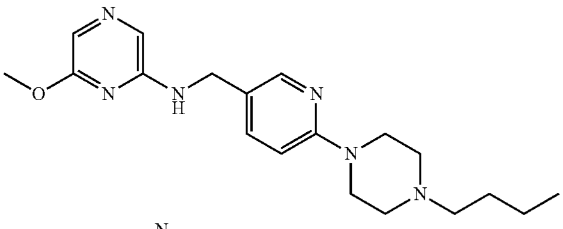
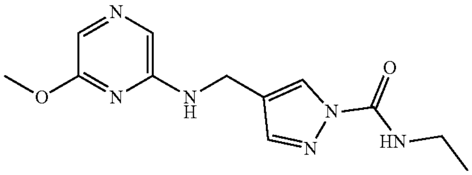

-continued

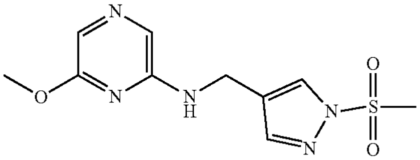

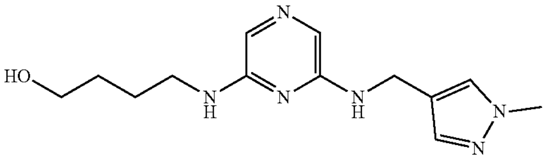

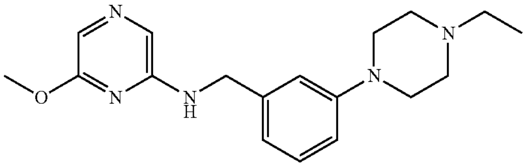

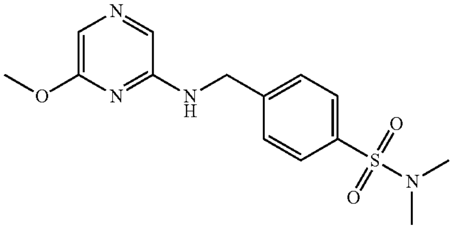

-continued

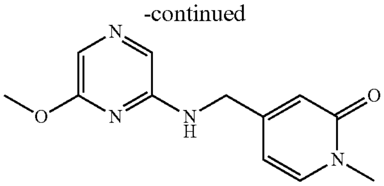

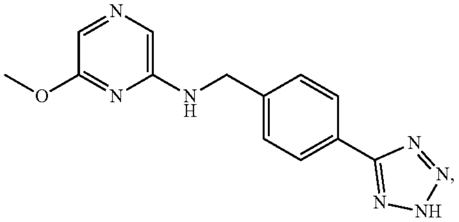

and or a pharmaceutically acceptable salt thereof.

2. A method comprising a step of: administering a compound of claim 1 to a subject who (i) has a condition characterized by axonal degeneration or (ii) is at risk of developing a condition characterized by axonal degeneration.

3. A method of treating or preventing axonal degeneration comprising administering to a subject in need thereof a compound of claim 1.

4. A method of inhibiting SARM1 comprising contacting a biological sample with a compound of claim 1.

* * * * *

SEQUENCE LISTING

<160> NUMBER OF SEQ ID NOS: 1

<210> SEQ ID NO 1
<211> LENGTH: 6514
<212> TYPE: DNA
<213> ORGANISM: Artificial Sequence
<220> FEATURE:
<223> OTHER INFORMATION: Chemically synthesized oligonucleotide

<400> SEQUENCE: 1
gcgatcgcgg ctcccgacat cttggaccat tagctccaca ggtatcttct tccctctagt 60
ggtcataaca gcagcttcag ctacctctca attcaaaaaa cccctcaaga cccgtttaga 120
ggccccaagg ggttatgcta tcaatcgttg cgttacacac acaaaaaacc aacacacatc 180
catcttcgat ggatagcgat tttattatct aactgctgat cgagtgtagc cagatctagt 240
aatcaattac ggggtcatta gttcatagcc catatatgga gttccgcgtt acataactta 300
cggtaaatgg cccgcctggc tgaccgccca acgacccccg cccattgacg tcaataatga 360
cgtatgttcc catagtaacg ccaataggga ctttccattg acgtcaatgg gtggagtatt 420
tacggtaaac tgcccacttg gcagtacatc aagtgtatca tatgccaagt acgcccccta 480
ttgacgtcaa tgacggtaaa tggcccgcct ggcattatgc ccagtacatg accttatggg 540
actttcctac ttggcagtac atctacgtat tagtcatcgc tattaccatg ctgatgcggt 600
tttggcagta catcaatggg cgtggatagc ggtttgactc acggggattt ccaagtctcc 660
accccattga cgtcaatggg agtttgtttt ggcaccaaaa tcaacgggac tttccaaaat 720
gtcgtaacaa ctccgcccca ttgacgcaaa tgggcggtag gcgtgtacgg tgggaggtct 780
atataagcag agctggttta gtgaaccgtc agatcagatc tttgtcgatc ctaccatcca 840
ctcgacacac ccgccagcgg ccgctgccaa gcttccgagc tctcgaattc aaaggaggta 900
cccaccatgg ccatgcatca ccaccaccat catagctccg gcgtcgacct cggcaccgag 960
aatttatatt tccaaagcgg cctcaatgat atcttcgagg cccagaagat cgagtggcac 1020

-continued

```
gagggcagct ccgacctcgc cgtgcccggt cccgatggag gcggaggcac tggtccttgg   1080
tgggctgctg gcggcagagg ccctagagaa gtgagccccg gtgctggcac cgaggtgcaa   1140
gacgctctgg agagggctct gcccgaactg cagcaagctc tgtccgcttt aaagcaagct   1200
ggaggagcta gagccgtcgg cgccggactg gccgaagtgt tccagctcgt ggaggaagct   1260
tggttattac ccgctgtggg aagagaggtc gcccaaggtc tgtgtgacgc cattcgtctg   1320
gacggaggtt tagacttatt actgaggctg ctgcaagctc ccgaactgga gacaagggtc   1380
caagctgctc gtctgctgga gcagatcctc gtggccgaga atcgtgacag agtggctaga   1440
atcggtttag gcgtcatcct caatttagcc aaagagaggg agcccgttga gctggccaga   1500
agcgtcgctg gcatcctcga gcacatgttc aagcattccg aggagacttg tcagagactg   1560
gtcgccgccg gaggactcga tgctgtttta tactggtgca gaaggacaga ccccgcttta   1620
ctgaggcatt gtgctctggc cctcggcaat tgcgctttac atggaggcca agccgtccag   1680
agaaggatgg tggagaaaag agccgccgag tggctgttcc ctttagcctt ctccaaagaa   1740
gacgaactgt tacgtctgca tgcttgtctc gctgtcgctg ttttagccac caacaaggag   1800
gtggaaaggg aagtggaaag aagcggaaca ctggctttag tcgaacctct ggtggcttct   1860
ttagatcccg gaaggtttgc cagatgtctg gtcgacgcca gcgatacctc ccaaggaaga   1920
ggccccgacg atctccagag actggtgcct ctgctggaca gcaatcgtct ggaggcccaa   1980
tgtattggcg ccttctatct ctgcgccgaa gccgccatca agtctttaca aggtaagacc   2040
aaggtgttct ccgacattgg agccatccaa tctttaaaga ggctggtgag ctattccacc   2100
aacggcacaa aaagcgcttt agccaaaaga gctttaagac tgctgggcga agaggtgcct   2160
aggcccattt taccttccgt gcctagctgg aaggaggccg aggtgcagac ttggctgcag   2220
cagatcggct ttagcaaata ttgcgaatcc tttagggagc agcaagttga cggcgattta   2280
ttattaaggc tgaccgagga agagctccag acagatttag gcatgaaaag cggcatcact   2340
cgtaagaggt tctttcgtga gctcaccgaa ctgaagacct tcgccaacta ctccacttgt   2400
gatcgtagca atttagctga ttggctcgga tccctcgatc ccagatttcg tcagtacacc   2460
tatggactcg tctcttgtgg actggacaga tctttactgc atcgtgtgag cgagcaacag   2520
ctgctggaag attgcggcat ccatttagga gtgcacagag ccagaattct gaccgccgct   2580
agagagatgc tgcattcccc tctcccttgt accggaggca agcctagcgg agacaccccc   2640
gacgtgttca tcagctatcg tagaaacagc ggaagccagc tggcctcttt actgaaggtc   2700
catttacagc tgcacggatt tagcgtcttc atcgacgtgg agaaactgga ggctggcaag   2760
ttcgaggaca agctgatcca gtccgtgatg ggcgctagga atttcgtttt agtgctcagc   2820
cccggcgctc tggataaatg catgcaagat catgactgta aggactgggt ccacaaggaa   2880
atcgtgaccg ctctgtcttg tggcaagaac atcgtcccca tcatcgacgg cttcgaatgg   2940
cccgagcctc aagttctccc cgaagatatg caagctgttt taaccttcaa tggaatcaag   3000
tggagccacg agtaccaaga agccacaatc gagaagatca ttcgttttct gcaaggtaga   3060
tcctccagag attcctccgc tggcagcgac acatctttag agggcgccgc ccctatgggt   3120
cctacctaat aatctagaag ttgtctcctc ctgcactgac tgactgatac aatcgatttc   3180
tggatccgca ggcctctgct agcttgactg actgagatac agcgtacctt cagctcacag   3240
acatgataag atacattgat gagtttggac aaaccacaac tagaatgcag tgaaaaaaat   3300
gctttatttg tgaaatttgt gatgctattg ctttatttgt aaccattata agctgcaata   3360
```

-continued

```
aacaagttaa caacaacaat tgcattcatt ttatgtttca ggttcagggg gaggtgtggg   3420
aggtttttta aagcaagtaa aacctctaca aatgtggtat tggcccatct ctatcggtat   3480
cgtagcataa ccccttgggg cctctaaacg ggtcttgagg ggttttttgt gcccctcggg   3540
ccggattgct atctaccggc attggcgcag aaaaaaatgc ctgatgcgac gctgcgcgtc   3600
ttatactccc acatatgcca gattcagcaa cggatacggc ttccccaact tgcccacttc   3660
catacgtgtc ctccttacca gaaatttatc cttaaggtcg tcagctatcc tgcaggcgat   3720
ctctcgattt cgatcaagac attcctttaa tggtcttttc tggacaccac taggggtcag   3780
aagtagttca tcaaactttc ttccctccct aatctcattg gttaccttgg gctatcgaaa   3840
cttaattaac cagtcaagtc agctacttgg cgagatcgac ttgtctgggt ttcgactacg   3900
ctcagaattg cgtcagtcaa gttcgatctg gtccttgcta ttgcacccgt tctccgatta   3960
cgagtttcat ttaaatcatg tgagcaaaag gccagcaaaa ggccaggaac cgtaaaaagg   4020
ccgcgttgct ggcgtttttc cataggctcc gcccccctga cgagcatcac aaaaatcgac   4080
gctcaagtca gaggtggcga aacccgacag gactataaag ataccaggcg tttccccctg   4140
gaagctccct cgtgcgctct cctgttccga ccctgccgct taccggatac ctgtccgcct   4200
ttctcccttc gggaagcgtg gcgctttctc atagctcacg ctgtaggtat ctcagttcgg   4260
tgtaggtcgt tcgctccaag ctgggctgtg tgcacgaacc ccccgttcag cccgaccgct   4320
gcgccttatc cggtaactat cgtcttgagt ccaacccggt aagacacgac ttatcgccac   4380
tggcagcagc cactggtaac aggattagca gagcgaggta tgtaggcggt gctacagagt   4440
tcttgaagtg gtggcctaac tacggctaca ctagaagaac agtatttggt atctgcgctc   4500
tgctgaagcc agttaccttc ggaaaaagag ttggtagctc ttgatccggc aaacaaacca   4560
ccgctggtag cggtggtttt tttgtttgca agcagcagat tacgcgcaga aaaaaaggat   4620
ctcaagaaga tcctttgatc ttttctacgg ggtctgacgc tcagtggaac gaaaactcac   4680
gttaagggat tttggtcatg agattatcaa aaaggatctt cacctagatc cttttaaatt   4740
aaaaatgaag ttttaaatca atctaaagta tatatgagta aacttggtct gacagttacc   4800
aatgcttaat cagtgaggca cctatctcag cgatctgtct atttcgttca tccatagttg   4860
catttaaatt tccgaactct ccaaggccct cgtcggaaaa tcttcaaacc tttcgtccga   4920
tccatcttgc aggctacctc tcgaacgaac tatcgcaagt ctcttggccg gccttgcgcc   4980
ttggctattg cttggcagcg cctatcgcca ggtattactc caatcccgaa tatccgagat   5040
cgggatcacc cgagagaagt tcaacctaca tcctcaatcc cgatctatcc gagatccgag   5100
gaatatcgaa atcggggcgc gcctggtgta ccgagaacga tcctctcagt gcgagtctcg   5160
acgatccata tcgttgcttg gcagtcagcc agtcggaatc cagcttggga cccaggaagt   5220
ccaatcgtca gatattgtac tcaagcctgg tcacggcagc gtaccgatct gtttaaacct   5280
agatattgat agtctgatcg gtcaacgtat aatcgagtcc tagcttttgc aaacatctat   5340
caagagacag gatcagcagg aggctttcgc atgagtattc aacatttccg tgtcgccctt   5400
attccctttt ttgcggcatt ttgccttcct gtttttgctc acccagaaac gctggtgaaa   5460
gtaaaagatg ctgaagatca gttgggtgcg cgagtgggtt acatcgaact ggatctcaac   5520
agcggtaaga tccttgagag ttttcgcccc gaagaacgct ttccaatgat gagcactttt   5580
aaagttctgc tatgtggcgc ggtattatcc cgtattgacg ccgggcaaga gcaactcggt   5640
cgccgcatac actattctca gaatgacttg gttgagtatt caccagtcac agaaaagcat   5700
cttacggatg gcatgacagt aagagaatta tgcagtgctg ccataaccat gagtgataac   5760
```

-continued

| | |
|---|---|
| actgcggcca acttacttct gacaacgatt ggaggaccga aggagctaac cgcttttttg | 5820 |
| cacaacatgg gggatcatgt aactcgcctt gatcgttggg aaccggagct gaatgaagcc | 5880 |
| ataccaaacg acgagcgtga caccacgatg cctgtagcaa tggcaacaac cttgcgtaaa | 5940 |
| ctattaactg gcgaactact tactctagct tcccggcaac agttgataga ctggatggag | 6000 |
| gcggataaag ttgcaggacc acttctgcgc tcggcccttc cggctggctg gtttattgct | 6060 |
| gataaatctg gagccggtga gcgtgggtct cgcggtatca ttgcagcact ggggccagat | 6120 |
| ggtaagccct cccgtatcgt agttatctac acgacgggga gtcaggcaac tatggatgaa | 6180 |
| cgaaatagac agatcgctga gataggtgcc tcactgatta agcattggta accgattcta | 6240 |
| ggtgcattgg cgcagaaaaa aatgcctgat gcgacgctgc gcgtcttata ctcccacata | 6300 |
| tgccagattc agcaacggat acggcttccc caacttgccc acttccatac gtgtcctcct | 6360 |
| taccagaaat ttatccttaa gatcccgaat cgtttaaact cgactctggc tctatcgaat | 6420 |
| ctccgtcgtt tcgagcttac gcgaacagcc gtggcgctca tttgctcgtc gggcatcgaa | 6480 |
| tctcgtcagc tatcgtcagc ttaccttttt ggca | 6514 |